US012398192B2

(12) United States Patent
Schreiber et al.

(10) Patent No.: US 12,398,192 B2
(45) Date of Patent: Aug. 26, 2025

(54) CANCER TREATMENT WITH 237 CAR-T CELL BASED THERAPEUTICS RECOGNIZING THE Tn EPITOPE

(71) Applicants: The University of Chicago, Chicago, IL (US); The Board of Trustees of the University of Illinois, Urbana, IL (US)

(72) Inventors: Hans Schreiber, Chicago, IL (US); David Kranz, Champaign, IL (US); Karin Schreiber, Chicago, IL (US); Yanran He, Chicago, IL (US); Preeti Sharma, Urbana, IL (US)

(73) Assignees: The University of Chicago, Chicago, IL (US); The Board of Trustees of the University of Illinois, Urbana, IL (US)

( * ) Notice: Subject to any disclaimer, the term of this patent is extended or adjusted under 35 U.S.C. 154(b) by 1188 days.

(21) Appl. No.: 17/250,832

(22) PCT Filed: Sep. 11, 2019

(86) PCT No.: PCT/US2019/050652

§ 371 (c)(1),
(2) Date: Mar. 9, 2021

(87) PCT Pub. No.: WO2020/056023

PCT Pub. Date: Mar. 19, 2020

(65) Prior Publication Data

US 2022/0047631 A1 Feb. 17, 2022

Related U.S. Application Data

(60) Provisional application No. 62/729,951, filed on Sep. 11, 2018.

(51) Int. Cl.

| | |
|---|---|
| ***C07K 14/70*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/725*** | (2006.01) |
| ***C07K 14/735*** | (2006.01) |
| ***C07K 16/18*** | (2006.01) |
| ***C12N 5/0783*** | (2010.01) |

(52) U.S. Cl.

CPC .......... *C07K 14/7051* (2013.01); *A61K 40/11* (2025.01); *A61K 40/31* (2025.01); *A61K 40/4259* (2025.01); *A61P 35/00* (2018.01); *C07K 14/70535* (2013.01); *C07K 16/18* (2013.01); *C12N 5/0638* (2013.01); *A61K 2239/13* (2023.05); *A61K 2239/31* (2023.05); *A61K 2239/38* (2023.05); *A61K 2239/48* (2023.05); *A61K 2239/59* (2023.05)

(58) Field of Classification Search

CPC .......... C07K 14/7051; C07K 14/70535; C07K 16/18; A61K 39/4611; A61K 39/4631; A61K 39/464472; A61K 2239/13; A61K 2239/31; A61K 2239/38; A61K 2239/48; A61K 2239/59; A61P 35/00; C12N 5/0638; C12N 15/62; C12N 2510/00

See application file for complete search history.

(56) References Cited

U.S. PATENT DOCUMENTS

2006/0235201 A1* 10/2006 Kischel .................. A61P 35/00 435/325
2017/0166652 A1 6/2017 Schreiber et al.

FOREIGN PATENT DOCUMENTS

WO WO 2004/069876 8/2004

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Akita et al., "Developmental expression of a unique carbohydrate antigen, Tn antigen, in mouse central nervous tissues." *J Neurosci Res* 2001, 65, 595-603.
Ando et al., "Mouse-human chimeric anti-Tn IgGl induced anti-tumor activity against Jurkat cells in vitro andin vivo." *Biol Pharm Bull* 2008, 31:1739-1744.
Apostolopoulos et al., "A glycopeptide in complex with MHC class I uses the GalNAc residue as an anchor" *Proc Natl Acad Sci USA* 2003, 100, 15029-15034.
Blixt et al., "Analysis of Tn antigenicity with a panel of new IgM and IgG1 monoclonal antibodies raised against leukemic cells" *Glycobiology* 2012, 22(4), 529-542.
Brentjens et al. "Eradication of systemic B-cell tumors by genetically targeted human T lymphocytes co-stimulated by CD80 and interleukin-15." Nat Med 2003, 9, 279-286.
Brooks et al., "Antibody recognition of a unique tumor-specific glycopeptide antigen" *Proc. Natl. Acad. Sci.* (*USA*) 2010, 107(22), 10056-10061.
Chekmasova et al., "Successful eradication of established peritoneal ovarian tumors in SCID-Beige mice following adoptive transfer of T cells genetically targeted to the MUC16 antigen" *Clin Cancer Res* 2010, 16, 3594-3606.
Dharma Rao et al., "Novel monoclonal antibodies against the proximal (carboxy-terminal) portions of MUC16." *Appl Immunohistochem Mol Morphol* 2010, 18, 462-472.
Haridas et al., "MUC16: molecular analysis and its functional implications in benign and malignant conditions." *FASEB J* 2014, 28, 4183-4199.
International Search Report and Written Opinion issued in Corresponding PCT Application No. PCT/US2019/050652, dated Jan. 31, 2020.

(Continued)

*Primary Examiner* — Nelson B Moseley, II

(74) *Attorney, Agent, or Firm* — Norton Rose Fulbright US LLP

(57) ABSTRACT

The disclosure provides Tn epitope-specific chimeric antigen receptors and scFvs, including soluble scFvs and multimeric scFvs, as well as methods of identifying cancer subjects and cancer subject sub-populations amenable to anti-Tn immunotherapy and methods of treating cancer.

17 Claims, 49 Drawing Sheets

Specification includes a Sequence Listing.

(56) References Cited

OTHER PUBLICATIONS

Ju et al., "Human Tumor Antigens Tn and Sialyl Tn Arise from Mutations in Cosmc" *Cancer Res* 2008, 68, 1636-1646.
Ju et al., "The Tn Antigen—Structural Simplicity and Biological Complexity" *Angew Chem Int Ed Engl* 2011, 50, 1770-1791.
Ju, T. and R.D. Cummings., "A unique molecular chaperone Cosmc required for activity of the mammalian core 1 β3-galactosyltransferase" *Proc Natl Acad Sci USA* 2002, 99, 16613-16618.
Kufe, D.W. "Mucins in cancer: function, prognosis and therapy." *Nat Rev Cancer* 2009, 9, 874-885.
Lavrsen et al., "Aberrantly glycosylated MUCI is expressed on the surface of breast cancer cells and a target for antibody-dependent cell-mediated cytotoxicity." *Glycoconj J* 2013, 30, 227-236.
Li et al., "Resolving conflicting data on expression of the Tn antigen and implications for clinical trials with cancer vaccines." *Mol Cancer Ther* 2009, 8, 971-979.
Marcos-Silva et al., "A novel monoclonal antibody to a defined peptide epitope in MUC16." *Glycobiology* 2015, 25, 1172-1182.
Milone et al., "Chimeric receptors containing CD137 signal transduction domains mediate enhanced survival of T cells and increased antileukemic efficacy in vivo." *Mol Ther* 2009, 17: 1453-1464.
Movahedin et al., "Glycosylation of MUCI influences the binding of a therapeutic antibody by altering the conformational equilibrium of the antigen." *Glycobiology*. 2017, 27(7):677-87.
Napoletano et al., "Tumor-Associated Tn-MUC1 Glycoform is Internalized through the Macrophage Galactose-Type C-Type Lectin and Delivered to the HLA Class I and II Compartments in Dendritic Cells" *Cancer Res* 2007, 67, 8358-8367.
Parkhurst et al., "T Cells Targeting Carcinoembryonic Antigen Can Mediate Regression of Metastatic Colorectal Cancer but Induce Severe Transient Colitis" *Mol Ther* 2011, 19, 620-626.
Posey et al., "Engineered CAR T Cells Targeting the Cancer-Associated Tn-Glycoform of the Membrane Mucin MUCI Control Adenocarcinoma." *Immunity* 2016, 44, 1444-1454.
Sharma P. and Kranz D.M., "Subtle changes at the variable domain interface of the T-cell receptor can strongly increase affinity." *J Biol Chem* 2018, 293, 1820-1834.
Sørensen et al., "Chemoenzymatically synthesized multimeric Tn/STn MUC1 glycopeptides elicit cancer-specific anti-MUC1 antibody responses and override tolerance" *Glycobiology* 2006, 16(2), 96-107.
Springer, G.F., "T and Tn, general carcinoma autoantigens" *Science* 1984, 224, 1198-1206.
Steentoft et al., "Characterization of an immunodominant cancer-specific O-glycopeptide epitope in murine podoplanin (OTS8)" *Glycoconj J* 2010, 27, 571-582.
Sun et al., "Differential expression of Cosmo, Tsynthase and mucins in Tn-positive colorectal cancers" *BMC Cancer* 2018, 18(827), 15 pages.
Tarp et al., "Identification of a novel cancer-specific immunodominant glycopeptide epitope in the MUC1 tandem repeat" *Glycobiology* 2007, 17(2), 197-209.
Van Elssen "Expression of aberrantly glycosylated Mucin-1 in ovarian cancer" *Histopathology* 2010, 57, 597-606.
Wang et al., "Cosmo is an essential chaperone for correct protein O-glycosylation." *Proc Natl Acad Sci USA* 2010, 107, 9228-9233.
Welinder et al., "A new murine IgGl anti-Tn monoclonal antibody with in vivo anti-tumor activity." *Glycobiology* 2011, 21, 1097-1107.
Yu, L.G. "The oncofetal Thomsen-Friedenreich carbohydrate antigen in cancer progression." *Glycoconj J* 2007, 24, 411-420.
Zlocowski et al., "Purified human anti-Tn and anti-T antibodies specifically recognize carcinorna tissues." *Scientific Reports* 2019, 9(8097), 11 pages.

* cited by examiner

| | | | | | | | | | | | | | | | | | |
|---|---|---|---|---|---|---|---|---|---|---|---|---|---|---|---|---|---|
| Cases affected | 34 | 6 | 9 | 8 | 7 | 1 | 5 | 6 | 4 | 4 | 3 | 1 | 3 | 2 | 5 | 1 | 1 |
| Total cases | 530 | 289 | 495 | 440 | 400 | 57 | 393 | 567 | 436 | 469 | 412 | 137 | 508 | 364 | 986 | 336 | 281 |

* The functional impacts of missense mutations are predicted by *PolyPhen*

-237 mAb crystallized with OTS-8 glycopeptide
-237 mAb recognizes both peptide and sugar
-OTS-8 glycopeptide bound to 237 Fab with $K_D$ ~ 140nM 237 Epitope on OTS8:

| 1 | 2 | 3 | 4 | 5 | 6 | 7 | 8 | 9 |
|---|---|---|---|---|---|---|---|---|
| G | T | K | P | P | L | E | E | L |

GalNAc

SEQ ID NO: 72

| Structure | Total contacts | Hydrogen bonds | van der Waal contacts | Buried surface area ($\Delta\text{Å}^2$) |
|---|---|---|---|---|
| *Glycopeptide* | 39 | 16 | 23 | 531.9 |
| Light chain | 12 | 8 | 4 | 262.5 |
| CDR L1 | 4 | 4 | 0 | 141.8 |
| CDR L2 | 0 | 0 | 0 | 18.4 |
| CDR L3 | 8 | 4 | 4 | 102.36 |
| Heavy chain | 26 | 11 | 15 | 269.4 |
| CDR H1 | 4 | 0 | 4 | 44.0 |
| CDR H2 | 20 | 9 | 11 | 219.3 |
| CDR H3 | 2 | 2 | 0 | 6.1 |
| GalNAc | 14 | 6 | 8 | 162.1 |
| Light chain | 4 | 1 | 3 | 85.6 |
| CDR L1 | 0 | 0 | 0 | 25.2 |
| CDR L2 | 0 | 0 | 0 | 0 |
| CDR L3 | 4 | 1 | 3 | 60.4 |
| Heavy chain | 10 | 5 | 5 | 76.5 |
| CDR H1 | 0 | 0 | 0 | 17.1 |
| CDR H2 | 7 | 4 | 3 | 53.5 |
| CDR H3 | 3 | 1 | 2 | 5.9 |

Figure 14

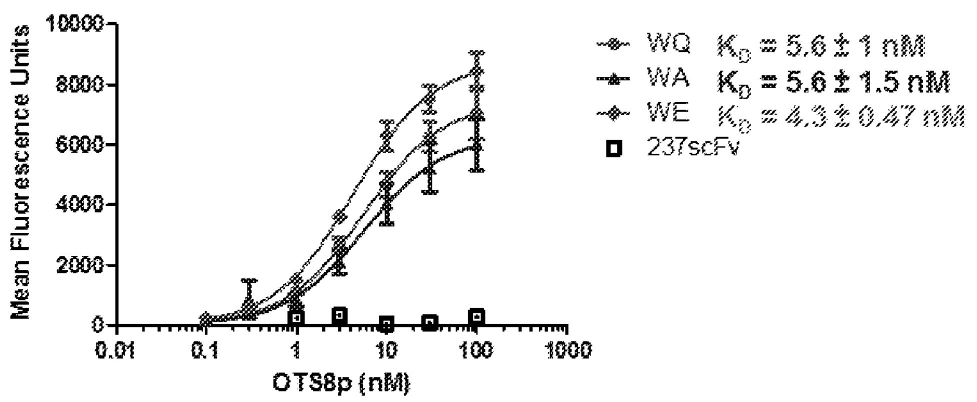

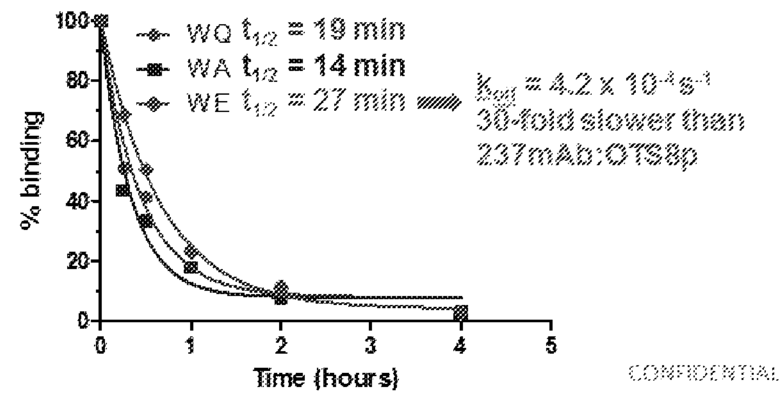

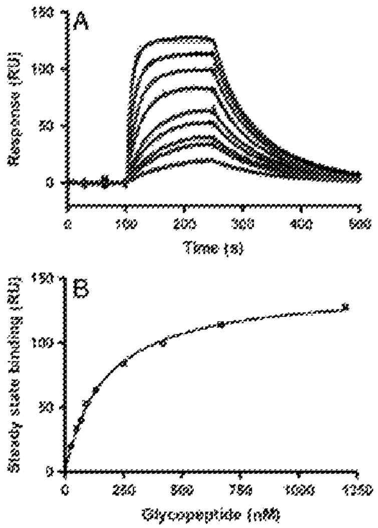

Fig. 3. Surface plasmon resonance of 237mAb binding to glycopeptide antigen. Sensorgram overlays of glycosylated peptide 2 (concentrations of 25, 50, 75, 90, 130, 250, 420, 626, and 1,200 nM) binding to 237mAbFab. Black lines indicate observed data points; red lines indicate fitted data (A). Steady state affinity fitting of 237mAb binding to the glycopeptide antigen (B).

CONFIDENTIAL

Table S3. Kinetic and binding constants of 237mAb to its glycopeptide antigen

| Antigen | $k_{assoc}$ (1/Ms) | $K_{dissoc}$ (1/s) | $K_D$ (M) |
|---|---|---|---|
| Glycopeptide | 9.4 × $10^4$ | 1.3 × $10^{-2}$ | 1.4 × $10^{-7}$ |
| Peptide | No binding detected | | |
| GalNAc | No binding detected | | |
| GalNAc glycoconjugate | No binding detected | | |

Brooks et al. (2010) *PNAS*

Figure 21

CONFIDENTIAL

CONFIDENTIAL

SEQUENCE LISTING

```
<160> NUMBER OF SEQ ID NOS: 80

<210> SEQ ID NO 1
<211> LENGTH: 118
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: 237 scFv Variable Heavy Region

<400> SEQUENCE: 1

Gln Val Gln Leu Gln Gln Ser Gly Gly Gly Leu Val Gln Pro Gly Gly
1               5                   10                  15

Ser Met Lys Ile Phe Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Asn Asn His Glu Thr Tyr Tyr Ala Glu
    50                  55                  60

Ser Val Lys Gly Arg Phe Thr Ile Thr Arg Asp Asp Ser Lys Ser Arg
65                  70                  75                  80

Met Ser Leu Gln Met Asn Ser Leu Arg Ala Glu Asp Thr Gly Ile Tyr
                85                  90                  95

Tyr Cys Ser Gly Gly Lys Val Arg Asn Ala Tyr Trp Gly Gln Gly Thr
            100                 105                 110

Thr Val Thr Val Ser Ser
        115


<210> SEQ ID NO 2
<211> LENGTH: 111
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: 237 scFv Variable Light Region

<400> SEQUENCE: 2

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45
```

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Phe Cys Ser Gln Ser
                85                  90                  95

Thr His Val Pro Thr Phe Gly Gly Gly Thr Lys Leu Glu Ile Lys
            100                 105                 110


<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDRL3 sequence

<400> SEQUENCE: 3

Thr Thr Trp Ala Pro
1               5


<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDRL3 sequence

<400> SEQUENCE: 4

Ser Thr Trp Ala Pro
1               5


<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDRL3 sequence

<400> SEQUENCE: 5

Ser Thr Trp Ser Pro
1               5


<210> SEQ ID NO 6
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDRL3 sequence

<400> SEQUENCE: 6

Ser Thr Trp Gly Pro
1               5


<210> SEQ ID NO 7
<211> LENGTH: 5
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDRL3 sequence

<400> SEQUENCE: 7

Ser Thr Trp Gln Pro
1               5


<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDRL3 sequence

<400> SEQUENCE: 8

Ser Thr Trp Glu Pro
1               5


<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDRL3 sequence

<400> SEQUENCE: 9

Ser Val Trp Glu Pro
1               5


<210> SEQ ID NO 10
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: 4 Ala substitutions for PPLE of the wild-type
      PDPN binding site for the 237 antibody
<220> FEATURE:
<221> NAME/KEY: MISC_FEATURE
<223> OTHER INFORMATION: peptide tested for 237 CAR-T cell binding

<400> SEQUENCE: 10

Gly Thr Lys Ala Ala Ala Ala
1               5


<210> SEQ ID NO 11
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: wild-type PDPN binding site for the 237
      antibody

<400> SEQUENCE: 11
```

Gly Thr Lys Pro Pro Leu Glu
1 5

<210> SEQ ID NO 12
<211> LENGTH: 30
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Tn-OTS8 peptide
<220> FEATURE:
<221> NAME/KEY: MISC_FEATURE
<222> LOCATION: (13)..(13)
<223> OTHER INFORMATION: GalNAc derivatization of T13

<400> SEQUENCE: 12

Lys Ala Pro Leu Val Pro Thr Gln Arg Glu Arg Gly Thr Lys Pro Pro
1 5 10 15

Leu Glu Glu Leu Ser Thr Ser Ala Thr Ser Asp His Asp His
20 25 30

<210> SEQ ID NO 13
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: tetrameric or monomeric Tn-OTS8 peptide
<220> FEATURE:
<221> NAME/KEY: MISC_FEATURE
<222> LOCATION: (4)..(4)
<223> OTHER INFORMATION: GalNAc
<220> FEATURE:
<221> NAME/KEY: MISC_FEATURE
<222> LOCATION: (14)..(14)
<223> OTHER INFORMATION: Biotin

<400> SEQUENCE: 13

Glu Arg Gly Thr Lys Pro Pro Leu Glu Glu Leu Ser Gly Lys
1 5 10

<210> SEQ ID NO 14
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: minimal epitope -epitope within the CA125 epitope of MUC16.

<400> SEQUENCE: 14

Phe Asn Thr Thr Glu Arg
1 5

<210> SEQ ID NO 15
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: epitope of MUC4

<400> SEQUENCE: 15

```
Ser Thr Gly Asp Thr Thr Pro Leu Pro Val Thr Asp Thr Ser Ser Val
1               5                   10                  15


<210> SEQ ID NO 16
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: glycosylation site of MUC4
<220> FEATURE:
<221> NAME/KEY: MISC_FEATURE
<222> LOCATION: (4)..(4)
<223> OTHER INFORMATION: GalNAc derivatization of T4

<400> SEQUENCE: 16

Gly His Ala Thr Pro Leu Pro Val Thr Asp
1               5                   10


<210> SEQ ID NO 17
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: 5E5 binding site on MUC1
<220> FEATURE:
<221> NAME/KEY: MISC_FEATURE
<222> LOCATION: (2)..(2)
<223> OTHER INFORMATION: GalNAc derivatization of T2
<220> FEATURE:
<221> NAME/KEY: MISC_FEATURE
<222> LOCATION: (13)..(13)
<223> OTHER INFORMATION: GalNAc derivatization of S13
<220> FEATURE:
<221> NAME/KEY: MISC_FEATURE
<222> LOCATION: (14)..(14)
<223> OTHER INFORMATION: GalNAc derivatization of T14

<400> SEQUENCE: 17

Val Thr Ser Ala Pro Asp Thr Arg Pro Ala Pro Gly Ser Thr Ala Pro
1               5                   10                  15

Pro Ala His Gly
            20


<210> SEQ ID NO 18
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: peptide tested for 237 CAR-T cell binding

<400> SEQUENCE: 18

Gly Thr Lys Pro Pro Leu Glu Glu
1               5


<210> SEQ ID NO 19
<211> LENGTH: 244
<212> TYPE: PRT
<213> ORGANISM: Artificial Sequence
<220> FEATURE:
<223> OTHER INFORMATION: Synthetic Polypeptide
<220> FEATURE:
```

-continued

<221> NAME/KEY: MISC_FEATURE
<223> OTHER INFORMATION: 237-wt scFv
<220> FEATURE:
<221> NAME/KEY: MISC_FEATURE
<223> OTHER INFORMATION: (1)-(111) 237 scFv Variable Light Region
<220> FEATURE:
<221> NAME/KEY: MISC_FEATURE
<223> OTHER INFORMATION: (112)-(126) Linker
<220> FEATURE:
<221> NAME/KEY: MISC_FEATURE
<223> OTHER INFORMATION: (127)-(244) scFv Variable Heavy Region

<400> SEQUENCE: 19

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Phe Cys Ser Gln Ser
                85                  90                  95

Thr His Val Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Gly Gly Leu Val Gln Pro Gly Gly Ser Met
    130                 135                 140

Lys Ile Phe Cys Ala Ala Ser Gly Phe Thr Phe Ser Asp Ala Trp Met
145                 150                 155                 160

Asp Trp Val Arg Gln Ser Pro Glu Lys Gly Leu Glu Trp Val Ala Glu
                165                 170                 175

Ile Arg Asn Lys Ala Asn Asn His Glu Thr Tyr Tyr Ala Glu Ser Val
            180                 185                 190

Lys Gly Arg Phe Thr Ile Thr Arg Asp Asp Ser Lys Ser Arg Met Ser
        195                 200                 205

Leu Gln Met Asn Ser Leu Arg Ala Glu Asp Thr Gly Ile Tyr Tyr Cys
    210                 215                 220

Ser Gly Gly Lys Val Arg Asn Ala Tyr Trp Gly Gln Gly Thr Thr Val
225                 230                 235                 240

Thr Val Ser Ser

<210> SEQ ID NO 20
<211> LENGTH: 244
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (98)..(99)
<223> OTHER INFORMATION: 237-WE scFv variant

<400> SEQUENCE: 20

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser

```
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Phe Cys Ser Gln Ser
                85                  90                  95

Thr Trp Glu Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Gly Gly Leu Val Gln Pro Gly Gly Ser Met
    130                 135                 140

Lys Ile Phe Cys Ala Ala Ser Gly Phe Thr Phe Ser Asp Ala Trp Met
145                 150                 155                 160

Asp Trp Val Arg Gln Ser Pro Glu Lys Gly Leu Glu Trp Val Ala Glu
                165                 170                 175

Ile Arg Asn Lys Ala Asn Asn His Glu Thr Tyr Tyr Ala Glu Ser Val
            180                 185                 190

Lys Gly Arg Phe Thr Ile Thr Arg Asp Asp Ser Lys Ser Arg Met Ser
        195                 200                 205

Leu Gln Met Asn Ser Leu Arg Ala Glu Asp Thr Gly Ile Tyr Tyr Cys
    210                 215                 220

Ser Gly Gly Lys Val Arg Asn Ala Tyr Trp Gly Gln Gly Thr Thr Val
225                 230                 235                 240

Thr Val Ser Ser


<210> SEQ ID NO 21
<211> LENGTH: 244
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (97)..(99)
<223> OTHER INFORMATION: 237-LGQ scFv variant

<400> SEQUENCE: 21

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Phe Cys Ser Gln Ser
                85                  90                  95

Leu Gly Gln Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
```

-continued

```
        115                 120                 125

Gln Leu Gln Gln Ser Gly Gly Gly Leu Val Gln Pro Gly Gly Ser Met
    130                 135                 140

Lys Ile Phe Cys Ala Ala Ser Gly Phe Thr Phe Ser Asp Ala Trp Met
145                 150                 155                 160

Asp Trp Val Arg Gln Ser Pro Glu Lys Gly Leu Glu Trp Val Ala Glu
                165                 170                 175

Ile Arg Asn Lys Ala Asn Asn His Glu Thr Tyr Tyr Ala Glu Ser Val
            180                 185                 190

Lys Gly Arg Phe Thr Ile Thr Arg Asp Asp Ser Lys Ser Arg Met Ser
        195                 200                 205

Leu Gln Met Asn Ser Leu Arg Ala Glu Asp Thr Gly Ile Tyr Tyr Cys
    210                 215                 220

Ser Gly Gly Lys Val Arg Asn Ala Tyr Trp Gly Gln Gly Thr Thr Val
225                 230                 235                 240

Thr Val Ser Ser


<210> SEQ ID NO 22
<211> LENGTH: 244
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (96)..(99)
<223> OTHER INFORMATION: 237-TNGK scFv variant

<400> SEQUENCE: 22

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Phe Cys Ser Gln Thr
                85                  90                  95

Asn Gly Lys Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Gly Gly Leu Val Gln Pro Gly Gly Ser Met
    130                 135                 140

Lys Ile Phe Cys Ala Ala Ser Gly Phe Thr Phe Ser Asp Ala Trp Met
145                 150                 155                 160

Asp Trp Val Arg Gln Ser Pro Glu Lys Gly Leu Glu Trp Val Ala Glu
                165                 170                 175

Ile Arg Asn Lys Ala Asn Asn His Glu Thr Tyr Tyr Ala Glu Ser Val
            180                 185                 190

Lys Gly Arg Phe Thr Ile Thr Arg Asp Asp Ser Lys Ser Arg Met Ser
        195                 200                 205

Leu Gln Met Asn Ser Leu Arg Ala Glu Asp Thr Gly Ile Tyr Tyr Cys
```

```
    210                 215                 220

Ser Gly Gly Lys Val Arg Asn Ala Tyr Trp Gly Gln Gly Thr Thr Val
225                 230                 235                 240

Thr Val Ser Ser


<210> SEQ ID NO 23
<211> LENGTH: 244
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (97)..(99)
<223> OTHER INFORMATION: 237-LGQ scFv variant

<400> SEQUENCE: 23

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Phe Cys Ser Gln Ser
                85                  90                  95

Leu Gly Gln Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Gly Gly Leu Val Gln Pro Gly Gly Ser Met
    130                 135                 140

Lys Ile Phe Cys Ala Ala Ser Gly Phe Thr Phe Ser Asp Ala Trp Met
145                 150                 155                 160

Asp Trp Val Arg Gln Ser Pro Glu Lys Gly Leu Glu Trp Val Ala Glu
                165                 170                 175

Ile Arg Asn Lys Ala Asn Asn His Glu Thr Tyr Tyr Ala Glu Ser Val
            180                 185                 190

Lys Gly Arg Phe Thr Ile Thr Arg Asp Asp Ser Lys Ser Arg Met Ser
        195                 200                 205

Leu Gln Met Asn Ser Leu Arg Ala Glu Asp Thr Gly Ile Tyr Tyr Cys
    210                 215                 220

Ser Gly Gly Lys Val Arg Asn Ala Tyr Trp Gly Gln Gly Thr Thr Val
225                 230                 235                 240

Thr Val Ser Ser


<210> SEQ ID NO 24
<211> LENGTH: 244
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (96)..(99)
<223> OTHER INFORMATION: 237-TNGK scFv variant
```

<400> SEQUENCE: 24

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Phe Cys Ser Gln Thr
                85                  90                  95

Asn Gly Lys Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Gly Gly Leu Val Gln Pro Gly Gly Ser Met
    130                 135                 140

Lys Ile Phe Cys Ala Ala Ser Gly Phe Thr Phe Ser Asp Ala Trp Met
145                 150                 155                 160

Asp Trp Val Arg Gln Ser Pro Glu Lys Gly Leu Glu Trp Val Ala Glu
                165                 170                 175

Ile Arg Asn Lys Ala Asn Asn His Glu Thr Tyr Tyr Ala Glu Ser Val
            180                 185                 190

Lys Gly Arg Phe Thr Ile Thr Arg Asp Asp Ser Lys Ser Arg Met Ser
        195                 200                 205

Leu Gln Met Asn Ser Leu Arg Ala Glu Asp Thr Gly Ile Tyr Tyr Cys
    210                 215                 220

Ser Gly Gly Lys Val Arg Asn Ala Tyr Trp Gly Gln Gly Thr Thr Val
225                 230                 235                 240

Thr Val Ser Ser

<210> SEQ ID NO 25
<211> LENGTH: 6996
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 237 CAR Sequence

<400> SEQUENCE: 25
tcaaggttag gaacagagag acaggagaat atgggccaaa caggatatct gtggtaagca      60
gttcctgccc cggctcaggg ccaagaacag ttggaacagc agaatatggg ccaaacagga     120
tatctgtggt aagcagttcc tgccccggct cagggccaag aacagatggt ccccagatgc     180
ggtcccgccc tcagcagttt ctagagaacc atcagatgtt tccagggtgc cccaaggacc     240
tgaaatgacc ctgtgcctta tttgaactaa ccaatcagtt cgcttctcgc ttctgttcgc     300
gcgcttctgc tccccgagct caataaaaga gcccacaacc cctcactcgg cgcgccagtc     360
ctccgattga ctgcgtcgcc cgggtacccg tattcccaat aaagcctctt gctgtttgca     420
tccgaatcgt ggactcgctg atccttggga gggtctcctc agattgattg actgcccacc     480

-continued

```
tcgggggtct ttcatttgga ggttccaccg agatttggag acccctgccc agggaccacc    540
gacccccccg ccgggaggta agctggccag cggtcgtttc gtgtctgtct ctgtctttgg    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg gggcccgtt ttgtggccca ttctgtatca gttaacctac    780
ccgagtcgga ctttttggag ctccgccact gtccgagggg tacgtggctt tgttgggga    840
cgagagacag agacacttcc cgccccccgtc tgaattttg ctttcggttt tacgccgaaa    900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc   1020
acttacaggc ggccgccacc atggggctgg tctgcatcat cctgtttctg gtggccacag   1080
ccaccggcgt gcacagcgat atccagctga cacagagccc cctgagcctg cctgtgtctc   1140
tgggcgatca ggccagcatc agctgcagat ccagccagag cctggtgcac agcaacggca   1200
acacctacct gcactggtat ctgcagaagc ccggccagag ccccaagctg ctgatctaca   1260
aggtgtccaa cagattcagc ggcgtgcccg acagattctc cggcagcggc tctggcaccg   1320
acttcaccct gaagatcagc tccgtggaag ccgaggacct gggcgtgtac ttctgcagcc   1380
agtccaccca cgtgcccaca ttcggcggag gcaccaagct ggaaatcaag ggcggaggcg   1440
gatctggcgg cggaggatct gggggaggcg gctctcaggt gcagctgcag cagtctggcg   1500
gagggctggt gcagcctggc ggcagcatga agatcttttg cgccgcctcc ggcttcacct   1560
tcagcgacgc ttggatggac tgggtgcgac agagccctga gaagggcctg gaatgggtgg   1620
ccgagatcag aaacaaggcc aacaaccacg agacttacta cgccgagagc gtgaagggca   1680
gattcaccat caccagggac gacagcaaga gcagaatgag cctgcagatg aacagcctga   1740
gggccgagga caccggcatc tactactgca gcggcggcaa agtgcggaac gcctactggg   1800
gccagggcac cacagtgacc gtgtccagcc tcgagaaagt gaacagcacc accaccaagc   1860
ccgtgctgag aacccctagc cctgtgcacc ctaccggcac atctcagcct cagaggcccg   1920
aggactgcag acctagaggc tccgtgaagg gaaccggcct ggacttcgcc tgtgacttct   1980
gggcactggt ggtggtggcc ggcgtgctgt tttgttacgg cctgctcgtg accgtggccc   2040
tgtgcgtgat ctggactagt aaatggatcc ggaagaagtt cccccacatc ttcaagcagc   2100
ccttcaagaa aaccaccggc gctgcccagg aagaggacgc ctgcagctgt aggtgccctc   2160
aggaagaaga aggcggaggg ggcggatacg agctgagagc caagttcagc agaagcgccg   2220
agacagccgc caacctgcag gaccctaacc agctgtacaa cgagctgaac ctgggcagac   2280
gggaagagta cgacgtgctg gaaaagaaga gagccaggga ccccgagatg ggcggcaagc   2340
agcagagaag aagaaacccc caggaaggcg tgtacaacgc cctgcagaaa gacaagatgg   2400
ccgaggccta cagcgagatc ggcaccaagg gcgaaaggcg gagaggcaag ggacacgacg   2460
gactgtacca gggcctgtcc accgccacca aggacacata cgatgccctg cacatgcaga   2520
cactcgcccc cagatgatga gaattcgagc atcttaccgc catttattcc catatttgtt   2580
ctgtttttct tgatttgggt atacatttaa atgttaataa aacaaaatgg tggggcaatc   2640
atttacattt tatgggatat gtaattacta gttcaggtgt attgccacaa gacaaacatg   2700
ttaagaaact ttcccgttat ttacgctctg ttcctgttaa tcaacctctg gattacaaaa   2760
tttgtgaaag attgactgat attcttaact atgttgctcc ttttacgctg tgtggatatg   2820
ctgctttaat gcctctgtat catgctattg cttcccgtac ggctttcgtt ttctcctcct   2880
```

```
tgtataaatc ctggttgctg tctctttatg aggagttgtg gcccgttgtc cgtcaacgtg   2940
gcgtggtgtg ctctgtgttt gctgacgcaa cccccactgg ctggggcatt gccaccacct   3000
gtcaactcct ttctgggact ttcgctttcc ccctcccgat cgccacggca gaactcatcg   3060
ccgcctgcct tgcccgctgc tggacagggg ctaggttgct gggcactgat aattccgtgg   3120
tgttgtcggg gaagctgacg tcctttccat ggctgctcgc ctgtgttgcc aactggatcc   3180
tgcgcgggac gtccttctgc tacgtccctt cggctctcaa tccagcggac ctcccttccc   3240
gaggccttct gccggttctg cggcctctcc cgcgtcttcg ctttcggcct ccgacgagtc   3300
ggatctccct ttgggccgcc tccccgcctg tttcgcctcg gcgtccggtc cgtgttgctt   3360
ggtcgtcacc tgtgcagaat tgcgaaccat ggattccacc gtgaactttg tctcctggca   3420
tgcaaatcgt caacttggca tgccaagaat taattcggat ccaagcttag gcctgctcgc   3480
tttcttgctg tcccatttct attaaaggtt cctttgttcc ctaagtccaa ctactaaact   3540
gggggatatt atgaagggcc ttgagcatct ggattctgcc tagcgctaag cttcctaaca   3600
cgagccatag atagaataaa agattttatt tagtctccag aaaaaggggg gaatgaaaga   3660
ccccacctgt aggtttggca agctagctta agtaagccat tttgcaaggc atggaaaaat   3720
acataactga gaatagagaa gttcagatca aggttaggaa cagagagaca ggagaatatg   3780
ggccaaacag gatatctgtg gtaagcagtt cctgccccgg ctcagggcca agaacagttg   3840
gaacagcaga atatgggcca aacaggatat ctgtggtaag cagttcctgc cccggctcag   3900
ggccaagaac agatggtccc cagatgcggt cccgccctca gcagtttcta gagaaccatc   3960
agatgtttcc agggtgcccc aaggacctga aatgaccctg tgccttattt gaactaacca   4020
atcagttcgc ttctcgcttc tgttcgcgcg cttctgctcc ccgagctcaa taaaagagcc   4080
cacaacccct cactcggcgc gccagtcctc cgatagactg cgtcgcccgg ggtacccgta   4140
ttcccaataa agcctcttgc tgtttgcatc cgaatcgtgg actcgctgat ccttgggagg   4200
gtctcctcag attgattgac tgcccacctc gggggtcttt cattctcgag agctttggcg   4260
taatcatggt catagctgtt tcctgtgtga aattgttatc cgctcacaat tccacacaac   4320
atacgagccg gaagcataaa gtgtaaagcc tggggtgcct aatgagtgag ctaactcaca   4380
ttaattgcgt tgcgctcact gcccgctttc cagtcgggaa acctgtcgtg ccagctgcat   4440
taatgaatcg gccaacgcgc ggggagaggc ggtttgcgta ttgggcgctc ttccgcttcc   4500
tcgctcactg actcgctgcg ctcggtcgtt cggctgcggc gagcggtatc agctcactca   4560
aaggcggtaa tacggttatc cacagaatca ggggataacg caggaaagaa catgtgagca   4620
aaaggccagc aaaaggccag gaaccgtaaa aaggccgcgt tgctggcgtt tttccatagg   4680
ctccgccccc ctgacgagca tcacaaaaat cgacgctcaa gtcagaggtg gcgaaacccg   4740
acaggactat aaagatacca ggcgtttccc cctggaagct ccctcgtgcg ctctcctgtt   4800
ccgaccctgc cgcttaccgg atacctgtcc gcctttctcc cttcgggaag cgtggcgctt   4860
tctcaatgct cacgctgtag gtatctcagt tcggtgtagg tcgttcgctc caagctgggc   4920
tgtgtgcacg aaccccccgt tcagcccgac cgctgcgcct tatccggtaa ctatcgtctt   4980
gagtccaacc cggtaagaca cgacttatcg ccactggcag cagccactgg taacaggatt   5040
agcagagcga ggtatgtagg cggtgctaca gagttcttga agtggtggcc taactacggc   5100
tacactagaa ggacagtatt tggtatctgc gctctgctga agccagttac cttcggaaaa   5160
agagttggta gctcttgatc cggcaaacaa accaccgctg gtagcggtgg tttttttgtt   5220
```

-continued tgcaagcagc agattacgcg cagaaaaaaa ggatctcaag aagatccttt gatcttttct 5280
acggggtctg acgctcagtg gaacgaaaac tcacgttaag ggattttggt catgagatta 5340
tcaaaaagga tcttcaccta gatcctttta aattaaaaat gaagttttaa atcaatctaa 5400
agtatatatg agtaaacttg gtctgacagt taccaatgct taatcagtga ggcacctatc 5460
tcagcgatct gtctatttcg ttcatccata gttgcctgac tccccgtcgt gtagataact 5520
acgatacggg agggcttacc atctggcccc agtgctgcaa tgataccgcg agacccacgc 5580
tcaccggctc cagatttatc agcaataaac cagccagccg gaagggccga gcgcagaagt 5640
ggtcctgcaa ctttatccgc ctccatccag tctattaatt gttgccggga agctagagta 5700
agtagttcgc cagttaatag tttgcgcaac gttgttgcca ttgctgctgg catcgtggtg 5760
tcacgctcgt cgtttggtat ggcttcattc agctccggtt cccaacgatc aaggcgagtt 5820
acatgatccc ccatgttgtg caaaaaagcg gttagctcct tcggtcctcc gatcgttgtc 5880
agaagtaagt tggccgcagt gttatcactc atggttatgg cagcactgca taattctctt 5940
actgtcatgc catccgtaag atgcttttct gtgactggtg agtactcaac caagtcattc 6000
tgagaatagt gtatgcggcg accgagttgc tcttgcccgg cgtcaatacg ggataatacc 6060
gcgccacata gcagaacttt aaaagtgctc atcattggaa aacgttcttc ggggcgaaaa 6120
ctctcaagga tcttaccgct gttgagatcc agttcgatgt aacccactcg tgcacccaac 6180
tgatcttcag catcttttac tttcaccagc gtttctgggt gagcaaaaac aggaaggcaa 6240
aatgccgcaa aaaagggaat aagggcgaca cggaaatgtt gaatactcat actcttcctt 6300
tttcaatatt attgaagcat ttatcagggt tattgtctca tgagcggata catatttgaa 6360
tgtatttaga aaaataaaca aataggggtt ccgcgcacat ttccccgaaa agtgccacct 6420
gacgtctaag aaaccattat tatcatgaca ttaacctata aaaataggcg tatcacgagg 6480
ccctttcgtc ttcaagctgc ctcgcgcgtt tcggtgatga cggtgaaaac ctctgacaca 6540
tgcagctccc ggagacggtc acagcttgtc tgtaagcgga tgccgggagc agacaagccc 6600
gtcagggcgc gtcagcgggt gttggcgggt gtcggggcgc agccatgacc cagtcacgta 6660
gcgatagtta ctatgcggca tcagagcaga ttgtactgag agtgcaccat atgcggtgtg 6720
aaataccgca cagatgcgta aggagaaaat accgcatcag gcgccattcg ccattcaggc 6780
tgcgcaactg ttgggaaggg cgatcggtgc gggcctcttc gctattacgc cagctggcga 6840
aagggggatg tgctgcaagg cgattaagtt gggtaacgcc agggttttcc cagtcacgac 6900
gttgtaaaac gacggccagt gaattagtac tctagcttaa gtaagccatt ttgcaaggca 6960
tggaaaaata cataactgag aatagagaag ttcaga 6996

<210> SEQ ID NO 26
<211> LENGTH: 6996
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: plasmid pMP71-237-CD28tm-41BB-CD3z
<220> FEATURE:
<221> NAME/KEY: misc_feature
<222> LOCATION: (1098)..(1835)
<223> OTHER INFORMATION: 237 scFV
<220> FEATURE:
<221> NAME/KEY: misc_feature
<222> LOCATION: (1836)..(1976)
<223> OTHER INFORMATION: CD8 linker
<220> FEATURE:

<221> NAME/KEY: misc_feature
<222> LOCATION: (1977)..(2060)
<223> OTHER INFORMATION: CD28 extracellular transmembrane region
<220> FEATURE:
<221> NAME/KEY: misc_feature
<222> LOCATION: (2061)..(2534)
<223> OTHER INFORMATION: 4-1BB

<400> SEQUENCE: 26

```
tcaaggttag gaacagagag acaggagaat atgggccaaa caggatatct gtggtaagca     60
gttcctgccc cggctcaggg ccaagaacag ttggaacagc agaatatggg ccaaacagga    120
tatctgtggt aagcagttcc tgccccggct cagggccaag aacagatggt ccccagatgc    180
ggtcccgccc tcagcagttt ctagagaacc atcagatgtt tccagggtgc cccaaggacc    240
tgaaatgacc ctgtgcctta tttgaactaa ccaatcagtt cgcttctcgc ttctgttcgc    300
gcgcttctgc tccccgagct caataaaaga gcccacaacc cctcactcgg cgcgccagtc    360
ctccgattga ctgcgtcgcc cgggtacccg tattcccaat aaagcctctt gctgtttgca    420
tccgaatcgt ggactcgctg atccttggga gggtctcctc agattgattg actgcccacc    480
tcgggggtct ttcatttgga ggttccaccg agatttggag acccctgccc agggaccacc    540
gaccccccccg ccgggaggta agctggccag cggtcgtttc gtgtctgtct ctgtctttgg    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg gggcccgtt ttgtggccca ttctgtatca gttaacctac    780
ccgagtcgga ctttttggag ctccgccact gtccgagggg tacgtggctt tgttggggga    840
cgagagacag agacacttcc cgcccccgtc tgaatttttg ctttcggttt tacgccgaaa    900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc   1020
acttacaggc ggccgccacc atggggctgg tctgcatcat cctgtttctg gtggccacag   1080
ccaccggcgt gcacagcgat atccagctga cacagagccc cctgagcctg cctgtgtctc   1140
tgggcgatca ggccagcatc agctgcagat ccagccagag cctggtgcac agcaacggca   1200
acacctacct gcactggtat ctgcagaagc ccggccagag ccccaagctg ctgatctaca   1260
aggtgtccaa cagattcagc ggcgtgcccg acagattctc cggcagcggc tctggcaccg   1320
acttcaccct gaagatcagc tccgtggaag ccgaggacct gggcgtgtac ttctgcagcc   1380
agtccaccca cgtgcccaca ttcggcggag gcaccaagct ggaaatcaag ggcggaggcg   1440
gatctggcgg cggaggatct gggggaggcg gctctcaggt gcagctgcag cagtctggcg   1500
gagggctggt gcagcctggc ggcagcatga agatcttttg cgccgcctcc ggcttcacct   1560
tcagcgacgc ttggatggac tgggtgcgac agagccctga gaagggcctg gaatgggtgg   1620
ccgagatcag aaacaaggcc aacaaccacg agacttacta cgccgagagc gtgaagggca   1680
gattcaccat caccagggac gacagcaaga gcagaatgag cctgcagatg aacagcctga   1740
gggccgagga caccggcatc tactactgca gcggcggcaa agtgcggaac gcctactggg   1800
gccagggcac cacagtgacc gtgtccagcc tcgagaaagt gaacagcacc accaccaagc   1860
ccgtgctgag aacccctagc cctgtgcacc ctaccggcac atctcagcct cagaggcccg   1920
aggactgcag acctagaggc tccgtgaagg gaaccggcct ggacttcgcc tgtgacttct   1980
gggcactggt ggtggtggcc ggcgtgctgt tttgttacgg cctgctcgtg accgtggccc   2040
tgtgcgtgat ctggactagt aaatggatcc ggaagaagtt cccccacatc ttcaagcagc   2100
```

```
ccttcaagaa aaccaccggc gctgcccagg aagaggacgc ctgcagctgt aggtgccctc   2160
aggaagaaga aggcggaggg ggcggatacg agctgagagc caagttcagc agaagcgccg   2220
agacagccgc caacctgcag gaccctaacc agctgtacaa cgagctgaac ctgggcagac   2280
gggaagagta cgacgtgctg gaaaagaaga gagccaggga ccccgagatg ggcggcaagc   2340
agcagagaag aagaaacccc caggaaggcg tgtacaacgc cctgcagaaa gacaagatgg   2400
ccgaggccta cagcgagatc ggcaccaagg gcgaaaggcg gagaggcaag ggacacgacg   2460
gactgtacca gggcctgtcc accgccacca aggacacata cgatgccctg cacatgcaga   2520
cactcgcccc cagatgatga gaattcgagc atcttaccgc catttattcc catatttgtt   2580
ctgtttttct tgatttgggt atacatttaa atgttaataa aacaaaatgg tggggcaatc   2640
atttacattt tatgggatat gtaattacta gttcaggtgt attgccacaa gacaaacatg   2700
ttaagaaact ttcccgttat ttacgctctg ttcctgttaa tcaacctctg gattacaaaa   2760
tttgtgaaag attgactgat attcttaact atgttgctcc ttttacgctg tgtggatatg   2820
ctgctttaat gcctctgtat catgctattg cttcccgtac ggctttcgtt ttctcctcct   2880
tgtataaatc ctggttgctg tctctttatg aggagttgtg gcccgttgtc cgtcaacgtg   2940
gcgtggtgtg ctctgtgttt gctgacgcaa cccccactgg ctggggcatt gccaccacct   3000
gtcaactcct ttctgggact ttcgctttcc ccctccccgat cgccacggca gaactcatcg   3060
ccgcctgcct tgcccgctgc tggacagggg ctaggttgct gggcactgat aattccgtgg   3120
tgttgtcggg gaagctgacg tcctttccat ggctgctcgc ctgtgttgcc aactggatcc   3180
tgcgcgggac gtccttctgc tacgtccctt cggctctcaa tccagcggac ctcccttccc   3240
gaggccttct gccggttctg cggcctctcc cgcgtcttcg ctttcggcct ccgacgagtc   3300
ggatctccct ttgggccgcc tccccgcctg tttcgcctcg gcgtccggtc cgtgttgctt   3360
ggtcgtcacc tgtgcagaat tgcgaaccat ggattccacc gtgaactttg tctcctggca   3420
tgcaaatcgt caacttggca tgccaagaat taattcggat ccaagcttag gcctgctcgc   3480
tttcttgctg tcccatttct attaaaggtt cctttgttcc ctaagtccaa ctactaaact   3540
gggggatatt atgaagggcc ttgagcatct ggattctgcc tagcgctaag cttcctaaca   3600
cgagccatag atagaataaa agattttatt tagtctccag aaaaaggggg gaatgaaaga   3660
ccccacctgt aggtttggca agctagctta agtaagccat tttgcaaggc atggaaaaat   3720
acataactga gaatagagaa gttcagatca aggttaggaa cagagagaca ggagaatatg   3780
ggccaaacag gatatctgtg gtaagcagtt cctgccccgg ctcagggcca agaacagttg   3840
gaacagcaga atatgggcca aacaggatat ctgtggtaag cagttcctgc cccggctcag   3900
ggccaagaac agatggtccc cagatgcggt cccgccctca gcagtttcta gagaaccatc   3960
agatgtttcc agggtgcccc aaggacctga aatgaccctg tgccttattt gaactaacca   4020
atcagttcgc ttctcgcttc tgttcgcgcg cttctgctcc ccgagctcaa taaaagagcc   4080
cacaacccct cactcggcgc gccagtcctc cgatagactg cgtcgcccgg ggtacccgta   4140
ttcccaataa agcctcttgc tgtttgcatc cgaatcgtgg actcgctgat ccttgggagg   4200
gtctcctcag attgattgac tgcccacctc gggggtcttt cattctcgag agctttggcg   4260
taatcatggt catagctgtt tcctgtgtga aattgttatc cgctcacaat tccacacaac   4320
atacgagccg gaagcataaa gtgtaaagcc tggggtgcct aatgagtgag ctaactcaca   4380
ttaattgcgt tgcgctcact gcccgctttc cagtcgggaa acctgtcgtg ccagctgcat   4440
```

-continued

```
taatgaatcg gccaacgcgc ggggagaggc ggtttgcgta ttgggcgctc ttccgcttcc   4500
tcgctcactg actcgctgcg ctcggtcgtt cggctgcggc gagcggtatc agctcactca   4560
aaggcggtaa tacggttatc cacagaatca ggggataacg caggaaagaa catgtgagca   4620
aaaggccagc aaaaggccag gaaccgtaaa aaggccgcgt tgctggcgtt tttccatagg   4680
ctccgccccc ctgacgagca tcacaaaaat cgacgctcaa gtcagaggtg gcgaaacccg   4740
acaggactat aaagatacca ggcgtttccc cctggaagct ccctcgtgcg ctctcctgtt   4800
ccgaccctgc cgcttaccgg atacctgtcc gcctttctcc cttcgggaag cgtggcgctt   4860
tctcaatgct cacgctgtag gtatctcagt tcggtgtagg tcgttcgctc caagctgggc   4920
tgtgtgcacg aaccccccgt tcagcccgac cgctgcgcct tatccggtaa ctatcgtctt   4980
gagtccaacc cggtaagaca cgacttatcg ccactggcag cagccactgg taacaggatt   5040
agcagagcga ggtatgtagg cggtgctaca gagttcttga agtggtggcc taactacggc   5100
tacactagaa ggacagtatt tggtatctgc gctctgctga agccagttac cttcggaaaa   5160
agagttggta gctcttgatc cggcaaacaa accaccgctg gtagcggtgg tttttttgtt   5220
tgcaagcagc agattacgcg cagaaaaaaa ggatctcaag aagatccttt gatcttttct   5280
acggggtctg acgctcagtg gaacgaaaac tcacgttaag ggattttggt catgagatta   5340
tcaaaaagga tcttcaccta gatcctttta aattaaaaat gaagttttaa atcaatctaa   5400
agtatatatg agtaaacttg gtctgacagt taccaatgct taatcagtga ggcacctatc   5460
tcagcgatct gtctatttcg ttcatccata gttgcctgac tccccgtcgt gtagataact   5520
acgatacggg agggcttacc atctggcccc agtgctgcaa tgataccgcg agacccacgc   5580
tcaccggctc cagatttatc agcaataaac cagccagccg gaagggccga gcgcagaagt   5640
ggtcctgcaa ctttatccgc ctccatccag tctattaatt gttgccggga agctagagta   5700
agtagttcgc cagttaatag tttgcgcaac gttgttgcca ttgctgctgg catcgtggtg   5760
tcacgctcgt cgtttggtat ggcttcattc agctccggtt cccaacgatc aaggcgagtt   5820
acatgatccc ccatgttgtg caaaaaagcg gttagctcct tcggtcctcc gatcgttgtc   5880
agaagtaagt tggccgcagt gttatcactc atggttatgg cagcactgca taattctctt   5940
actgtcatgc catccgtaag atgcttttct gtgactggtg agtactcaac caagtcattc   6000
tgagaatagt gtatgcggcg accgagttgc tcttgcccgg cgtcaatacg ggataatacc   6060
gcgccacata gcagaacttt aaaagtgctc atcattggaa aacgttcttc ggggcgaaaa   6120
ctctcaagga tcttaccgct gttgagatcc agttcgatgt aacccactcg tgcacccaac   6180
tgatcttcag catcttttac tttcaccagc gtttctgggt gagcaaaaac aggaaggcaa   6240
aatgccgcaa aaaagggaat aagggcgaca cggaaatgtt gaatactcat actcttcctt   6300
tttcaatatt attgaagcat ttatcagggt tattgtctca tgagcggata catatttgaa   6360
tgtatttaga aaaataaaca aataggggtt ccgcgcacat ttccccgaaa agtgccacct   6420
gacgtctaag aaaccattat tatcatgaca ttaacctata aaaataggcg tatcacgagg   6480
ccctttcgtc ttcaagctgc ctcgcgcgtt tcggtgatga cggtgaaaac ctctgacaca   6540
tgcagctccc ggagacggtc acagcttgtc tgtaagcgga tgccgggagc agacaagccc   6600
gtcagggcgc gtcagcgggt gttggcgggt gtcggggcgc agccatgacc cagtcacgta   6660
gcgatagtta ctatgcggca tcagagcaga ttgtactgag agtgcaccat atgcggtgtg   6720
aaataccgca cagatgcgta aggagaaaat accgcatcag gcgccattcg ccattcaggc   6780
tgcgcaactg ttgggaaggg cgatcggtgc gggcctcttc gctattacgc cagctggcga   6840
```

```
aagggggatg tgctgcaagg cgattaagtt gggtaacgcc agggttttcc cagtcacgac   6900

gttgtaaaac gacggccagt gaattagtac tctagcttaa gtaagccatt ttgcaaggca   6960

tggaaaaata cataactgag aatagagaag ttcaga                             6996


<210> SEQ ID NO 27
<211> LENGTH: 244
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (98)..(98)
<223> OTHER INFORMATION: 237 wt- H98W variant

<400> SEQUENCE: 27

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Phe Cys Ser Gln Ser
                85                  90                  95

Thr Trp Val Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Gly Gly Leu Val Gln Pro Gly Gly Ser Met
    130                 135                 140

Lys Ile Phe Cys Ala Ala Ser Gly Phe Thr Phe Ser Asp Ala Trp Met
145                 150                 155                 160

Asp Trp Val Arg Gln Ser Pro Glu Lys Gly Leu Glu Trp Val Ala Glu
                165                 170                 175

Ile Arg Asn Lys Ala Asn Asn His Glu Thr Tyr Tyr Ala Glu Ser Val
            180                 185                 190

Lys Gly Arg Phe Thr Ile Thr Arg Asp Asp Ser Lys Ser Arg Met Ser
        195                 200                 205

Leu Gln Met Asn Ser Leu Arg Ala Glu Asp Thr Gly Ile Tyr Tyr Cys
    210                 215                 220

Ser Gly Gly Lys Val Arg Asn Ala Tyr Trp Gly Gln Gly Thr Thr Val
225                 230                 235                 240

Thr Val Ser Ser


<210> SEQ ID NO 28
<211> LENGTH: 244
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (99)..(99)
<223> OTHER INFORMATION: 237 wt- V99E variant
```

<400> SEQUENCE: 28

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Phe Cys Ser Gln Ser
                85                  90                  95

Thr His Gln Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Gly Gly Leu Val Gln Pro Gly Gly Ser Met
    130                 135                 140

Lys Ile Phe Cys Ala Ala Ser Gly Phe Thr Phe Ser Asp Ala Trp Met
145                 150                 155                 160

Asp Trp Val Arg Gln Ser Pro Glu Lys Gly Leu Glu Trp Val Ala Glu
                165                 170                 175

Ile Arg Asn Lys Ala Asn Asn His Glu Thr Tyr Tyr Ala Glu Ser Val
            180                 185                 190

Lys Gly Arg Phe Thr Ile Thr Arg Asp Asp Ser Lys Ser Arg Met Ser
        195                 200                 205

Leu Gln Met Asn Ser Leu Arg Ala Glu Asp Thr Gly Ile Tyr Tyr Cys
    210                 215                 220

Ser Gly Gly Lys Val Arg Asn Ala Tyr Trp Gly Gln Gly Thr Thr Val
225                 230                 235                 240

Thr Val Ser Ser

<210> SEQ ID NO 29
<211> LENGTH: 113
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: 5E5 Variable Light Region

<400> SEQUENCE: 29

Glu Leu Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn

```
                85                  90                  95

Asp Tyr Ser Tyr Pro Leu Thr Phe Gly Ala Gly Thr Lys Leu Glu Leu
            100                 105                 110

Lys
```

<210> SEQ ID NO 30
<211> LENGTH: 117
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: 5E5 Variable Heavy Region

<400> SEQUENCE: 30

```
Gln Val Gln Leu Gln Gln Ser Asp Ala Glu Leu Val Lys Pro Gly Ser
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly His Phe Ser Pro Gly Asn Thr Asp Ile Lys Tyr Asn Asp Lys Phe
    50                  55                  60

Lys Gly Lys Ala Thr Leu Thr Val Asp Arg Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Thr Ser Thr Phe Phe Phe Asp Tyr Trp Gly Gln Thr Thr Leu Thr
            100                 105                 110

Val Ser Ser Gly Ser
        115
```

<210> SEQ ID NO 31
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: wild-type PDPN binding site for the 237 antibody

<400> SEQUENCE: 31

```
Gly Thr Lys Pro Pro Leu Glu Glu
1               5
```

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32

```
gatattgtga ccccaggtac                                                  20
```

<210> SEQ ID NO 33
<211> LENGTH: 22
<212> TYPE: DNA
<213> ORGANISM: Artificial Sequence
<220> FEATURE:

-continued

<223> OTHER INFORMATION: Synthetic Polynucleotide

<400> SEQUENCE: 33
caccgggaca cattaggatt gg 22

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 34
cggccacgga accagcttca 20

<210> SEQ ID NO 35
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (2)..(2)
<223> OTHER INFORMATION: Tn modified

<400> SEQUENCE: 35

Gly Thr Lys Pro Pro Leu Glu Glu
1 5

<210> SEQ ID NO 36
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 36

Ala Pro Leu Val Pro Thr Gln Arg Glu Arg Gly
1 5 10

<210> SEQ ID NO 37
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 37

Ser Thr Ala Pro Pro Ala His Gly
1 5

<210> SEQ ID NO 38
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 38

Glu Thr Pro His Ala Thr Ser His
1 5

<210> SEQ ID NO 39
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 39

Ser Thr Pro Pro Ser Val Thr Ser
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 40

Ser Thr Gln Pro Thr Ser Thr Val
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 41

Thr Thr Ala Pro Pro Ala Pro Pro
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 42

Ser Thr Lys Ala Glu His Leu Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 43

Thr Thr Ser Ile Thr Ser Asp Pro
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 44

Thr Thr Ala Val Thr Pro Asn Gly
1               5

<210> SEQ ID NO 45
<211> LENGTH: 8
<212> TYPE: PRT
<213> ORGANISM: Artificial Sequence
<220> FEATURE:

<223> OTHER INFORMATION: Synthetic Polypeptide

<400> SEQUENCE: 45

Gly Thr Glu Ser Pro Val Arg Glu
1 5

<210> SEQ ID NO 46
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 46

His Ser Asn Gly Asn Thr Tyr
1 5

<210> SEQ ID NO 47
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(4)
<223> OTHER INFORMATION: Xaa can be any naturally occurring amino acid

<400> SEQUENCE: 47

Xaa Xaa Xaa Xaa Asn Thr Tyr
1 5

<210> SEQ ID NO 48
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(7)
<223> OTHER INFORMATION: Xaa can be any naturally occurring amino acid

<400> SEQUENCE: 48

His Ser Asn Xaa Xaa Xaa Xaa
1 5

<210> SEQ ID NO 49
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 49

Ser Thr His Val
1

<210> SEQ ID NO 50
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(4)
<223> OTHER INFORMATION: Xaa can be any naturally occurring amino acid

<400> SEQUENCE: 50

Xaa Xaa Xaa Xaa
1

<210> SEQ ID NO 51
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 51

Glu Ile Arg Asn Lys Ala Asn Asn His Glu
1 5 10

<210> SEQ ID NO 52
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(4)
<223> OTHER INFORMATION: Xaa can be any naturally occurring amino acid

<400> SEQUENCE: 52

Xaa Xaa Xaa Xaa Lys Ala Asn Asn His Glu
1 5 10

<210> SEQ ID NO 53
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(7)
<223> OTHER INFORMATION: Xaa can be any naturally occurring amino acid

<400> SEQUENCE: 53

Glu Ile Arg Xaa Xaa Xaa Xaa Asn His Glu
1 5 10

<210> SEQ ID NO 54
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(10)
<223> OTHER INFORMATION: Xaa can be any naturally occurring amino acid

<400> SEQUENCE: 54

Glu Ile Arg Asn Lys Ala Xaa Xaa Xaa Xaa
1 5 10

<210> SEQ ID NO 55
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 55

-continued

Glu Arg Gly Thr Lys Pro Pro Leu Glu Glu Leu Ser
1 5 10

<210> SEQ ID NO 56
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 56

Ala Thr Lys Pro Pro Leu Glu Glu
1 5

<210> SEQ ID NO 57
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 57

Gly Thr Ala Pro Pro Leu Glu Glu
1 5

<210> SEQ ID NO 58
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 58

Gly Thr Lys Ala Pro Leu Glu Glu
1 5

<210> SEQ ID NO 59
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 59

Gly Thr Lys Pro Ala Leu Glu Glu
1 5

<210> SEQ ID NO 60
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 60

Gly Thr Lys Pro Pro Ala Glu Glu
1 5

<210> SEQ ID NO 61
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 61

Gly Thr Lys Pro Pro Leu Ala Glu 1 5

<210> SEQ ID NO 62
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 62

Gly Thr Lys Pro Pro Leu Glu Ala
1 5

<210> SEQ ID NO 63
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 63

Gly Thr Lys Pro Pro Leu Glu Glu
1 5

<210> SEQ ID NO 64
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 64

Gly Thr Lys Pro Pro Leu Ala
1 5

<210> SEQ ID NO 65
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 65

Gly Thr Lys Pro Ala Ala Ala
1 5

<210> SEQ ID NO 66
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 66

Gly Thr Lys Ala Ala Ala Ala
1 5

<210> SEQ ID NO 67
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 67

Gly Thr Ala Ala Ala Ala Ala
1 5

<210> SEQ ID NO 68
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 68

Ala Thr Ala Ala Ala Ala Ala
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 69

Gly Thr Lys Ala Ala Ala
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 70

Gly Thr Lys Ala Ala
1               5

<210> SEQ ID NO 71
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 71

Gly Thr Lys Ala
1

<210> SEQ ID NO 72
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 72

Gly Thr Lys Pro Pro Leu Glu Glu Leu
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: mod_res
<222> LOCATION: (2)..(2)
<223> OTHER INFORMATION: Tn Modified

<400> SEQUENCE: 73

Gly Thr Glu Ser Pro Val Arg Glu
1 5

<210> SEQ ID NO 74
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: mod_res
<222> LOCATION: (2)..(2)
<223> OTHER INFORMATION: Tn Modified

<400> SEQUENCE: 74

Ser Thr Ala Pro Pro Ala His Gly
1 5

<210> SEQ ID NO 75
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: mod_res
<222> LOCATION: (2)..(2)
<223> OTHER INFORMATION: Tn modified

<400> SEQUENCE: 75

Ser Thr Pro Pro Ser Val Thr Ser
1 5

<210> SEQ ID NO 76
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (2)..(2)
<223> OTHER INFORMATION: Tn Modified

<400> SEQUENCE: 76

Ser Thr Lys Ala Glu His Leu Thr
1 5

<210> SEQ ID NO 77
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: mod_res
<222> LOCATION: (2)..(2)
<223> OTHER INFORMATION: Tn Modified

<400> SEQUENCE: 77

Glu Thr Ser Lys Gly Thr Ser Gly
1 5

<210> SEQ ID NO 78
<211> LENGTH: 8
<212> TYPE: PRT
<213> ORGANISM: Artificial Sequence
<220> FEATURE:
<223> OTHER INFORMATION: Synthetic Polypeptide -continued
<220> FEATURE:
<221> NAME/KEY: mod_res
<222> LOCATION: (2)..(2)
<223> OTHER INFORMATION: mod_res

<400> SEQUENCE: 78

Ser Thr Gln Pro Thr Ser Thr Val
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (2)..(2)
<223> OTHER INFORMATION: Tn Modified

<400> SEQUENCE: 79

Gly Thr Ser Ala Ser Leu Val Tyr
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Tn Modified

<400> SEQUENCE: 80

Thr Thr Ala Pro Pro Ala Pro Pro
1               5

CANCER TREATMENT WITH 237 CAR-T CELL BASED THERAPEUTICS RECOGNIZING THE Tn EPITOPE

CROSS-REFERENCE TO RELATED APPLICATIONS

This application is a national phase application under 35 U.S.C. § 371 of International Application No. PCT/US2019/050652 filed Sep. 11, 2019, which claims the benefit of priority of U.S. Provisional Patent Application No. 62/729,951, filed Sep. 11, 2018. The entire contents of each of the above-referenced disclosures are specifically incorporated herein by reference in their entirety.

STATEMENT OF GOVERNMENT SUPPORT

This invention was made with government support under grant numbers CA022677 and CA037156 awarded by the National Institutes of Health. The government has certain rights in the invention.

INCORPORATION BY REFERENCE OF MATERIAL SUBMITTED ELECTRONICALLY

The instant application contains a Sequence Listing which has been submitted in ASCII format and is hereby incorporated by reference in its entirety. Said ASCII copy, created on Mar. 9, 2021, is named ARCD.P0706US_ Sequence_Listing.txt and is 57,961 bytes in size.

FIELD

The disclosure relates generally to the fields of cancer biology and to molecular antibody-receptor technology.

BACKGROUND

Cancer is a significant threat to human and non-human animal health, often leading to death or a reduced quality of life. The burden placed on healthcare organizations to treat and prevent the various forms of cancer requires considerable resources and manpower. One of the main weapons vertebrates, including humans, have to combat disease is a functioning immune system. Although focused on foreign, or non-self, materials, advances in immunology show promise in being able to harness the immune system and direct its potent protective abilities against deleterious "self" materials such as cancer cells.

Mutant antigens are powerful targets for tumor destruction, e.g., in mice, and tumor-infiltrating lymphocytes targeting these mutations cause durable tumor regression in patients. Nevertheless, non-mutant antigens have been presumed by many scientists to be cancer-specific or "relatively cancer-specific" and safe antigens for vaccine approaches. Adoptively transferred T cells, however, can be orders of magnitude more effective and destructive than vaccinations. As a result, targeting MAGE-A3, HER-2 or CEA with T cells has caused death or serious toxicity in clinical trials now halted (8-11). As was shown in 2002, cancer cells with extremely high or very low expression levels of a target antigen differ only in the induction of immune responses, not in the effector phase (15).

A 1995 report (6) established that somatic tumor-specific mutations resulting in mutant peptides yield unique antigens that are recognized by tumor-specific T cells. This was subsequently confirmed by many independent laboratories in studies on human and mice (e.g., 23-25). In those studies, it was shown that the unique immunodominant antigen on the UV-induced tumor 8101 was caused by a single base-pair substitution in the p68 oncogenic RNA helicase, a critical microRNA regulator protein (26-28).

Non-mutant antigens can nevertheless be cancer-specific antigens and safe targets for adoptive T cell transfer, and this realization involves a shift in focus from previous work caused by the discovery that Tn-O-glycopeptides occur as cancer-specific antigens (16). Tn-antigens are a unique class of cancer-specific neoantigens that arise due to mutations in the cellular glycosylation machinery, leading to abnormal glycosylation of surface proteins on cancer cells. Tn antigen (1, 2) is expressed by a majority of common cancers of diverse origin and it is one of the earliest antigens identified on human tumors (18-20). Antibodies that specifically bind only Tn are usually IgM and are expected to be of limited use, i.e., for histochemistry, but not for CARs. Occasional IgG-class anti-Tn antibodies are of poor specificity and affinity and may slightly delay the outgrowth of Tn-expressing transplanted cancer cells when used in animals (54, 55).

It is likely that about 70-90% of common human cancers, such as breast, colon, prostate, ovary, lung, bladder and cervix cancers, express Tn (12). Conflicting data on the magnitude of expression of Tn on human tumors (56) can be largely explained by differences in affinities of the large number of different antibodies that have been experimentally produced, most of them of poor quality (with very few exceptions such as the IgM 5F4). Apparently, it is difficult for the epitope binding site of antibodies to bind the single sugar molecule with high affinity and specificity. While Thomsen-Friedenreich (TF) antigen is an oncofetal antigen highly expressed in the embryo and fetus (57), there is less evidence that Tn is also an oncofetal antigen (12), even though Tn antigens have been reported to be expressed perinatally in the brain but rapidly declining after birth (58). Most adults naturally have anti-Tn as well as anti-TF antibodies, consistent with antigenic stimulation by Tn and TF antigens expressed by the bacterial flora (13, 14); Tn antigen is also expressed on HIV-1 and pathogenic parasites (12).

Even though Tn was discovered by Dausset half a century ago (2) and Tn expression on cancer cells over 40 years ago (18-21), technological advances that allowed the sophistication and rapid expansion of glyco-chemistry and glycobiology were only made in the last decade. There are still huge defects in the understanding of this field. As a further point on specificity, there is longstanding evidence for tolerance to many cancer testis antigens, HER-2 and CEA, indicating their expression on normal tissues and ultimately absence of true cancer specificity. By contrast, Tn-O-glycopeptides consistently have given the opposite result.

Most human cancers lack specific antigens that are predictably present and serve as effective targets for eradication by T cells. Every cancer cell type harbors a unique set of mutations resulting in different tumor-specific antigens. Identifying an effective unique antigen and isolating an appropriate T cell receptor (TCR) for transduction of autologous T cells for adoptive immunotherapy is still difficult despite the enormous technological progress being made. Adoptive immunotherapy using antibodies or T cells is clinically as well as experimentally the most effective immunotherapy, at least when clinically relevant cancers are considered (22).

Substantial experimental and clinical evidence indicates that the specificity of an antibody predicts the reactivity of the cognate CAR. For example, anti-CD19 CART cells mimic the reactivity of the anti-CD19 antibody. While adoptive transfer of anti-CD19 CART cells effectively treated patients with advanced drug- and radiation-resistant CD19-positive B cell malignancies, the loss of CD19 from the cancer cell surface is a common cause of relapse (143).

The 237 monoclonal antibody is an example of an antibody that recognizes a Tn antigen (or, a terminal GalNAc residue) on the OTS8 peptide, a 7-amino-acid epitope peptide found in the Podoplanin protein (referred to as Tn-OTS8 or Tn-Podoplanin). OTS8 is expressed on the surface of the Ag104A murine cancer cell line (60). The Tn antigen arises due to a mutation in the COSMC protein that is a chaperone for a galactose transferase that extends the terminal GalNAc as part of the O-linked glycosylation of OTS8 protein (16, 102, 124). In addition to binding to the Tn (GalNAc) on OTS8, the 237 antibody also interacts with side chains of OTS8 residues surrounding the Tn, thus providing an additional element to control specificity of the interaction (3).

There remains a need, however, to identify shared, yet tumor-specific, antigens on a wide range of solid tumors, and a concomitant need to develop prophylactics and therapeutics that can diagnose, prevent, treat or ameliorate a symptom of these cancers, along with methods for diagnosing, preventing and treating various cancers.

In this disclosure, it is shown that the 237 antibody selectively binds to COSMC-mutant cancer cells expressing murine Tn-podoplanin, while the 237 CAR-T cell surprisingly cross-reacts with many different human cancers and recognizes several different Tn-glycopeptides.

SUMMARY

The disclosure provides materials and methods for treating or ameliorating a symptom of cancer, or for identifying patient sub-populations amenable to the type of anti-cancer therapy disclosed herein, that takes advantage of improved beneficial properties engineered into biologics, such as single-chain variable antibody fragments (scFvs) and chimeric antigen receptors (CARs), that specifically target cancer cells with great specificity and efficiently identify and/or destroy those cancer cells while avoiding unacceptable toxicity concerns. The technology involves scFvs targeting cancer-specific antigens, or CARs on the surface of T cells targeting such cancer-specific antigens, i.e., CAR-T cell therapy, as well as the related Bispecific T cell Engager (BiTE) technology. The technology is based on the 237 monoclonal antibody that recognizes the modified protein glycosylation pattern understood in the art as constituting the Tn epitope (10, 59). The disclosure reveals that the binding domains of the 237 antibody have been incorporated into yeast display, CAR-T cells, BiTEs, and in soluble form. The soluble form of 237 scFv has been further engineered to provide a multimeric (e.g., tetrameric) form exhibiting surprisingly increased sensitivity for the Tn epitope. The yeast-displayed form has been engineered to provide derivatives of unexpectedly increased affinity for the Tn epitope, and derivatives exhibiting altered Tn epitope specificities that were not anticipated. The Tn-specific 237 scFv formats disclosed herein thus demonstrate three significant and unexpected improvements relative to the 237 antibody. First, greater sensitivity has been obtained by engineering and expressing soluble 237 scFvs that form multimers, such as tetramers. Second, 237 scFv derivatives disclosed herein have been engineered and screened using yeast display have yielded 237 scFv derivatives exhibiting increased affinity for the Tn epitope relative to the 237 antibody, and this increased affinity is significant in achieving efficacious adoptive immunotherapies to treat cancer using CARs and soluble therapeutics such as BiTEs. Third, scFv derivatives exhibiting altered Tn specificities relative to the 237 antibody are disclosed herein, wherein the Tn specificity is for the GalNAc moiety, with fewer restrictions on the associated amino acid sequence, leading to broader targeting of the Tn epitope on various cancer cells. The surprising benefits are valuable features of all forms of the compositions disclosed herein. In particular, the increased sensitivity of the compositions is important for soluble compositions such as BiTEs, which function best with affinities in the low nanomolar or picomolar range.

Ideally, a cancer cell target is cancer-specific and cannot be lost so the cancer cannot escape when being targeted. Instead of using a single driver mutation as a target, the disclosure provides a CAR that simultaneously targets multiple independent cancer-specific epitopes on a single cancer cell.

The disclosure reveals mutations in the chaperone COSMC that are cancer-specific mutations occurring in about 1-3% of human cancers that include a wide variety of cancer types. Cosmc mutations are embryologically lethal and are not found in healthy tissues. Mutational loss of COSMC function, such as from a somatic mutation, results in the simultaneous appearance of numerous Tn-glycopeptide epitopes on the outer cancer cell membrane. These cancer-specific epitopes are positioned on several independent cell-surface molecules on every cancer cell carrying this mutation.

Although mutational loss of COSMC function is not an essential driver mutation, escape cannot occur because this would require the cancer cell to repair the mutation or simultaneously lose multiple surface proteins targeted by the single CAR. Both types of escape are extremely unlikely. Consistent with this position is the fact that escape has never been observed in advanced human cancers in NSG (NOD, scid (prkdc$^-$), Gamma (γ chain of IL2 receptor, or IL2rg)) mice after using the CAR therapy disclosed herein.

The data disclosed herein strongly establishes that the CAR made from the 237 scFv is Cosmc mutation-specific, but recognizes multiple different Tn-glycopeptides on multiple surface molecules. Similarly, the multimers made from the soluble 237 scFv form recognize multiple different Tn-glycopeptides on multiple surface molecules beyond recognition of the Tn-antigen of Podoplanin alone. By contrast, the antibody from which the CAR was made only recognizes a murine Tn-glycosylated protein (Podoplanin) due to its lower sensitivity than the CAR or the multimers. Accordingly, the cancer-specific CAR disclosed herein represents a significant advance in the diagnosis, prognosis and treatment of cancer in animals including humans, as well as providing material useful in identifying subsets of cancer subjects amenable to anti-cancer immunotherapy. The effectiveness and versatility of the anti-cancer CAR disclosed herein leads to the several aspects of the disclosure presented below.

In one aspect, the disclosure provides a chimeric antigen receptor (CAR) that specifically binds a Tn glycopeptide comprising: (a) a single chain variable fragment (scFv) that specifically binds a Tn glycopeptide, wherein the scFv comprises a heavy chain complementarity determining region 1 (CDRH1) sequence at positions 150-159 of SEQ ID NO:19, a CDRH2 sequence at positions 177-186 of SEQ ID NO:19, a CDRH3 sequence at positions 227-232 of SEQ ID NO:19, a light chain complementarity determining region 1 (CDRL1) at positions 26-37 of SEQ ID NO:19, a CDRL2 at positions 55-57 of SEQ ID NO:19, and a variant of the CDRL3 sequence at positions 96-100 of SEQ ID NO:19 comprising at least one amino acid variation from the wild-type antibody 237 light chain complementarity determining region 3 sequence at positions 96-100 of SEQ ID NO:19; and (b) a T-cell signaling domain. In some embodiments, the chimeric antigen receptor comprises a scFv that is a variant of the wild-type scFv of antibody 237 comprising at least one amino acid variation from the wild-type antibody 237 light chain complementarity determining region 3 sequence at positions 96-100 of SEQ ID NO:19. In some embodiments, the CAR specifically binds a cancer-specific Tn glycopeptide. In some embodiments, the scFv is soluble. In some embodiments, a nanomolar concentration of the CAR detectably binds a Tn epitope or exhibits detectable binding to a target Tn epitope that is not detectably bound by the wild-type 237 CAR at a nanomolar concentration. In some embodiments, the CAR detectably binds to a Tn antigen with a $K_D$ value less than 100 nM. In some embodiments, the CAR comprises an antibody 237 light chain complementarity determining region 3 sequence of positions 96-100 of SEQ ID NO: 27. In some embodiments, the CAR comprises an antibody 237 light chain complementarity determining region 3 sequence of positions 96-100 of SEQ ID NO: 28. In some embodiments, the CAR comprises an antibody 237 light chain complementarity determining region 3 sequence of positions 96-100 of SEQ ID NO: 20. In some embodiments, the CAR comprises a light chain complementarity determining region 3 (CDRL3) sequence of TTWAP (SEQ ID NO: 3), STWAP (SEQ ID NO: 4), STWSP (SEQ ID NO: 5), STWGP (SEQ ID NO: 6), STWQP (SEQ ID NO: 7), STWEP (SEQ ID NO: 8), or SVWEP (SEQ ID NO: 9). In some embodiments, the CAR has a $K_D$ for Tn-Podoplanin of less than 100 nM. In some embodiments, the T-cell signaling domain is CD3ζ or FcRγ. In some embodiments, the FcRγ is FcεRγ. In some embodiments, the CAR comprising FcεRγ further comprising a CD28 transmembrane region, an ICOS transmembrane region, 4-1BB, or OX-40. In some embodiments, the chimeric antigen receptor comprises the CD28 transmembrane region, and further comprises 4-1BB, OX-40, or Lck. In some embodiments, the 237 scFv variant exhibits a greater sensitivity to a Tn epitope than the wild-type 237 scFv. In some embodiments, the 237 scFv variant exhibits a broader therapeutic range in treating cancer than the wild-type 237 scFv. In some embodiments, the CAR comprises the sequence set forth in SEQ ID NOs:21, 22, 23 or 24.

In another aspect, the disclosure provides a soluble cancer-specific 237 single chain variable fragment (scFv) that specifically binds a Tn glycopeptide comprising a heavy chain complementarity determining region 1 (CDRH1) sequence at positions 150-159 of SEQ ID NO:19, a CDRH2 sequence at positions 177-186 of SEQ ID NO:19, a CDRH3 sequence at positions 227-232 of SEQ ID NO:19, a light chain complementarity determining region 1 (CDRL1) at positions 26-37 of SEQ ID NO:19, a CDRL2 at positions 55-57 of SEQ ID NO:19, and a variant of the CDRL3 sequence at positions 96-100 of SEQ ID NO:19 comprising at least one amino acid variation from the wild-type antibody 237 light chain complementarity determining region 3 sequence at positions 96-100 of SEQ ID NO:19. In some embodiments, the scFv is a variant of the wild-type scFv of antibody 237 comprising the heavy chain variable region amino acid sequence at positions 127-244 of SEQ ID NO:19 and a variant of the light chain variable region amino acid sequence at positions 1-111 of SEQ ID NO:19, wherein the variation comprises at least one amino acid variation from the wild-type antibody 237 light chain complementarity determining region 3 sequence at positions 96-100 of SEQ ID NO:19. In some embodiments, a nanomolar concentration of the 237 scFv variant detectably binds a Tn epitope or exhibits detectable binding to a target Tn epitope that is not detectably bound by the wild-type 237 scFv at a nanomolar concentration. In some embodiments, the 237 scFv variant is a multimer, such as a tetramer. In some embodiments, the scFv multimerizes to a form that detectably binds to Tn antigen with a $K_D$ value less than 100 nM. In some embodiments, the 237 scFv variant comprises a tryptophan substitution for a histidine residue at position 98 of SEQ ID NO:27 in the complementarity determining region 3 (CDRL3) of the antibody 237 light chain variable region. In some embodiments, the scFv variant comprises a glutamate substitution for a valine residue at position 99 of SEQ ID NO:28 in the complementarity determining region 3 (CDRL3) domain of the antibody 237 light chain variable region. In some embodiments, the scFv variant comprising the glutamate substitution for valine at position 99 of SEQ ID NO:28 in the complementarity determining region 3 9CDRL3) further comprises a tryptophan substitution for a histidine residue at position 98 of SEQ ID NO:20 in the complementarity determining region 3 (CDRL3) of the antibody 237 light chain variable region. In some embodiments, the scFv variant comprises a light chain complementarity determining region 3 (CDRL3) sequence of TTWAP (SEQ ID NO:3), STWAP (SEQ ID NO:4), STWSP (SEQ ID NO:5), STWGP (SEQ ID NO:6), STWQP (SEQ ID NO:7), STWEP (SEQ ID NO:8), or SVWEP (SEQ ID NO:9). In some embodiments, the scFv variant exhibits a greater sensitivity to a Tn epitope than the wild-type 237 scFv, such as wherein the 237 scFv variant has a $K_D$ for Tn-Podoplanin of less than 100 nM. In some embodiments, the scFv variant exhibits a broader therapeutic range in treating cancer than the wild-type 237 scFv.

Another aspect of the disclosure is drawn to a method of identifying a subject as a cancer patient amenable to anti-Tn epitope cancer therapy comprising (a) determining if there is a mutation in the cosmc gene of the subject; and (b) identifying the subject as a cancer patient amenable to anti-Tn epitope cancer therapy if the subject harbors a mutant cosmc gene. In some embodiments, the mutation is determined by sequencing at least a portion of the cosmc gene of the subject. Any cosmc mutation that results in a lower level of COSMC activity is contemplated, including insertions, deletions, rearrangements, and point mutations, including missense and nonsense mutations. Moreover, the disclosure comprehends mutant cosmc that contain one or more discrete mutations relative to wild-type cosmc. In some embodiments, a nucleic acid comprising the cosmc gene is amplified. In some embodiments, the amplification is achieved using a polymerase chain reaction or reverse transcription polymerase chain reaction. In some embodiments, the subject identified as a cancer patient amenable to anti-Tn epitope cancer therapy has at least one mutation in a cosmc coding region. In some embodiments, the mutation in cosmc is a homozygous mutation. In some embodiments, the biological sample may be, or is, cancerous. In some embodiments, the biological sample is exposed to at least one antibody that specifically binds a Tn-antigen. In some embodiments, the subject is identified as a cancer patient amenable to anti-Tn epitope cancer therapy because the biological sample is specifically bound by at least one anti-Tn epitope antibody, as revealed by any means known in the art, such as by labeling the antibody or staining the sample to reveal bound antibody. Exemplary antibodies useful herein include, but are not limited to, BaGs6 (Sun et al., 2018) or any of the antibodies described in Zlocowski et al 2019. Both publications are incorporated herein by reference in relevant part.

In a related aspect, the method of identifying a subject as a cancer patient amenable to anti-Tn epitope cancer therapy further comprises treating the subject by administering a therapeutically effective amount of a therapeutic agent to the subject, wherein the therapeutic agent is the chimeric antigen receptor disclosed herein, the soluble 237 scFv variant disclosed herein, the scFv multimer disclosed herein, or a bispecific antibody containing the soluble scFv variant disclosed herein. In some embodiments, the therapeutic agent is the chimeric antigen receptor. In some embodiments, the therapeutic agent is the soluble 237 scFv variant. In some embodiments, the therapeutic agent is the multimer. In some embodiments, the therapeutic agent is the bispecific antibody containing the soluble scFv variant disclosed herein. In these embodiments, the therapeutic agent is optionally conjugated to a drug (e.g., a chemotherapeutic compound). In some embodiments, the subject is determined to have a loss-of-function mutation in the cosmc gene or the B3GNT6 gene, as compared to a control. In some embodiments, the cancer is any human cancer, provided that cancer is cosmc$^-$. As is known in the art (102), incorporated herein by reference, all known forms of human cancer can be cosmc$^-$. As would be understood in the art, the control can be a sample obtained from a healthy individual or the known sequence of the wild-type gene. Loss-of-function mutations can be determined using methods known in the art, such as reverse transcription PCR (RT-PCR) of the sample or sequencing an encoding nucleic acid (e.g., cDNA).

In some embodiments of this aspect of the disclosure, the cancer is Acute Lymphoblastic Leukemia (ALL), Acute Myeloid Leukemia (AML), Adrenocortical Carcinoma, AIDS-Related Cancers, Kaposi Sarcoma (Soft Tissue Sarcoma), AIDS-Related Lymphoma, Primary CNS Lymphoma, Anal Cancer, Astrocytomas, Atypical Teratoid/Rhabdoid Tumor, Central Nervous System Cancer, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Carcinoid Tumor (Gastrointestinal), Carcinoma of Unknown Primary, Cardiac (Heart) Tumors, Embryonal Tumors, Primary CNS Lymphoma, Cervical Cancer, Chordoma, Chronic Lymphocytic Leukemia (CLL), Chronic Myelogenous Leukemia (CML), Chronic Myeloproliferative Neoplasms, Colorectal Cancer, Craniopharyngioma, Endometrial Cancer (Uterine Cancer), Esophageal Cancer, Esthesioneuroblastoma, Ewing Sarcoma (Bone Cancer), Extracranial Germ Cell Tumor, Eye Cancer, Intraocular Melanoma, Retinoblastoma, Fallopian Tube Cancer, Fibrous Histiocytoma of Bone, Gallbladder Cancer, Gastric (Stomach) Cancer, Gastrointestinal Carcinoid Tumor, Gastrointestinal Stromal Tumors (GIST) (Soft Tissue Sarcoma), Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis, Langerhans Cell Histiocytosis, Hodgkin Lymphoma, Hypopharyngeal Cancer, Intraocular Melanoma, Islet Cell Tumors, Pancreatic Neuroendocrine Tumors, Kidney (Renal Cell) Cancer, Laryngeal Cancer, Leukemia, Lip and Oral Cavity Cancer, Liver Cancer, Lung Cancer (Non-Small Cell and Small Cell), Lymphoma, Male Breast Cancer, Malignant Fibrous Histiocytoma of Bone and Osteosarcoma, Melanoma, Merkel Cell Carcinoma, Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Chronic Myeloproliferative Neoplasms, Nasal Cavity and Paranasal Sinus Cancer, Nasopharyngeal Cancer, Neuroblastoma, Non-Hodgkin Lymphoma, Oral Cancer, Lip and Oral Cavity Cancer, Oropharyngeal Cancer, Osteosarcoma, Malignant Fibrous Histiocytoma of Bone, Ovarian Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Salivary Gland Cancer, Sarcoma, Soft Tissue Sarcoma, Uterine Sarcoma, Sézary Syndrome (Lymphoma), Skin Cancer, Small Intestine Cancer, Squamous Neck Cancer with Occult Primary, Metastatic, Stomach (Gastric) Cancer, T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter, Ureter and Renal Pelvis Cancers, Transitional Cell Cancer (Kidney (Renal Cell) Cancer, Urethral Cancer, Uterine Cancer, Endometrial Uterine Sarcoma, Vaginal Cancer, Vascular Tumors, Vulvar Cancer, or Wilms Tumor. In some embodiments, the therapeutic agent comprises a tryptophan substitution for a histidine residue at position 98 of SEQ ID NO:27 in the complementarity determining region 3 of the antibody 237 light chain variable region. In some embodiments, the therapeutic agent comprises a glutamate substitution for a valine residue at position 99 of SEQ ID NO:28 in the complementarity determining region 3 of the antibody 237 light chain variable region. In some of these embodiments, the method further comprises a tryptophan substitution for a histidine residue at position 98 of SEQ ID NO:20 in the complementarity determining region 3 of the antibody 237 light chain variable region. In some embodiments, the scFv multimer is a tetramer. In some embodiments, a nanomolar concentration of the therapeutic agent detectably binds to a Tn epitope.

A related aspect of the disclosures is a method of identifying a subject as a cancer patient amenable to anti-Tn epitope cancer therapy comprising (a) obtaining a biological sample from a subject; (b) determining the level of core 1 β3-Gal-T-specific molecular chaperone (COSMC) and/or T-Synthase in the sample; (c) comparing the level of COSMC and/or T-Synthase in the sample to a control; and (d) identifying the subject as a cancer patient amenable to anti-Tn epitope cancer therapy if the level of COSMC and/or T-Synthase is lower in the sample of the subject than in the control. In some embodiments, the sample of the subject has a lower level of COSMC than the control. In some embodiments, the sample of the subject has a lower level of T-Synthase than the control. In some embodiments, the biological sample is obtained from a subject with cancer or is from a tumor. As would be understood in the art, the control can be a sample obtained from a healthy individual or the control can be a level of COSMC and/or T-Synthase known in the art as characteristic of one or more healthy individuals, such as by prior measurements of the levels of COSMC and/or T-Synthase from healthy individual(s). In some embodiments, the subject has a mutation in the gene encoding COSMC and/or the gene encoding T-Synthase.

Another related aspect provides a method of identifying a subject as a cancer patient amenable to anti-Tn epitope cancer therapy further comprising treating the subject by administering a therapeutically effective amount of a therapeutic agent to the subject, wherein the therapeutic agent is the chimeric antigen receptor disclosed herein, the soluble 237 scFv variant disclosed herein, the scFv multimer disclosed herein, or a bispecific antibody containing the soluble scFv variant disclosed herein. In some embodiments, the therapeutic agent is the chimeric antigen receptor. In some embodiments, the therapeutic agent is the soluble 237 scFv variant. In some embodiments, the therapeutic agent is the multimer. In some embodiments, the therapeutic agent is the bispecific antibody containing the soluble scFv variant disclosed herein. In some embodiments, the cancer is any human cancer, provided that cancer is cosmc$^{-}$. As is known in the art (102), incorporated herein by reference, all known forms of human cancer can be cosmc$^{-}$.

In some embodiments of the method of this aspect of the disclosure, the cancer is Acute Lymphoblastic Leukemia (ALL), Acute Myeloid Leukemia (AML), Adrenocortical Carcinoma, AIDS-Related Cancers, Kaposi Sarcoma (Soft Tissue Sarcoma), AIDS-Related Lymphoma, Primary CNS Lymphoma, Anal Cancer, Astrocytomas, Atypical Teratoid/Rhabdoid Tumor, Central Nervous System Cancer, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Carcinoid Tumor (Gastrointestinal), Carcinoma of Unknown Primary, Cardiac (Heart) Tumors, Embryonal Tumors, Primary CNS Lymphoma, Cervical Cancer, Chordoma, Chronic Lymphocytic Leukemia (CLL), Chronic Myelogenous Leukemia (CML), Chronic Myeloproliferative Neoplasms, Colorectal Cancer, Craniopharyngioma, Endometrial Cancer (Uterine Cancer), Esophageal Cancer, Esthesioneuroblastoma, Ewing Sarcoma (Bone Cancer), Extracranial Germ Cell Tumor, Eye Cancer, Intraocular Melanoma, Retinoblastoma, Fallopian Tube Cancer, Fibrous Histiocytoma of Bone, Gallbladder Cancer, Gastric (Stomach) Cancer, Gastrointestinal Carcinoid Tumor, Gastrointestinal Stromal Tumors (GIST) (Soft Tissue Sarcoma), Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis, Langerhans Cell Histiocytosis, Hodgkin Lymphoma, Hypopharyngeal Cancer, Intraocular Melanoma, Islet Cell Tumors, Pancreatic Neuroendocrine Tumors, Kidney (Renal Cell) Cancer, Laryngeal Cancer, Leukemia, Lip and Oral Cavity Cancer, Liver Cancer, Lung Cancer (Non-Small Cell and Small Cell), Lymphoma, Male Breast Cancer, Malignant Fibrous Histiocytoma of Bone and Osteosarcoma, Melanoma, Merkel Cell Carcinoma, Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Chronic Myeloproliferative Neoplasms, Nasal Cavity and Paranasal Sinus Cancer, Nasopharyngeal Cancer, Neuroblastoma, Non-Hodgkin Lymphoma, Oral Cancer, Lip and Oral Cavity Cancer, Oropharyngeal Cancer, Osteosarcoma, Malignant Fibrous Histiocytoma of Bone, Ovarian Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Salivary Gland Cancer, Sarcoma, Soft Tissue Sarcoma, Uterine Sarcoma, Sézary Syndrome (Lymphoma), Skin Cancer, Small Intestine Cancer, Squamous Neck Cancer with Occult Primary, Metastatic, Stomach (Gastric) Cancer, T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter, Ureter and Renal Pelvis Cancers, Transitional Cell Cancer (Kidney (Renal Cell) Cancer, Urethral Cancer, Uterine Cancer, Endometrial Uterine Sarcoma, Vaginal Cancer, Vascular Tumors, Vulvar Cancer, or Wilms Tumor. In some embodiments, the therapeutic agent comprises a tryptophan substitution for a histidine residue at position 98 of SEQ ID NO:27 in the complementarity determining region 3 of the antibody 237 light chain variable region. In some embodiments, the therapeutic agent comprises a glutamate substitution for a valine residue at position 99 of SEQ ID NO:28 in the complementarity determining region 3 of the antibody 237 light chain variable region. In some of these embodiments, the method further comprises a tryptophan substitution for a histidine residue at position 98 of SEQ ID NO:20 in the complementarity determining region 3 of the antibody 237 light chain variable region. In some embodiments, the scFv multimer is a tetramer. In some embodiments, a nanomolar concentration of the therapeutic agent detectably binds to a Tn epitope.

Yet another aspect of the disclosure is directed to a cell expressing a detection agent, wherein the detection agent is the chimeric antigen receptor disclosed herein, the soluble scFv variant disclosed herein, the scFv multimer disclosed herein, or a bispecific antibody containing the soluble scFv variant disclosed herein, and wherein the detection agent detectably binds to a Tn-glycopeptide with truncated glycosylation, including binding of a nanomolar or sub-nanomolar concentration of the detection agent to a Tn glycopeptide with truncated glycosylation.

Still another aspect of the disclosure is drawn to an engineered T-cell comprising a CAR disclosed herein. In some embodiments, the CAR specifically binds to (i.e., recognizes) at least one glycopeptide comprising a Tn epitope. In some embodiments, the CAR specifically binds to, or recognizes, at least two glycopeptides that each comprise a Tn epitope. In some embodiments, the glycopeptide comprises a Tn epitope of PDPN, TFRC, MUC1, TFRC, ZIP6, EVI2B, LAMP, PCDH, CD43, or PDXL.

Another aspect of the disclosure is drawn to a method of identifying a cancer subject sub-population amenable to anti-Tn epitope cancer therapy comprising: (a) contacting a sample from a cancer subject with a detection agent, wherein the detection agent is the chimeric antigen receptor disclosed herein, the soluble 237 scFv variant disclosed herein, or the scFv multimer disclosed herein; (b) assessing the binding of the detection agent to material in the sample; and (c) identifying the cancer subject as amenable to anti-Tn epitope cancer therapy if the detection agent detectably binds to material in the sample. In some embodiments, the detection agent is the chimeric antigen receptor disclosed herein, the soluble 237 scFv variant disclosed herein, or the scFv multimer disclosed herein. In some embodiments, the detection agent comprises a tryptophan substitution for a histidine residue at position 98 of SEQ ID NO:27 in the complementarity determining region (CDRL3) of the antibody 237 light chain variable region. In some embodiments, the detection agent comprises a glutamate substitution for a valine residue at position 99 of SEQ ID NO:28 in the complementarity determining region (CDRL3) of the antibody 237 light chain variable region. In some embodiments wherein the detection agent comprises a glutamate substitution for a valine residue at position 99 of SEQ ID NO:28 in the complementarity determining region 3 (CDRL3) of the antibody 237 light chain variable region, the detection agent further comprises a tryptophan substitution for a valine residue at position 98 of SEQ ID NO:20 in the complementarity determining region 3 (CDRL3) of the antibody 237 light chain variable region. In some embodiments, the scFv multimer is a tetramer. In some embodiments, a nanomolar concentration of the detection agent detectably binds to a Tn epitope, such as wherein a sub-nanomolar concentration of the detection agent detectably binds to a Tn epitope.

Still another aspect of the disclosure is drawn to a method of identifying a cancer subject amenable to anti-Tn epitope cancer therapy comprising (a) obtaining a biological sample that may be cancerous from a subject; (b) exposing the sample to at least one anti-Tn epitope antibody that reacts with at least one Tn-antigen and (c) identifying the subject aa a cancer subject if the at least one anti-Tn epitope antibody detectably binds to the biological sample at a level greater than the at least one anti-Tn epitope antibody detectably binds to a sample obtained from a healthy subject. Any anti-Tn epitope antibody or fragment thereof is useful in the methods disclosed herein. Exemplary antibodies include BaGs6 (Sun et al., 2018) or those anti-Tn epitope antibodies described in Zlocowski et al 2019, which are both incorporated herein by reference in relevant part.

In some embodiments, the method according to this aspect of the disclosure further comprises treating the subject by administering a therapeutically effective amount of a therapeutic agent to the subject, wherein the therapeutic agent is the chimeric antigen receptor disclosed herein, the soluble 237 scFv variant disclosed herein, or the scFv multimer disclosed herein. In some embodiments, the therapeutic agent is the chimeric antigen receptor according to the disclosure. In some embodiments, the therapeutic agent is the soluble 237 scFv variant according to the disclosure. In some embodiments, the therapeutic agent is the multimer according to the disclosure. In some embodiments, the subject is determined to have a loss-of-function mutation in the cosmc gene or the B3GNT6 gene compared to a control. As would be understood in the art, the control can be a sample obtained from a healthy individual. A loss-of-function mutation can be determined using methods known in the art, such as reverse transcription PCR (RT-PCR) of the sample or sequencing an encoding nucleic acid (e.g., cDNA). In some embodiments, the cancer is Acute Lymphoblastic Leukemia (ALL), Acute Myeloid Leukemia (AML), Adrenocortical Carcinoma, AIDS-Related Cancers, Kaposi Sarcoma (Soft Tissue Sarcoma), AIDS-Related Lymphoma, Primary CNS Lymphoma, Anal Cancer, Astrocytomas, Atypical Teratoid/Rhabdoid Tumor, Central Nervous System Cancer, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Carcinoid Tumor (Gastrointestinal), Carcinoma of Unknown Primary, Cardiac (Heart) Tumors, Embryonal Tumors, Primary CNS Lymphoma, Cervical Cancer, Chordoma, Chronic Lymphocytic Leukemia (CLL), Chronic Myelogenous Leukemia (CML), Chronic Myeloproliferative Neoplasms, Colorectal Cancer, Craniopharyngioma, Endometrial Cancer (Uterine Cancer), Esophageal Cancer, Esthesioneuroblastoma, Ewing Sarcoma (Bone Cancer), Extracranial Germ Cell Tumor, Eye Cancer, Intraocular Melanoma, Retinoblastoma, Fallopian Tube Cancer, Fibrous Histiocytoma of Bone, Gallbladder Cancer, Gastric (Stomach) Cancer, Gastrointestinal Carcinoid Tumor, Gastrointestinal Stromal Tumors (GIST) (Soft Tissue Sarcoma), Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis, Langerhans Cell Histiocytosis, Hodgkin Lymphoma, Hypopharyngeal Cancer, Intraocular Melanoma, Islet Cell Tumors, Pancreatic Neuroendocrine Tumors, Kidney (Renal Cell) Cancer, Laryngeal Cancer, Leukemia, Lip and Oral Cavity Cancer, Liver Cancer, Lung Cancer (Non-Small Cell and Small Cell), Lymphoma, Male Breast Cancer, Malignant Fibrous Histiocytoma of Bone and Osteosarcoma, Melanoma, Merkel Cell Carcinoma, Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Chronic Myeloproliferative Neoplasms, Nasal Cavity and Paranasal Sinus Cancer, Nasopharyngeal Cancer, Neuroblastoma, Non-Hodgkin Lymphoma, Oral Cancer, Lip and Oral Cavity Cancer, Oropharyngeal Cancer, Osteosarcoma, Malignant Fibrous Histiocytoma of Bone, Ovarian Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Salivary Gland Cancer, Sarcoma, Soft Tissue Sarcoma, Uterine Sarcoma, Sézary Syndrome (Lymphoma), Skin Cancer, Small Intestine Cancer, Squamous Neck Cancer with Occult Primary, Metastatic, Stomach (Gastric) Cancer, T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter, Ureter and Renal Pelvis Cancers, Transitional Cell Cancer (Kidney (Renal Cell) Cancer, Urethral Cancer, Uterine Cancer, Endometrial Uterine Sarcoma, Vaginal Cancer, Vascular Tumors, Vulvar Cancer, or Wilms Tumor. In some embodiments, the therapeutic agent comprises a tryptophan substitution for a histidine residue at position 98 of SEQ ID NO:27 in the complementarity determining region 3 of the antibody 237 light chain variable region. In some embodiments, the therapeutic agent comprises a glutamate substitution for a valine residue at position 99 of SEQ ID NO:28 in the complementarity determining region 3 of the antibody 237 light chain variable region. In some embodiments, the method of this aspect of the disclosure further comprises a tryptophan substitution for a histidine residue at position 98 of SEQ ID NO:20 in the complementarity determining region 3 of the antibody 237 light chain variable region. In some embodiments, the scFv multimer is a tetramer. In some embodiments, a nanomolar or sub-nanomolar concentration of the therapeutic agent detectably binds to a Tn epitope.

Another aspect of the disclosure is directed to a cell expressing the detection agent, wherein the detection agent is the chimeric antigen receptor disclosed herein, the soluble scFv variant disclosed herein, or the scFv multimer disclosed herein, wherein a nanomolar or sub-nanomolar concentration of the detection agent detectably binds to a Tn-glycopeptide with truncated glycosylation.

Other features and advantages of the disclosure will become apparent from the following detailed description. It should be understood, however, that the detailed description and the specific examples, while indicating embodiments of the disclosed subject matter, are given by way of illustration only, because various changes and modifications within the spirit and scope of the disclosure will become apparent to those skilled in the art from this detailed description.

BRIEF DESCRIPTION OF THE DRAWING

FIG. 14. CDR libraries in 237 scFv: Insights from crystal structure of 237 mAb:OTS8 peptide. Brooks et al., Proc. Natl. Acad. Sci. (USA): 107(22)L10056-10061 (2010) reported crystallization of the 237 Immunoglobulin G with the OTS-8 glycopeptide. That study also determined the buried surface area of each complementarity determining region (CDR) of the light and heavy chains (CDRL1, L2, L3 and CDRH1, H2 and H3, respectively) with glycopeptide and GalNAc. This information, and analysis of the crystal structure, guided the selection of CDR residues to make libraries.

FIG. 21. Tn-OTS8p binding profiles of select 237 mutants: Affinities 30-times higher than parental scFv. (A) Three unique 237scFv mutants (WQ, WA and WE), and the parent 237 scFv were stained with various concentrations of OTS8 peptide, and analyzed by flow cytometry to calculate approximate dissociation constants. As indicated, each mutant exhibited a $K_D$ value of about 5 nM for Tn-OTS8 peptide, which was approximately 30-fold higher than the $K_D$ of 140 nM measured by surface plasmon resonance (SPR) for 237 IgG Fab domain (in (C): Brooks et al., 2010, PNAS). (B) To determine their off-rates, each mutant was stained with 30 nM biotinylated Tn-OTS8 peptide. After washing, the mutants were stained with 100 nM Tn-OTS8 peptide (not biotinylated). The decrease in binding to biotinylated Tn-OTS8p by each mutant was measured over a period of 4 hours, to calculate approximate half-lives ($t_{1/2}$) and off-rates ($k_{off}$). As indicated, WE mutant exhibited longest half-life of approximately 30 minutes, and an off-rate that was 30-fold slower than the 237 monoclonal antibody Fab interaction with OTS8 peptide reported in (C). See Brooks et al., Proc. Natl. Acad. Sci. (USA) 107(22): 10056-10061 (2010).

DETAILED DESCRIPTION

Figure 1:
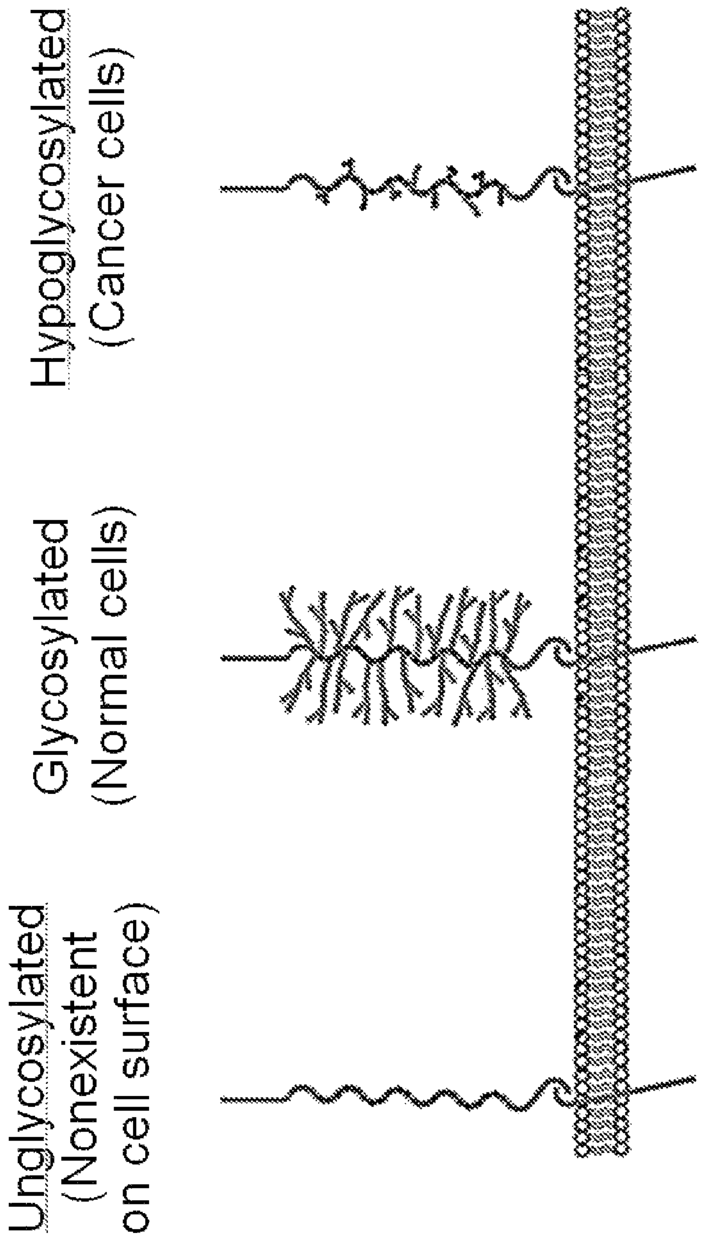
FIG. 1. Schematic representation of cell-surface-bound hypoglycosylated cancer-specific glycopeptide antigens.

About 1-3% of all human cancers have somatic mutations in COSMC, coding for a chaperone protein that is essential for the normal activity of T-synthase, the only enzyme that catalyzes the formation of core 1 O-glycan Galβ1-3GalNAcα1-Ser/Thr (T antigen). The COSMC loss-of-function mutations abolish T-synthase activity and cause the extension of O-linked glycans to stop after the formation of the common O-glycan precursor N-acetyl galactosamine (GalNAc)—O-Ser/Thr, which is called Tn antigen (32). Disruption of Cosmc in mice is embryonically lethal, and Tn expression on the cell surface in humans has only been disclosed in cases of cancers or autoimmune diseases acquired via somatic mutation of COSMC (39, 42, 102). The 237 antibody is a monoclonal IgG antibody that recognizes a Tn-glycosylated epitope on murine podoplanin (PDPN), formed due to incomplete O-glycosylation at Thr77 because of a Cosmc mutation (16). As revealed by crystallography, 237 antibody binding requires interaction with the PDPN backbone, as well as with the GalNAc moiety resulting from the cancer-specific COSMC mutation (3). CAR-engineered T cells have shown great potential in treating late-stage leukemia (139,140), but broader application of the technology is largely limited by the severe toxicity occurring when targeting non-cancer-specific targets like tumor-associated antigens (TAAs), and relapses from mono-targeting therapies due to tumor heterogeneity. To address the needs for tumor-specific engineered T cell therapies, the 237 antibody was made into a CAR construct, and the 237 CAR-transduced T cells are shown herein to recognize Tn-linked targets on cancer cells with higher sensitivity than those recognized by the 237 antibody that are predicted by 237 antibody binding (59). The experiments disclosed herein demonstrate the in vitro and in vivo recognition of targets generated by COSMC mutations, by 237 CAR-T cells. Moreover, the 237CAR-engineered T cells target multiple Tn-glycopeptide antigens on a single cancer cell.

Figure 3:
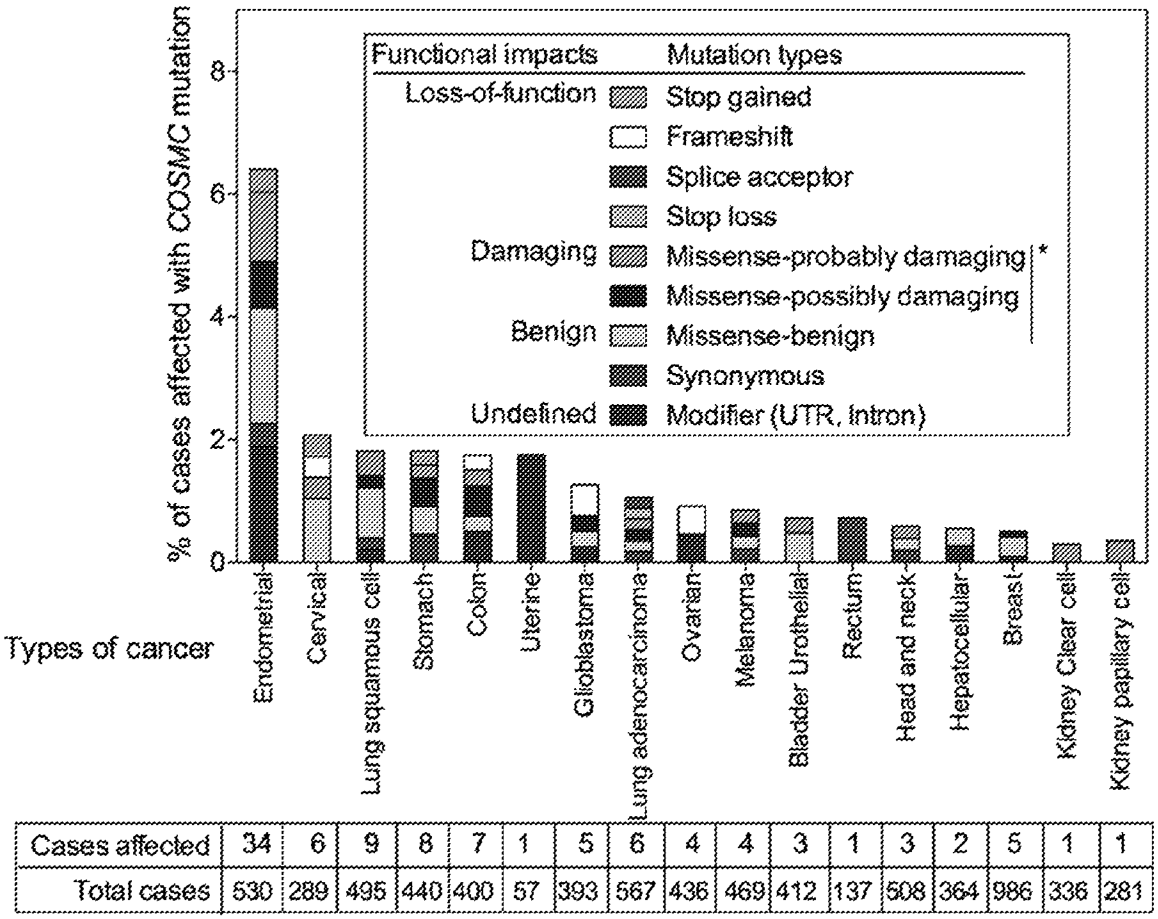
FIG. 3. The frequency and the type of COSMC mutations in human cancers across different cancer types. Survey data from the Cancer Genome Atlas database was used to characterize the frequency and type of COSMC mutations in various human cancers. Across 17 cancer types and 7,100 patient samples, COSMC mutation is present in about 0.5-6.5% of human cancers. The types of mutation are indicated as that in the legends within the figure. The number of cases affected by COSMC mutations out of the total number of cases in the database of the particular cancer type is shown at the bottom. Synonymous mutations are excluded from the graph.
Figure 4:
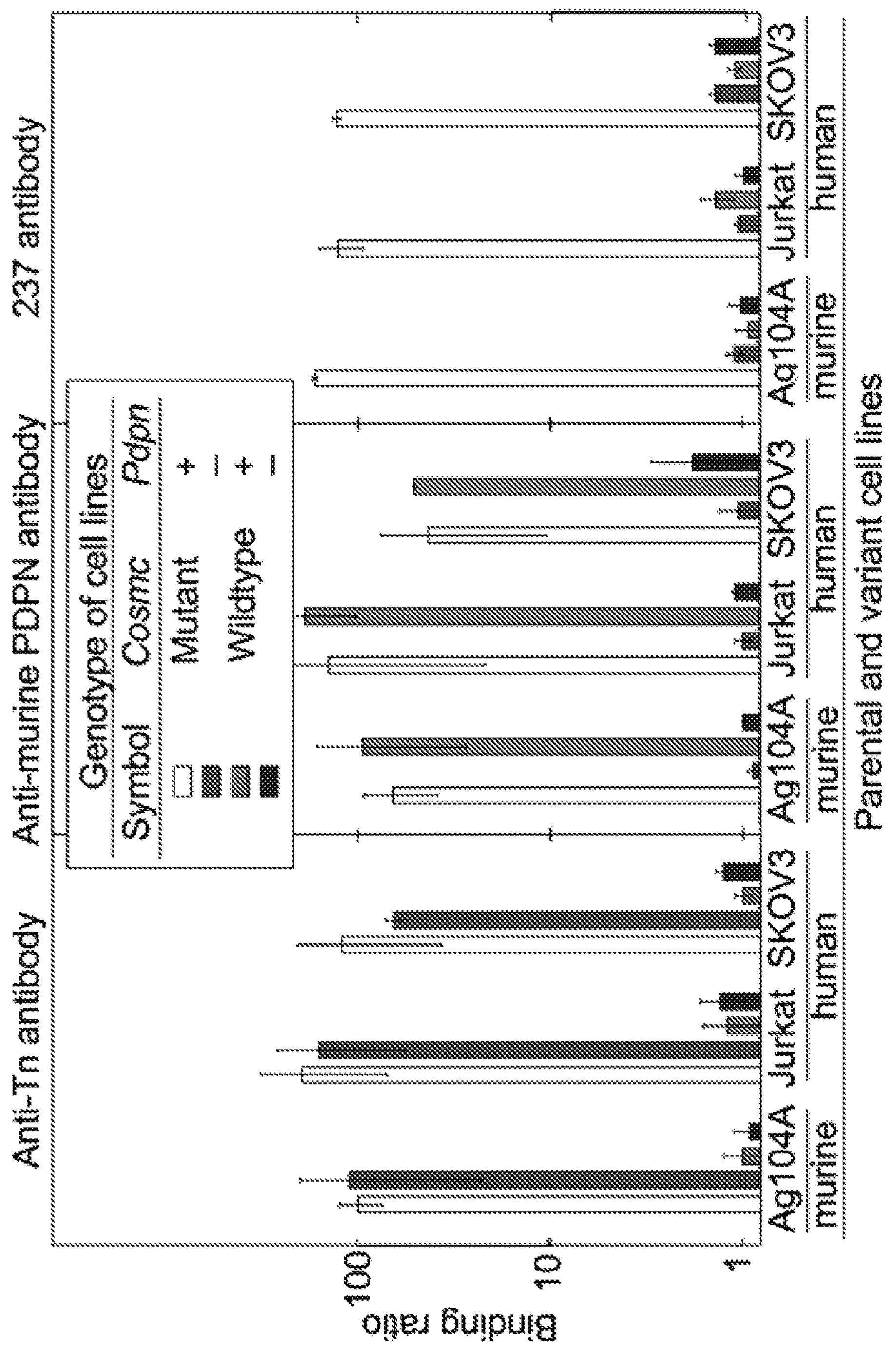
FIG. 4. 237 monoclonal antibody selectively binds to Tn-glycosylated murine PDPN. 237Ab only stained COSMC mutant cell lines that are expressing mPDPN. Mean±SEM, n=3. Cosmc encodes a chaperone for the T-synthase essential for elongation of glycans beyond the initial Tn-structure. The Ag104A cell line is a murine sarcoma cell line that carries a Cosmc null mutation. The mutation results in Tn-glycosylation of all O-linked glycoproteins on the cell surface, including the murine podoplanin (PDPN). For Ag104A, a PDPN-negative variant was made by CRISPR-Cas9 knockout of Pdpn; both this variant and the parental Ag104A cell lines were reconstituted with wild-type Cosmc to generate the two additional variants with normal glycosylation. For the Jurkat cell line, a human T cell lymphoma cell line that carries a natural COSMC null mutation, a COSMC wild-type variant was made by COSMC transduction; both the COSMC wild-type and the parental Jurkat cell lines were transduced with Pdpn to make the two murine PDPN-expressing variants. For the SKOV3 cell line, a human ovarian cancer cell line with normal COSMC function, a Tn-glycosylated variant was made by CRISPR-Cas9 knockout of COSMC; both the COSMC knockout and the parental SKOV3 cell lines were transduced with Pdpn to generate the two murine PDPN-expressing variants. Each cell line was stained with one of the three primary murine monoclonal antibodies indicated in the Figure, followed by goat-anti-mouse Ig-APC as secondary antibody. The level of monoclonal antibody binding to the cell surface is presented as the binding ratio of the MFI of samples stained with both primary and secondary antibodies divided by the MFI of samples stained with secondary antibody alone.
Figure 25:
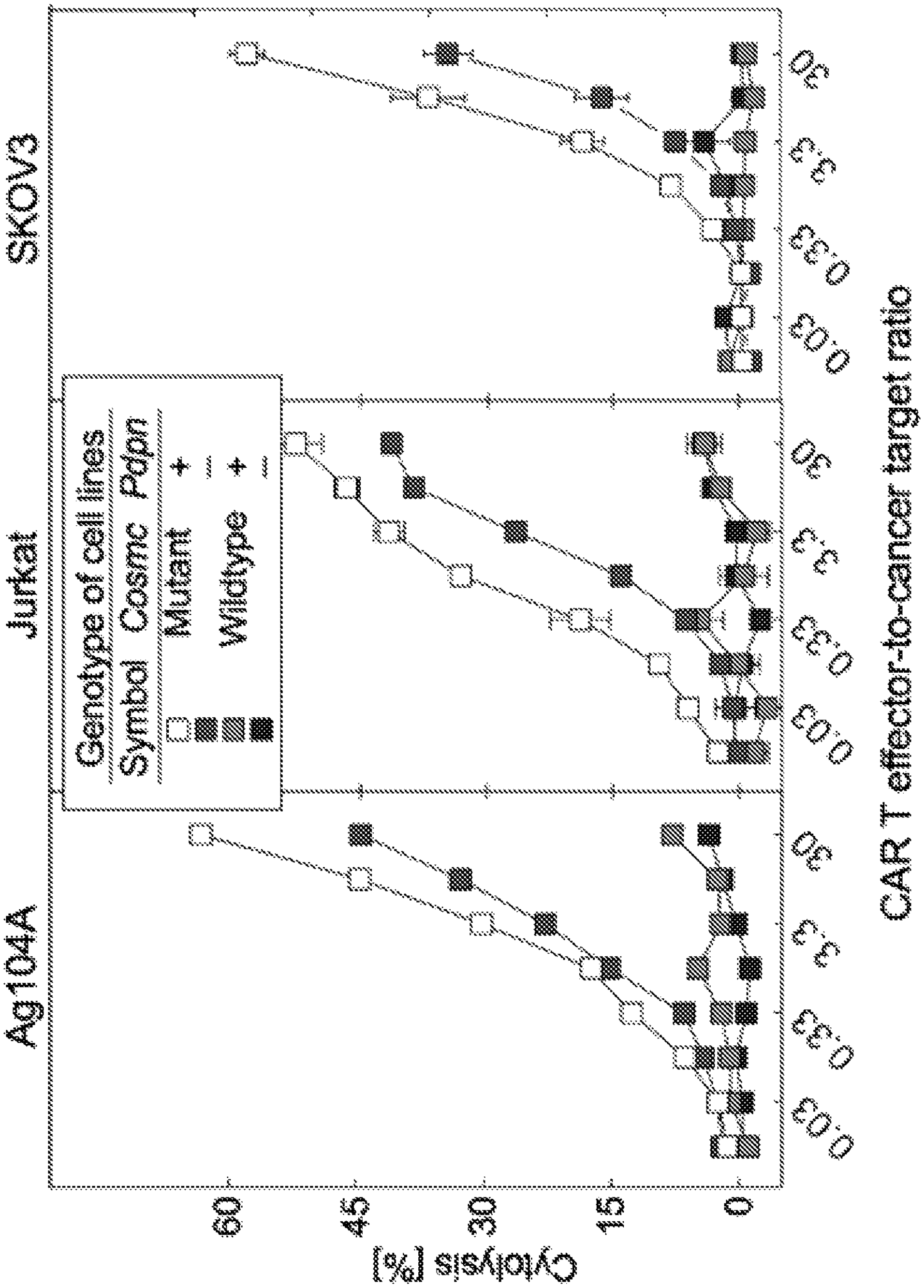
FIG. 25. 237 CAR-T cells recognize and kill $Cosmc^{Mut}$ cancers not expressing murine Podoplanin (PDPN). 237 CAR-T cells lyse COSMC null cell lines in the presence and also in the absence of murine PDPN expression. 5000 $^{51}Cr$-labeled target cells per well of a 96-well plate were incubated for 4 hours with 237 CAR-T cells at the indicated effector-to-target ratio. The level of $^{51}Cr$ release into the medium by CAR-T-exposed targets (experimental release) was compared to the level of release in the absence of CAR-T cells (spontaneous release). For maximum release, targets were lysed by ZAP-OGLOBIN II. The percentage of specific lysis was calculated by the formula: % cytolysis=[(experimental release−spontaneous release)/(maximum release−spontaneous release)]×100. Spontaneous release was less than 15% of maximum release.
Figure 26:
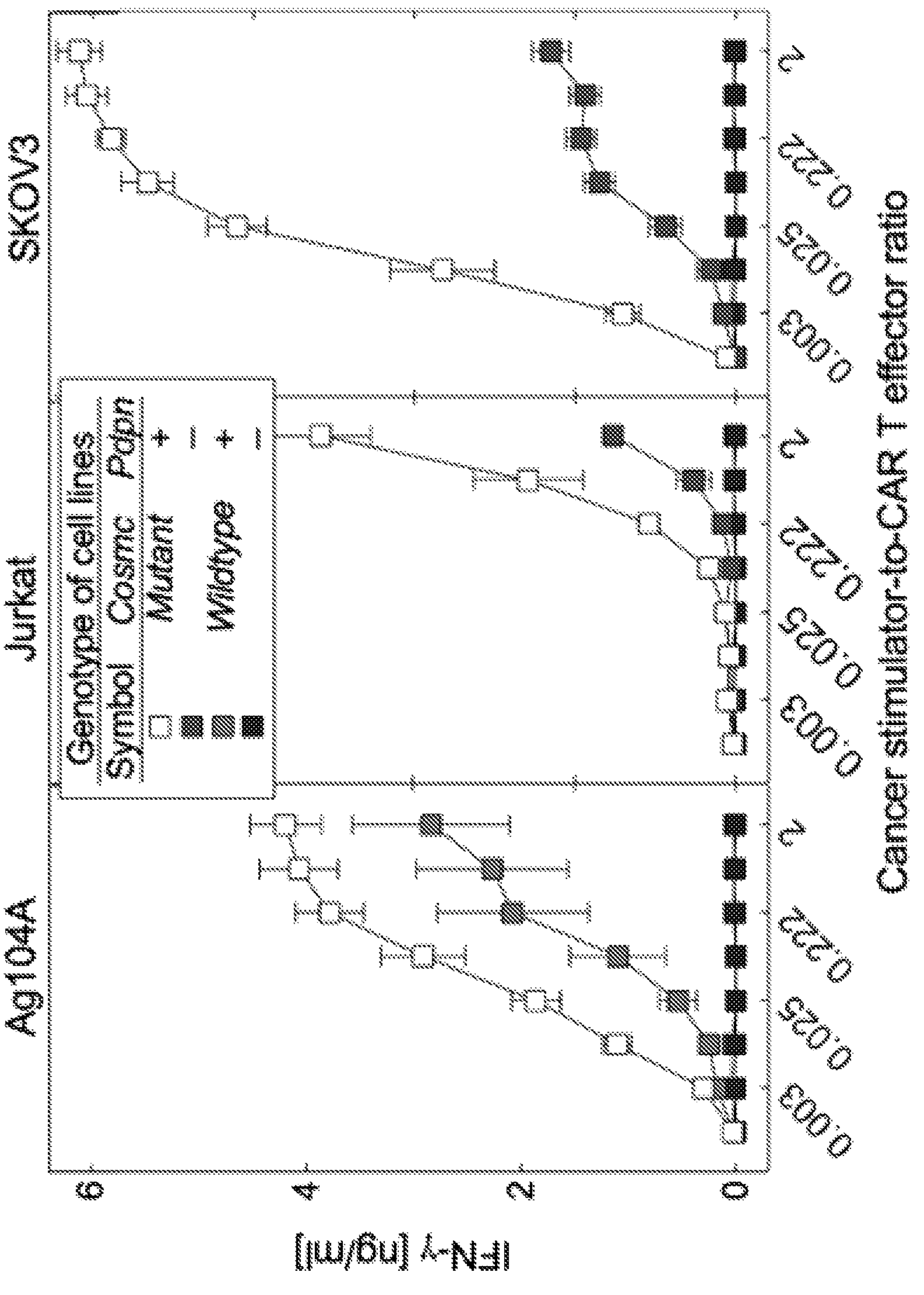
FIG. 26. 237 CAR-T cells recognize $Cosmc^{Mut}$ cancers not expressing murine Podoplanin (PDPN) unpredicted by 237 Antibody binding. 237 CAR-T cells were stimulated by COSMC null cell lines to produce IFN-γ even in the absence of murine PDPN expression. 5000 237 CAR-T cells per well of a 96-well plate were incubated for 24 hours with cancer cells as stimulators at the indicated ratio. The level of IFN-γ release into the supernatant was measured by sandwich ELISA.
Figure 27:
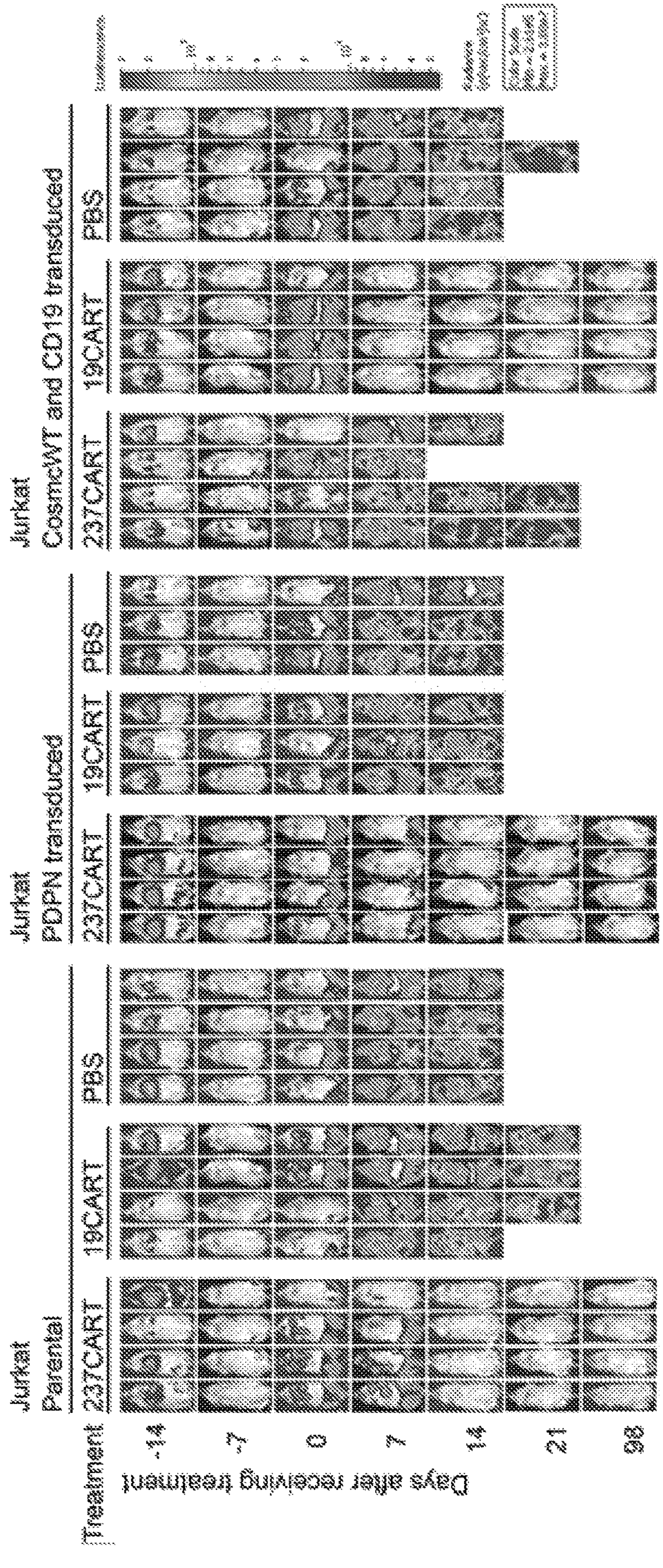
FIG. 27. 237 CAR-T cells recognize $Cosmc^{Mut}$ cancers independent of Podoplanin expression in vivo and 237 CAR-T cells eradicate established cancers in vivo by recognizing Tn glycopeptide epitopes not predicted by 237 full IgG binding. Five million of each Jurkat variant, as indicated, were i.v. injected into each NSG mouse. After Jurkat leukemia has established in the host 14 days post-transplantation, five million 237 CAR- or CD19 CAR-transduced OT1Rag1KO T cells were given via i.p. injection. Injection of the same volume of PBS was used as negative control. Disease progression was followed weekly by BLI. CART cell treatment of mice with widely disseminated Jurkat leukemia. Jurkat cancer cells were either Pdpn-transduced, CD19- and COSMC(WT)-transduced, or parental (untransduced). NSG received either $5\times10^6$ 237 CART cells or CD19CART cells or PBS two weeks after cancer-cell inoculation (n=4 or 3 mice per group, as indicated in the Figure).
Figure 45:
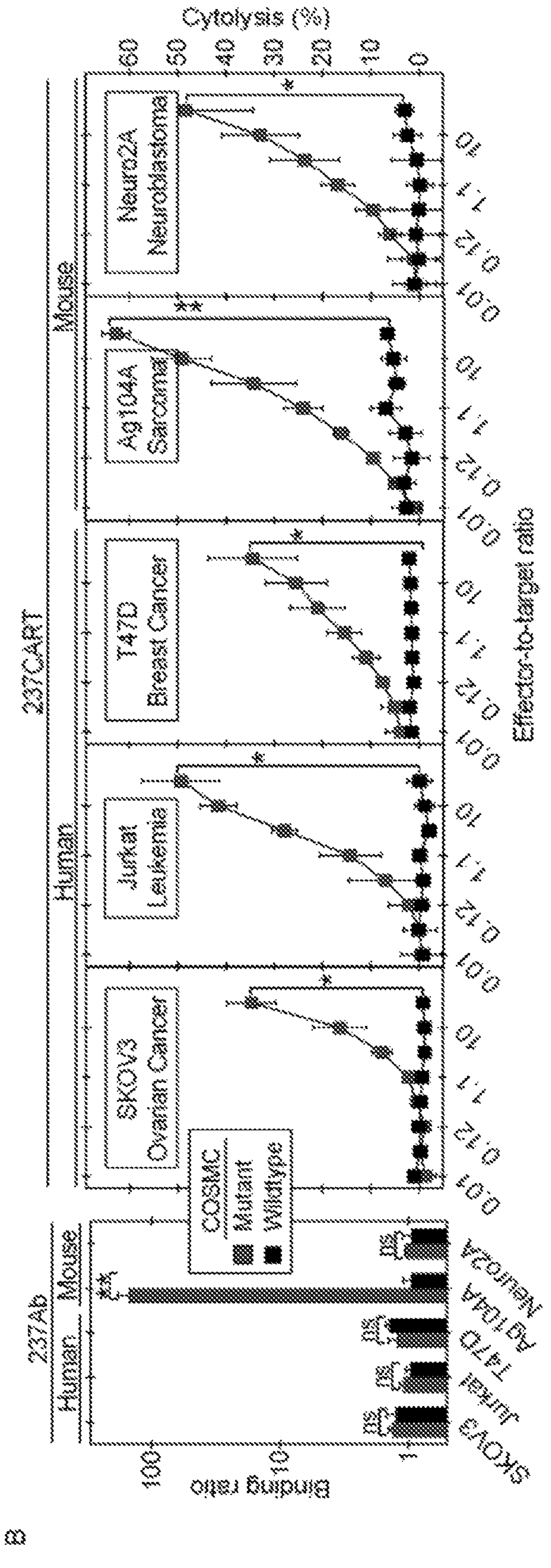
FIG. 45. 237 CAR-T cells eradicate COSMC-mutant cancer independently of Tn-mPDPN expression and lyse multiple cancers lacking Tn-mPDPN. Left panel: 237Ab staining of human and murine cell lines either mutant or wild-type for COSMC. Binding ratio represents the MFI of the staining with both, primary (237Ab) and secondary Ab (anti-IgG-APC), divided by the MFI of staining with secondary Ab only. Mean±SEM, n=3. Right panels: 237CART cells lysed all 3 human cell lines and 2 murine cell lines dependent on loss of function mutations in COSMC. Mean±SEM, n=3.

As noted above, COSMC mutations are present in 1-3% of all human cancers (FIG. 3) and the loss of COSMC function abolishes T-synthase activity and results in Tn-hypoglycosylation of all O-linked glycoproteins on the cell surface (32). The inventors have developed a cancer-specific monoclonal IgG antibody designated the 237 antibody, which recognizes the Tn-PDPN resulting from COSMC mutation (16), and the antibody recognizes COSMC dysfunctional cell lines only when they are also expressing murine PDPN on the cell surface (FIG. 4). Because of the discrepant reactivities of 237CART cells and the 237Ab, the specificities of these two reagents for cell lines expressing or lacking Tn-mPDPN or COSMC function were compared. FIG. 4 shows that the 237Ab selectively bound only cell lines expressing mPDPN and lacking COSMC. The 237Ab neither bound COSMC-wild-type cell lines with normally glycosylated mPDPN nor COSMC-mutant cell lines lacking mPDPN expression. To compare 237CART cells with CD19CART cells in their efficacy at eliminating cancer in vivo, NSG mice with 14-day-established Jurkat leukemia were treated with OT1-transgenic $Rag^{-/-}$ T cells virally transduced with 237CARs or CD19CARs. Jurkat is a human T-cell leukemia that, like AG104A, carries a spontaneous loss-of-function mutation in Cosmc. The benefits of the exceptional cancer-specificity of 237 antibody binding and the potency of engineered T cell treatment for cancers led to the development of the 237 CAR constructs disclosed herein, which comprise a 237 variable region integrated into a CAR construct and used to engineer primary OT1×$Rag1^{-/-}$ T cells retrovirally. The 237 CAR-engineered T cells exhibited exceptional activity and sensitivity towards recognition of Tn-murine PDPN-expressing cell lines. Surprisingly, the 237 CAR-T cells also recognized COSMC mutant cancers from distinct backgrounds without PDPN expression (FIGS. 25 and 26). The further investigations of the efficacy of 237 CAR-engineered T cells in treating COSMC mutant cancers with or without PDPN expression disclosed herein revealed that treatment with the 237 CAR-T cells was similarly effective in eradicating established Jurkat leukemia in vivo, regardless of PDPN expression (FIG. 27) The left panel of FIG. 27 shows that 237 CAR-T cells completely eradicated a systematic burden of Jurkat leukemia transduced to express Tn-mPDPN and achieved long-term disease-free survival. The efficacy was comparable to that of CD19CART cells treating Jurkat expressing CD19 and wild-type (WT) COSMC in FIG. 27, middle panel. Mice treated with unmatched CART cells died as fast as that of the PBS-treated group, indicating the absence of allogeneic effects by the transferred 237CART cell-transduced OT-$1Rag^{-/-}$ T cells on the growth of cancers. Surprisingly, 237CART cells also achieved similar therapeutic efficacy in treating the parental Jurkat cells (FIG. 27, right panel) as it did for the Jurkat cells transduced with murine Pdpn (FIG. 27, left panel), while the 237 antibody did not bind effectively to Jurkat cells that naturally lacks murine PDPN expression (FIG. 45, left panel). Furthermore, 237CART cells killed all five different human or mouse cell lines tested, as long as they lacked COSMC function due to mutation(s) (FIG. 45, right panel), even though only the murine sarcoma Ag104A naturally expressed mPDPN. Thus, the broadened specificity of 237CART cells was not predicted by 237Ab binding but remained cancer-specific due to its dependency on loss of COSMC function.

Figure 28:
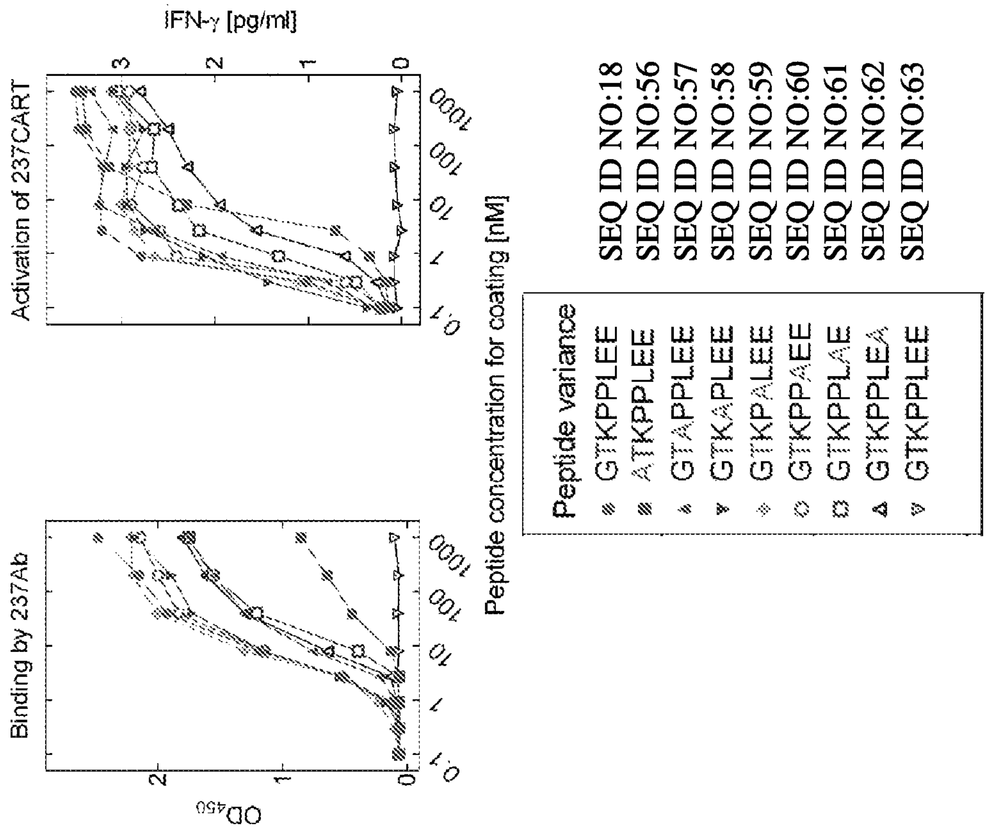
FIG. 28. 237 antibody binding and 237 CAR-T cell recognition of PDPN variants. 237 CAR-T cells recognize a wider range of Tn-glycopeptides than that predicted by 237Ab binding. 237 antibody binding to immobilized PDPN variants was measured by standard ELISA, wherein the PDPN variants with Tn-linked to threonine antigen Thr77 (red T or second amino acid shown) contained site-directed Ala substitutions of each amino acid residue in the PDPN binding site for the 237 antibody (denoted by "A" within the sequence). Biotinylated peptides were immobilized on streptavidin-coated plates via the common N-terminus at the coating concentration indicated. 237 CAR-T cell activation was assessed by measuring IFN-γ secretion of the CAR-T cells exposed to the same immobilized PDPN variants after 24-hour incubation. 237 CAR-T cells tolerated single Ala mutation at multiple different positions within the epitope recognized by the 237 antibody. Biotinylated single Ala replacement of each amino acid residue within the 237 antibody binding epitope of PDPN were chemically synthesized and immobilized on streptavidin-coated plates. 237 full IgG binding to the immobilized peptides was determined by sandwich ELISA (LEFT), and 237 CAR-T cell recognition was tested by determining the level of IFN-gamma release by 5000 237 CAR-T cells into the supernatant after 24-hour co-incubation with immobilized peptides on plate surfaces. The negative control is the PDPN peptide without a Tn-linked threonine (black T).
Figure 29:
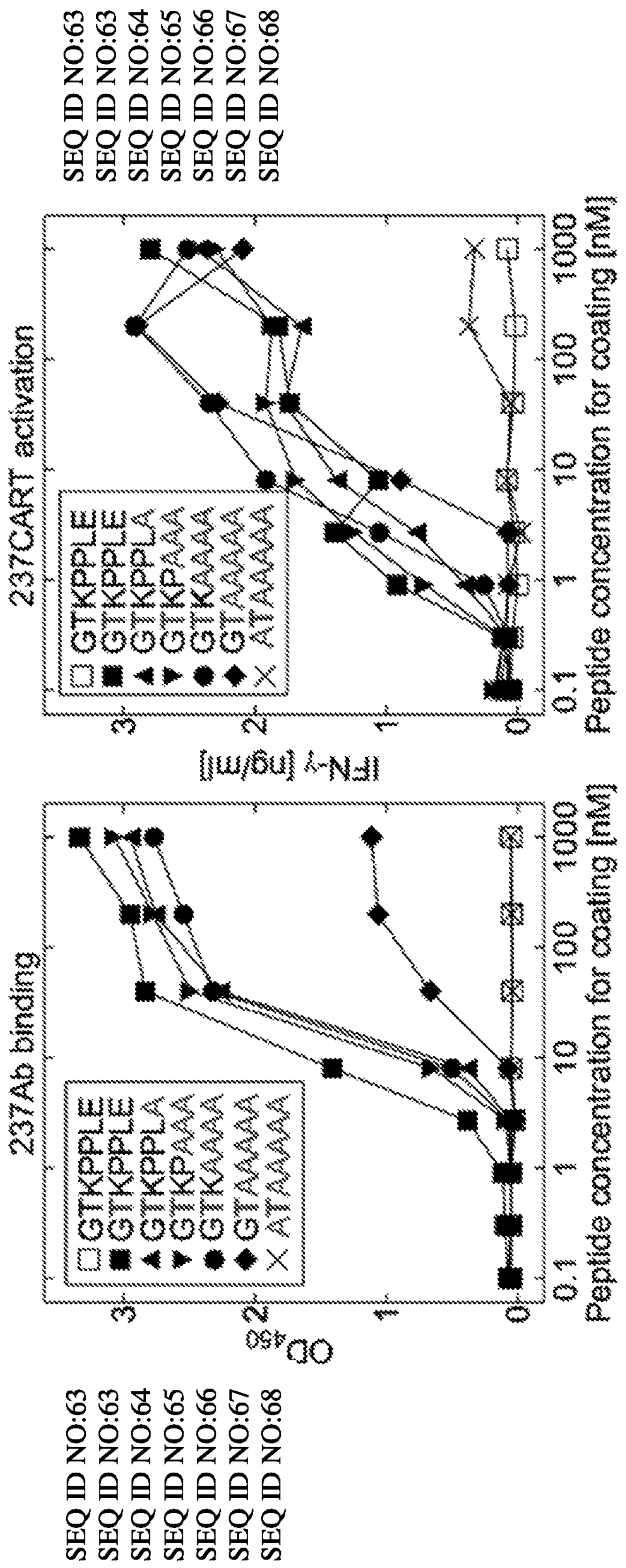
FIG. 29. 237 antibody binding and 237 CAR-T cell recognition of PDPN variants bearing multiple Ala substitutions in the 237 binding site. 237 CAR-T cells recognize a wider range of Tn-glycopeptides than was predicted by 237 antibody binding. 237 antibody binding to immobilized PDPN variants was measured by standard ELISA, wherein the PDPN variants with Tn-linked to threonine antigen (red T) contained multiple site-directed Ala substitutions of amino acid residues in the PDPN binding site for the 237 antibody. The activation of 237CART cells by the peptides was evaluated by the level of IFN-γ released after 24-hour coincubation with immobilized peptides. 237 CAR-T cells tolerated multiple Ala replacements within the epitope recognized by the 237 antibody. Biotinylated PDPN variants with increasing numbers of Ala replacements within the 237 antibody binding epitope were chemically synthesized and immobilized on streptavidin-coated plates. 237 full IgG binding to the immobilized peptides was determined by sandwich ELISA (LEFT), and 237 CAR-T cell recognition was tested by determining the level of IFN-γ release by 5000 237 CAR-T cells into the supernatant after 24-hour co-incubation with peptides immobilized on the plate surfaces. 237 CAR-T cell activation was assessed by measuring IFN-γ secretion of the CAR-T cells exposed to the immobilized PDPN variants. The negative control is the PDPN peptide without a Tn-linked threonine (black T). Increasing the number of alanine replacements of the Tn-mPDPN epitope caused more significant reductions of 237Ab binding than of 237CART cell activation.
Figure 30:
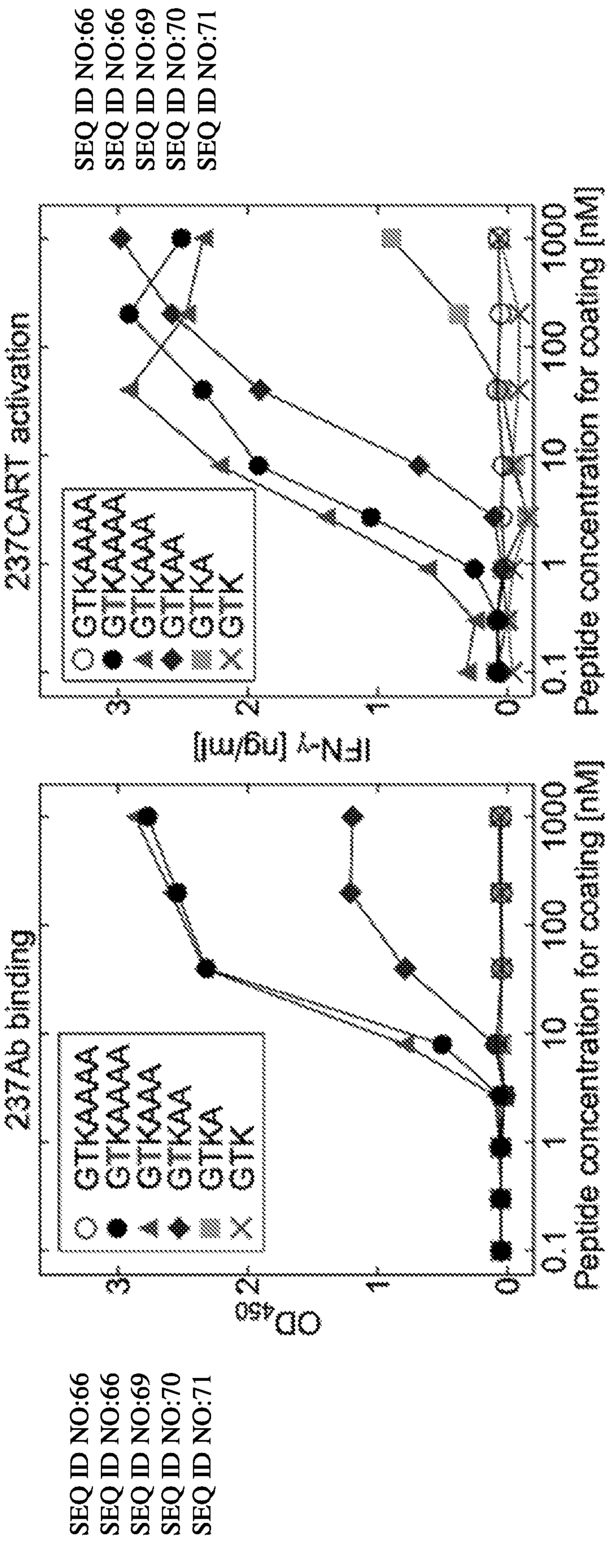
FIG. 30. 237 antibody binding and 237 CAR-T cell recognition of PDPN length variants. Gradual truncation of the Tn-mPDPN epitope beginning from the C-terminus. 237 CAR-T cells recognize a wider range of Tn-glycopeptides than what is predicted by 237 antibody binding. 237 CAR-T cell activation requires a shorter epitope than 237 antibody binding predicted. Biotinylated PDPN variants with Tn-linked to threonine antigen (red T) containing progressive truncations from the C-terminus were chemically synthesized and immobilized on streptavidin-coated plates. 237 full IgG binding to the immobilized peptides was determined by sandwich ELISA (LEFT), and 237 CAR-T recognition was tested by determining the level of IFN-gamma release by 5000 237 CAR-T cells into the supernatant after 24-hour co-incubation with peptides immobilized on the plate surface. Data presented in FIG. 29 showed that substitution of four Ala residues at the C-terminal end of the 237 antibody binding site of PDPN (GTKAAAA, SEQ ID NO:10) retained much of the capacity to induce 237 CAR-T cell IFN-γ expression exhibited by wild-type PDPN (containing the GTKPPLE (SEQ ID NO:11) binding site for the 237 antibody). This multiple Ala variant was then further modified by progressively deleting individual Ala residues from the C-terminal end of the 237 binding site and turbidimetric assays of 237 antibody binding were performed along with measurements of the induction of IFN-γ secretion levels by the 237 CAR-T cells. The negative controls are the PDPN peptides without a Tn-linked threonine (black T). Progressive truncations compromise 237Ab binding and 237CART cell recognition similarly. Mean±SEM, n=3.
Figure 44:
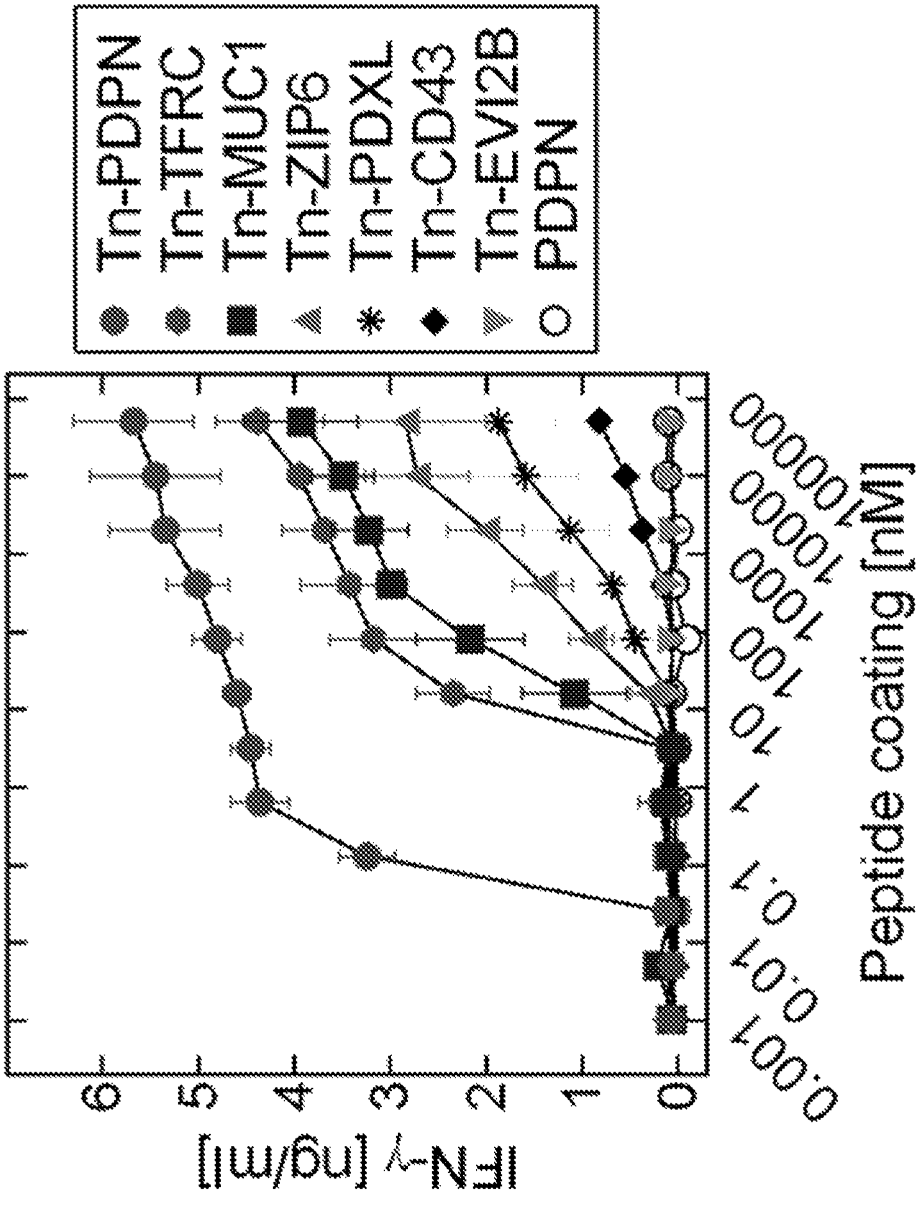
FIG. 44. 237 CAR-T cells recognize multiple independent Tn-glycoproteins on a single cancer cell. 237CAR-T cells recognize a variety of different Tn-glycopeptides. Biotinylated Tn-glycopeptides (Tn-glycosylated PDPN, TFRC, MUC1, ZIP6, EVI2B, PDXL, CD43, PCDH9, LAMP1) were chemically synthesized and immobilized on streptavidin coated plate at the coating concentration as indicated. 5000 237CAR-T cells were added to the plate and co-incubated with the immobilized peptides for 24 hours. The level of IFN-γ release into the supernatant was measured by sandwich ELISA.

One main obstacle in engineered T cell therapies is the relapse/outgrowth of antigen-loss variants due to the heterogeneous nature of the disease. Having discovered that 237 CAR-T cells could recognize COSMC mutant cancer cells without PDPN expression, the specificity of which was not even predicted by 237 antibody binding, an investigation was launched to discover what other Tn-glycopeptides could be recognized by 237 CAR-T cells. To further analyze the cross-reactivity of 237CART cells compared to the 237Ab, single or multiple alanine (Ala, A) replacements in the 237Ab-recognized Tn-mPDPN motif G(T77*Tn)KPPLEE (SEQ ID NO: 35) were made as described previously (3, 16) and incorporated herein in relevant part. The Tn-glycosylated and unglycosylated versions of the original motif, as well as single or multiple Ala replacement variants, were chemically synthesized by ElimBiopharm. Thr77 was always preceded by APLVPTQRERG (SEQ ID NO: 36) as in mPDPN (16). The N-terminal biotinylated peptides were immobilized on streptavidin-coated plates at the indicated coating concentrations (FIG. 28). 237Ab binding was determined by ELISA, and 237CART cell activation was determined by the level of IFN-γ released into medium by CART cells co-incubated with the peptides. Initially, each amino acid within the 237 antibody binding epitope was replaced by an Ala residue, one amino acid at a time (FIG. 28), and it was found that, although G76A (substituting Ala for Gly76) had the greatest impact on 237 antibody recognition, this mutation and other mutations in the 237 antibody binding epitope stimulated 237 CAR-engineered T cells. As shown in FIG. 28, the Tn on Thr77 of mPDPN was essential for 237Ab binding and 237CART cell activation. Binding of the 237Ab to peptide-coated plates was significantly reduced when Gly76 was replaced with an Ala, and single Ala replacement of two other amino acid residues caused a small reduction in binding. However, none of the single Ala replacements significantly reduced the activation of 237CART cells. Next, multiple Ala replacements in the motif were made (FIG. 29). As disclosed herein, increasing numbers of amino acids within 237 epitopes were replaced by Ala, and G76 and K78 were found to be important for 237 CAR-T recognition (FIG. 29). As shown in FIG. 29, surprisingly, even replacing 5 amino acid residues in the C-terminus of the 237Ab epitope still allowed 237CART cell activation. However, when the N-terminal Gly76 was also replaced by Ala, 237CART cell activation was compromised considerably. This contrasts to the 237Ab binding, which was already significantly diminished after substitution of the Gly76 alone. Since five C-terminal amino acid residues could be replaced by Ala while retaining activation of 237CART cells, the minimal length of the C-terminal peptide required for 237CART cell activation was investigated. Furthermore, the experimental results disclosed herein showed the peptide length required for 237 CAR-T cell activation, and found that at least two amino acid residues following the Tn-glycosylated Thr were required for efficient 237 CAR-T activation (FIG. 30). As shown in FIG. 30, the loss of the four C-terminal amino acid residues abrogated 237Ab binding as well as 237CART cell activation, and both reactions were already reduced when the three C-terminal amino acid residues were missing. The 237 CAR-T cells tolerated up to five alanine substitutions in the seven amino acid residues in the Tn-mPDPN motif recognized by the 237 antibody. Thus, these experiments demonstrate a greater permissiveness of 237CART cells than 237Ab to C-terminal Ala replacements of the G(T*Tn) KPPLEE (SEQ ID NO: 35) motif, while shortening of the C-terminal amino acids of the motif prevented activation of 237CART cells and binding of 237Ab similarly. Overall, the assay has demonstrated the broad range of Tn-PDPN variants that can be recognized by 237 CAR-engineered T cells, and its dependence on Tn-glycosylation. Furthermore, 237 CAR-T cells have been tested against multiple Tn-glycopeptide antigens naturally occurring on Jurkat cells, the recognition of which revealed 237 CAR-engineered T cells can recognize a variety of Tn-glycopeptides on a single cancer cell while remaining dependent on the COSMC mutation. Thus, 237 CAR-T cells provide specific and high-coverage approaches to solve the unmet clinical needs for cancer patients carrying the COSMC loss-of-function mutations (FIG. 44).

Figure 2:
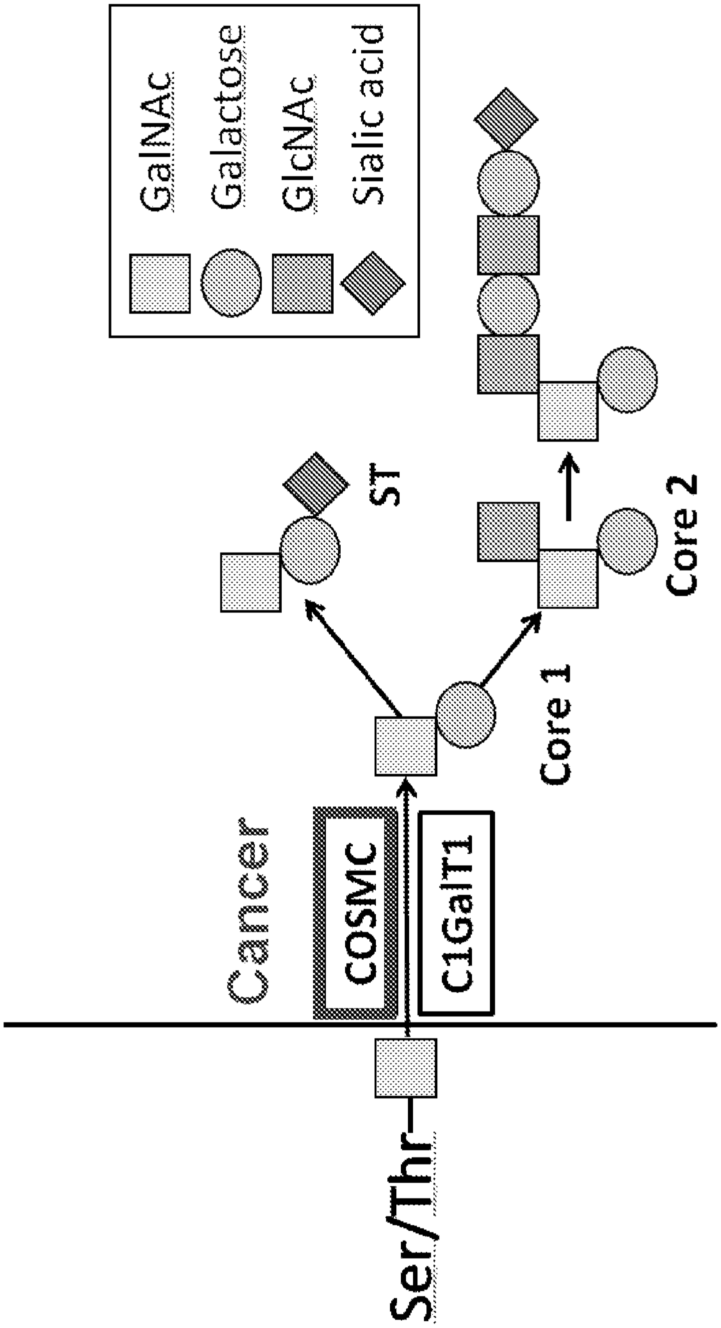
FIG. 2. Schematic depiction of the effect of COSMC dysfunctional mutations on O-linked glycosylation of peptides (i.e., glycopeptides). Tn-antigens are attractive targets for cancer treatment. The schematic illustrates how a COSMC mutation results in Tn antigen expression: O-linked glycoproteins are often overexpressed in many types of cancers, the somatic mutation of COSMC halts the O-linked glycosylation after addition of N-acetyl galactosamine (GalNAc) to the Ser or Thr residues of the glycoprotein, creating a cancer-specific epitope N-acetyl galactosamine (GalNAc)—O-Ser/Thr that are called Tn antigens.
Figure 24:
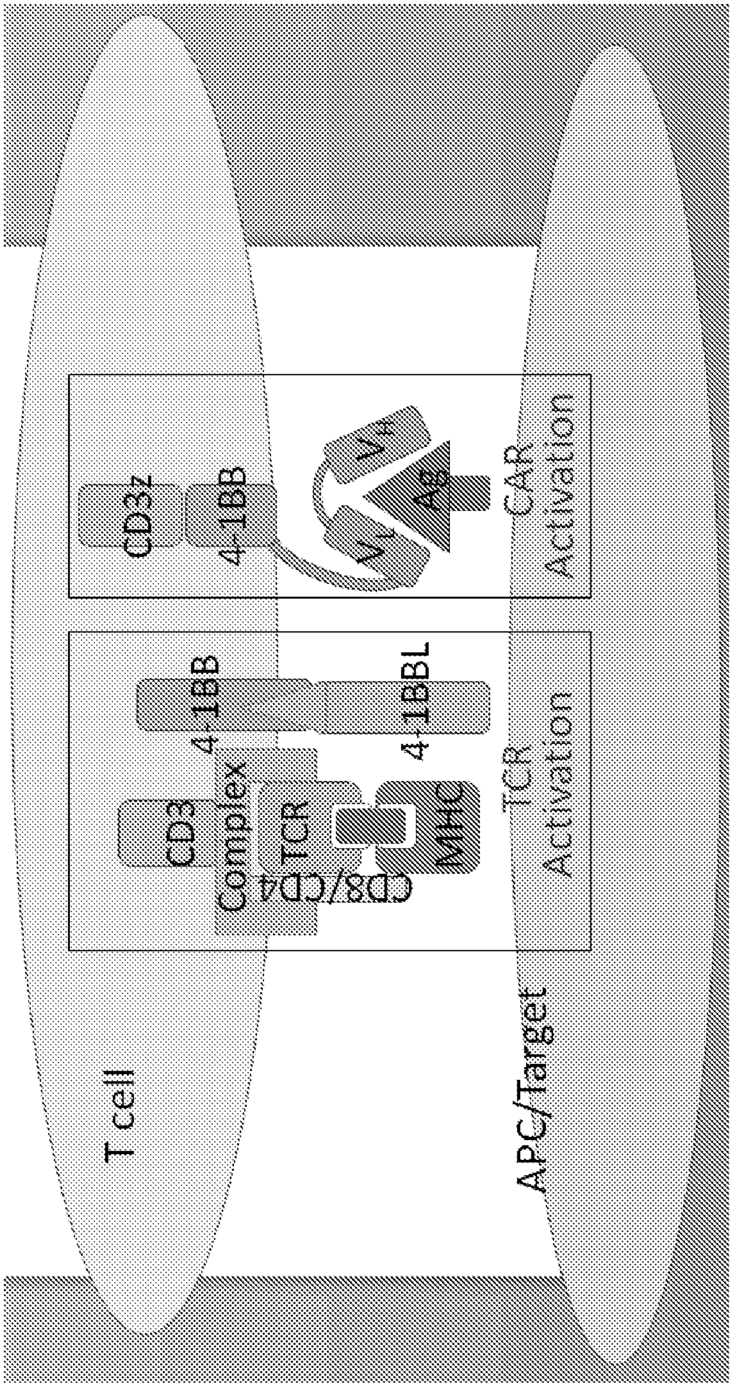
FIG. 24. Schematic comparison of antigen-TCR binding and antibody-CAR binding. Schematic illustration of the scFv-T cell signaling domain(s) structure of a CAR bound to an antigen compared to the MHC-mediated binding of an antigen to a T cell receptor.

The disclosure provides immunotherapeutics in the form of CAR molecules that specifically recognize the Tn epitope, an epitope associated with a variety of cancers. The Tn epitope arises from a modification of the glycosylation of a Threonine or Serine residue in a protein, and is schematically illustrated in FIGS. 1 and 2. The structure of the CARs of the disclosure that recognize the Tn epitope comprise a Tn-epitope recognizing domain based on the 237 single chain variable fragment (237 scFv) coupled to a T cell signaling domain, as schematically shown in FIG. 24. The Tn epitope characterized by modified glycosylation is associated with mutation in the Cosmc gene, a known protein chaperone. Survey data establishing the widespread association of Cosmc mutations, and hence Tn epitope presence, with various cancers is shown in FIG. 3.

The disclosure provides a dramatically sensitive, specific yet broadly effective immunotherapeutic approach to cancer identification and/or treatment using a chimeric antigen receptor (CAR) therapeutic based on the 237 antibody, an anti-Tn epitope antibody. Engineering the variable fragments of the 237 antibody into a CAR format revealed the surprising results of broader recognition of proteins exhibiting the modified glycosylation pattern characteristic of the Tn epitope. Significantly, the 237 CAR and its derivatives disclosed herein recognize the modified glycosylation pattern of the Tn epitope, but the epitope does not appear to include any specific peptide sequence, resulting in a CAR that recognizes the Tn epitope, known to be associated with a variety of cancers, and that recognition is not confined to proteins or peptides of any particular sequence. In addition, the data disclosed herein shows that multimerization of the soluble 237 scFv protein yielded unexpectedly increased sensitivity which makes the soluble 237 scFv, and molecular forms incorporating the soluble 237 scFv, useful as diagnostics for Tn antigen-expressing cancers. The derivatives of the 237 CAR disclosed herein also showed increased sensitivity to the Tn epitope.

The disclosure also provides methods of identifying a cancer subject amenable to anti-Tn epitope cancer therapy by obtaining a biological sample from a subject, determining the level of COSMC and/or T-Synthase in the sample, comparing the level of COSMC and/or T-Synthase in the sample to a control, and identifying the subject as a cancer subject amenable to anti-Tn epitope cancer therapy if the level of COSMC and/or T-Synthase is lower in the sample of the subject than in the control. The control is any control known in the art, including a level of COSMC and/or T-Synthase from one or more healthy individuals, regardless of when the level of COSMC and/or T-Synthase from the healthy individual(s) was or were determined. In subjects identified as cancer subjects, the relatively low level of COSMC and/or T-Synthase can be associated with a mutation in the gene encoding COSMC and/or the gene encoding T-Synthase. The method of identifying cancer subjects amenable to anti-Tn epitope cancer therapy may further comprise cancer treatment by administration of a therapeutically effective amount of a therapeutic agent according to the disclosure.

In constructing 237 CAR molecules, the Tn-epitope-recognizing domain of the CAR, based on the 237 antibody, is coupled to a T cell signaling domain. T cell signaling domains of the 237 CARs according to the disclosure include, but are not limited to, CD3ζ, CD3ζ (EBV), CD3ζ (Influenza MP-1), CD3ζ (VSV), CD3ε, 4-1BB, CD28, FCεRIγ, FcεRIγ (alloantigen), 4-1BB-CD3ζ, CD28-CD3ζ, CD28-CD3ζ (EBV), CD28-CD3ζ (Influenza), CD4-CD3ζ, CD28-4-1BB, CD4-FCεRIγ, CD28-FcεRIγ, CD28-41BB-CD3ζ, and CD28-OX40-CD3ζ.

EXAMPLES

Example 1

237 scFv Construct and Soluble 237 scFv

Figure 5:
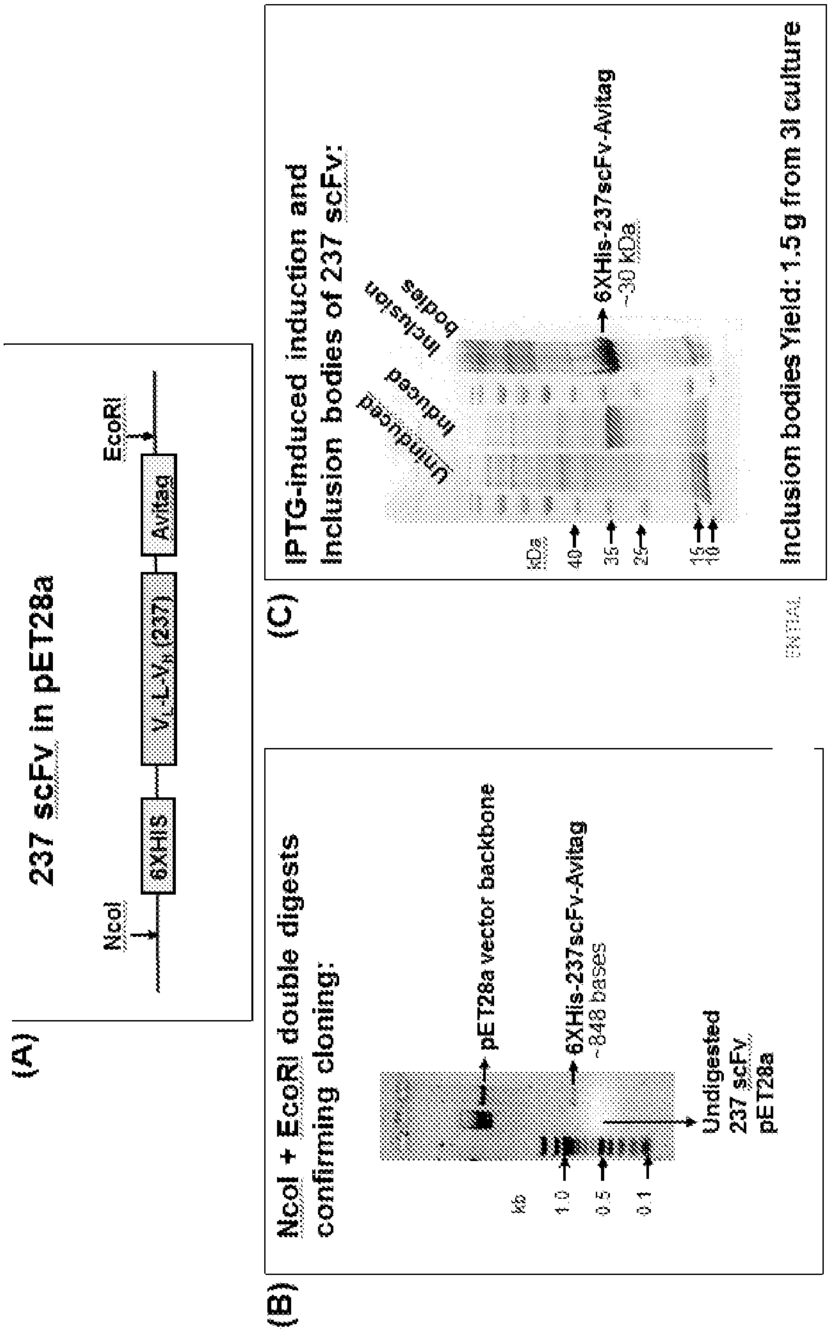
FIG. 5. Expression of 237scFv as soluble protein: Cloning in pET28a and inclusion body preparations. (A) Schematic of 237 scFv cloned with a N-terminal 6×His tag and C-terminal Avitag in pET28a is shown. (B) Restriction digestions with NcoI and EcoRI enzymes are shown to confirm cloning of 237 scFv in pET28a. (C) 237scFv-pET28a construct was transformed in *E. coli* (BL21 strain) for IPTG-induced protein expression. Lanes loaded with uninduced, induced cultures and inclusion body preparations are shown on a 4-20% SDS-PAGE gel.
Figure 6:
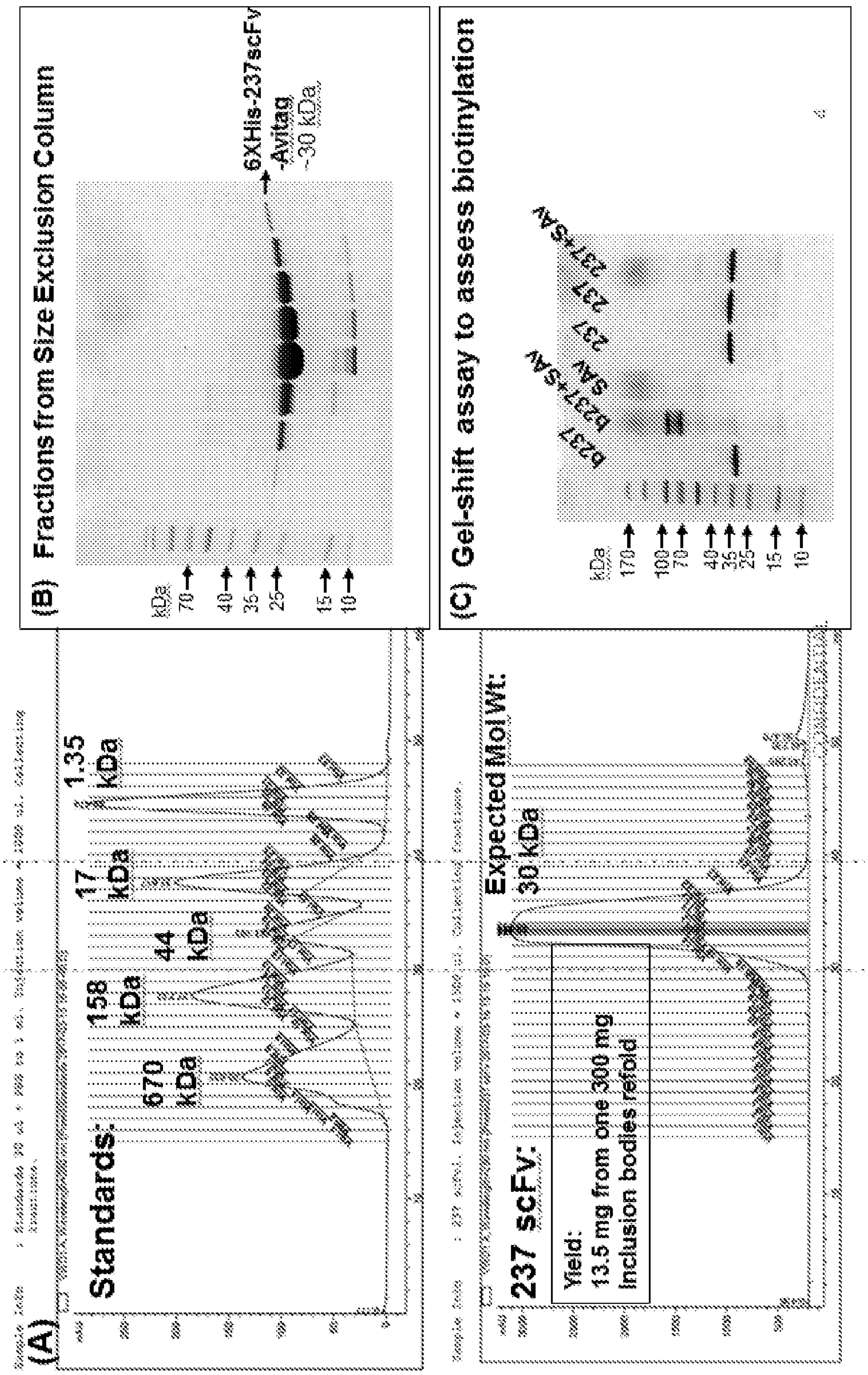
FIG. 6. Expression of 237scFv as soluble protein: Refolded 237 scFv and in vitro biotinylation. (A) Refolded 237 scFv was purified from inclusion bodies by means of Nickel-affinity chromatography, followed by size exclusion chromatography. Size-exclusion chromatograms of molecular weight standards (top) and refolded 237 scFv (bottom) are shown. 237 scFv eluted at expected molecular weight of 30 kDa. (B) Various fractions collected from size exclusion chromatography were loaded on a 4-20% SDS-PAGE. (C) C-terminal Avitag allowed biotinylation of purified 237 scFv. Gel-shift assay for monitoring biotinylation of 237 scFv is shown. Disappearance of biotinylated 237 scFv (b237) (approximately 30 kDa band) in the presence of streptavidin (SAv) indicated >90% biotinylation.

A 237 scFv was constructed from the variable regions of the light and heavy chains of the 237 antibody. As schematically illustrated in FIG. 5(A), coding regions for the light and heavy chain variable regions of the 237 antibody were juxtaposed and flanked by a 6×HIS tag nearer $V_L$ and an Avitag nearer $V_H$. An NcoI site flanking the 6×HIS tag and an EcoRI site flanking the Avitag were used to clone the construct into pET28a. The cloning was confirmed by gel sizing restriction fragment resulting from a NcoI, EcoRI double digest (FIG. 5(B)). The protein gel shown in FIG. 5(C) shows that the T7 promoter controlling scFv expression in pET28a is derepressed using IPTG (isopropyl β-D-thiogalactopyranoside). The gel reveals that the 237 scFv was purified by controlling expression of the recombinant construct, and that the scFv peptide was found in inclusion bodies that yielded 1.5 g of 237 scFv from 3 liters of culture. Inclusion bodies containing 237 scFv were refolded, resulting in an average yield of 13.5 mg refolded 237 scFv per 300 mg of inclusion bodies (FIG. 6). The purified 237 scFv was biotinylated, as revealed by gel-shift assays using streptavidin (FIG. 6(C)).

Example 2

Soluble Monomeric and Multimeric Forms of 237 scFv Bind Cancer Cells

Figure 7:
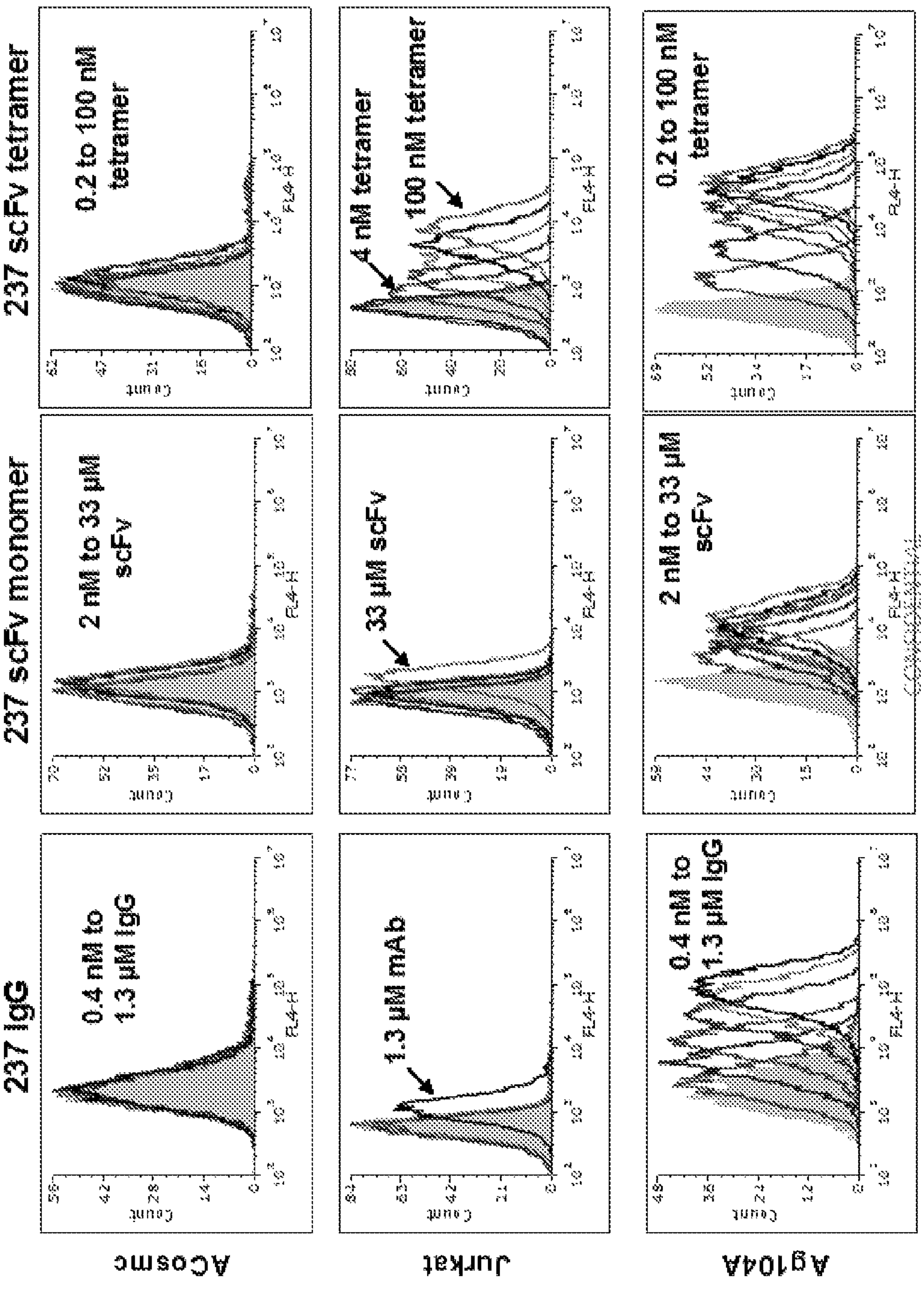
FIG. 7. Staining of various cancer lines with soluble 237 scFv in monomeric and tetrameric form. ACosmc, Jurkat or Ag104A cells were stained with various concentrations of 237 IgG or 237 scFv monomer (biotinylated) or 237 scFv tetramers (prepared with biotinylated 237 scFv and streptavidin-647), and analyzed by flow cytometry. The staining profile of cells stained with secondary reagent only is represented by the gray peak. The 237 scFv tetramers allowed sensitive detection of an unknown GalNAc-linked antigen on Jurkat, which was weakly detected with 237 IgG or scFv at micromolar concentrations.
Figure 9:
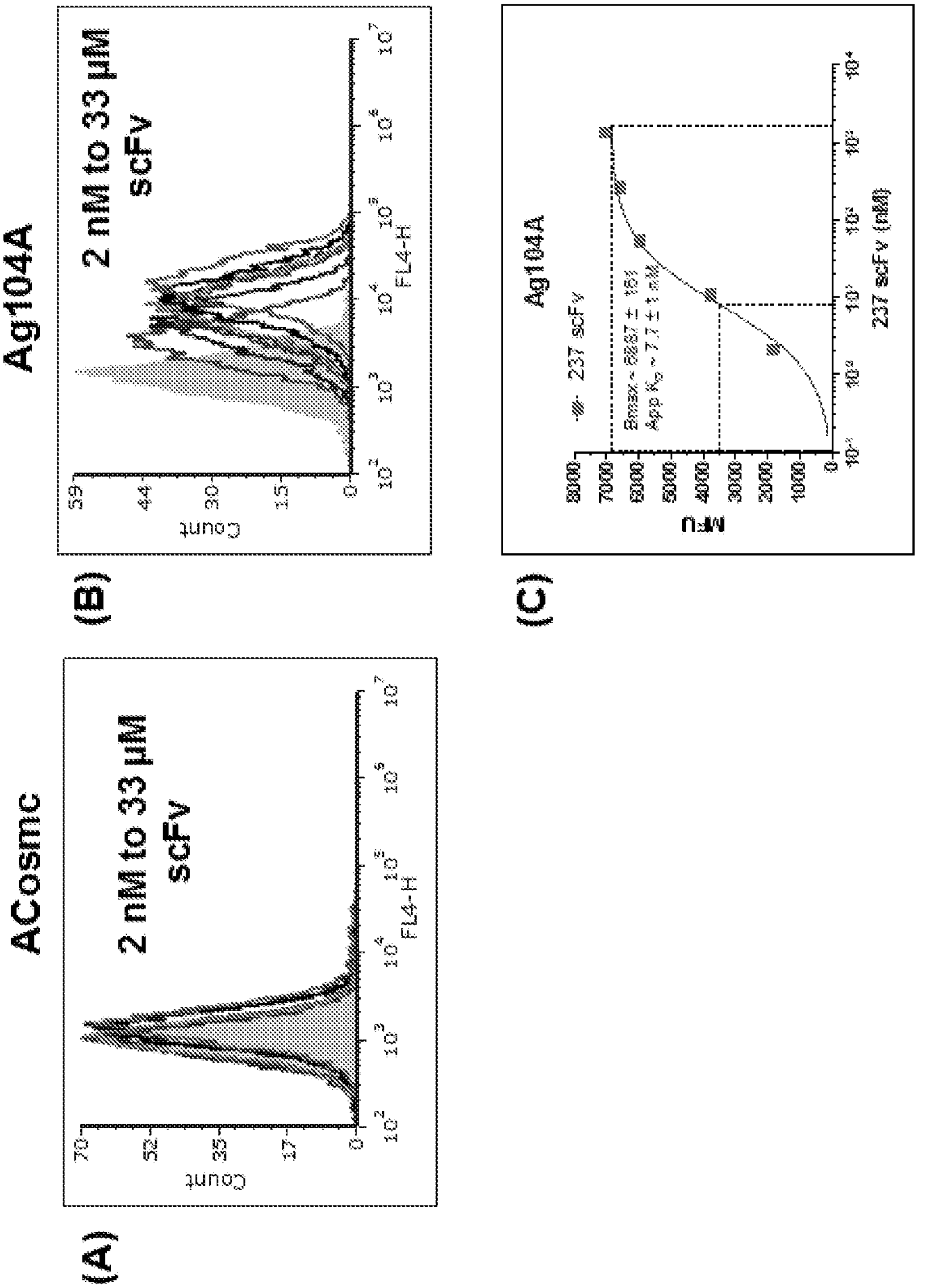
FIG. 9. Measurement of affinity of 237 scFv for cell surface PDPN (OTS-8). ACosmc (A) or Ag104A (B) cells were stained with various concentrations of 237 scFv monomer (biotinylated) followed by streptavidin-647, and analyzed by flow cytometry. The staining profile of cells stained with streptavidin-647 only is represented by the gray peak. (C) Mean fluorescence units (MFU) from (B) were plotted against 237 scFv concentration to obtain approximate dissociation constant for the binding of 237 scFv to cell surface OTS8 on Ag104A.
Figure 11:
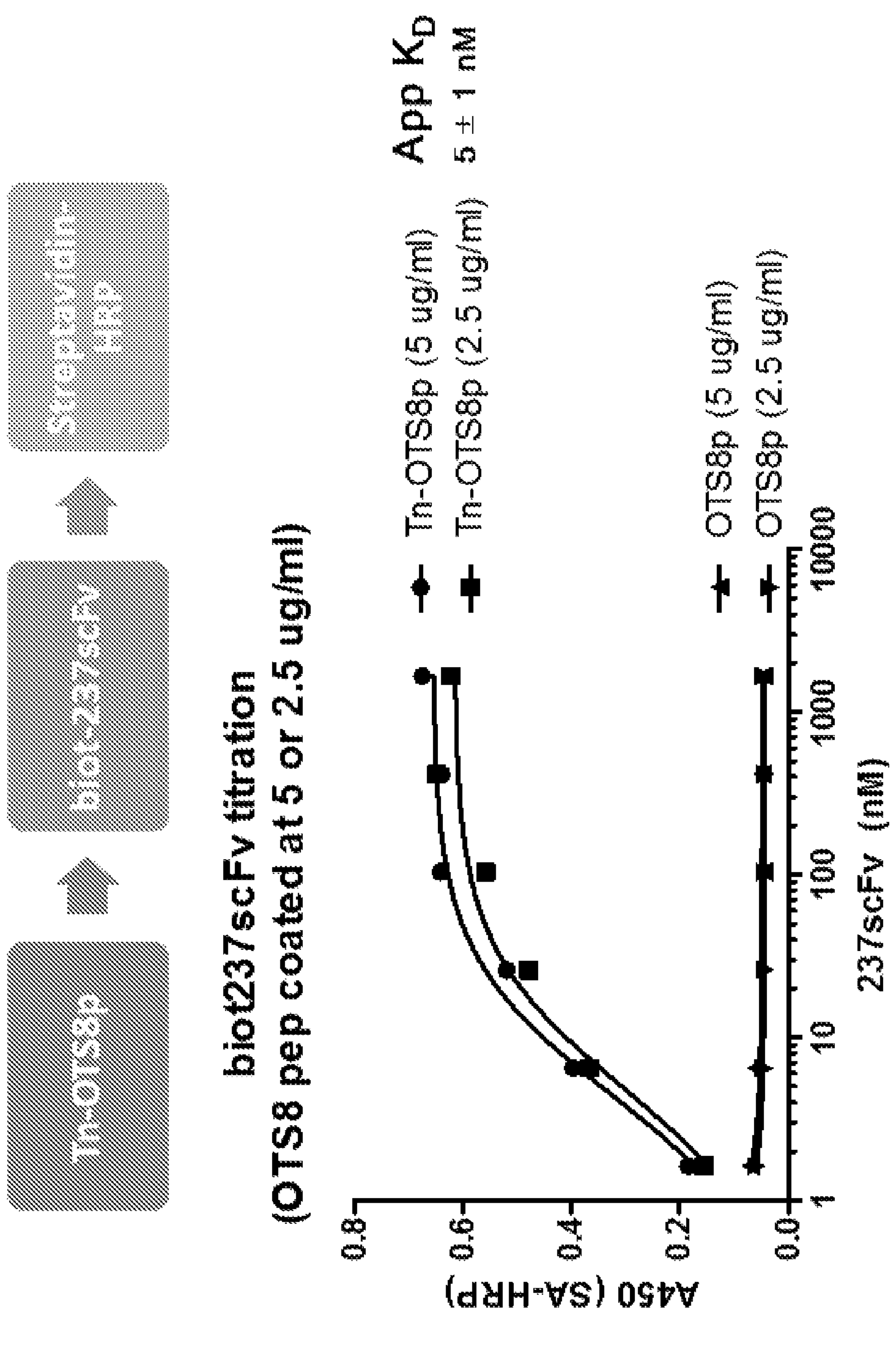
FIG. 11. Binding of soluble 237 scFv to OTS8p: scFv retains exquisite Tn specificity. OTS8 peptides (with or without Tn) were coated on an ELISA plate at 2.5 and 5 μg/ml, followed by incubation with biotinylated 237 scFv at various concentrations. Bound 237 scFv was detected using streptavidin-conjugated HRP (SA-HRP). Absorbance of HRP-catalyzed product was measured at 450 nm, and plotted against 237 scFv concentration to obtain binding curves.

Based on the premise that increased avidity would lower the detection threshold of an immunological agent, such as the 237 scFv, for the Tn epitope, multimeric forms of the 237 scFv were engineered. Towards that end, the 237 scFv coding region was cloned with a N-terminal 6×His tag (to aid in purification using a Ni-affinity column), and a C-terminal Avitag (to aid in site-specific biotinylation of the 237 scFv) in pET28a (FIGS. 5(A), (B)). Induction with IPTG allowed expression of the 237 scFv protein in *E. coli*, which could be purified to obtain high yields (FIGS. 5(C), 6(A)), and biotinylated with an efficiency greater than 90% (FIG. 6(C)). The biotinylated 237 scFv could then be tetramerized via four biotin-binding sites on streptavidin. Such fluorophore-linked tetramers could then be used to stain various cancer lines (e.g., Ag104A, ACosmc and Jurkat) (FIG. 7). The results established that 237 scFv tetramers exhibited high sensitivity (due to avidity), that facilitated the staining of the cognate Tn antigen borne on a cancer cell line (i.e., Ag104A) even at picomolar (200 pM) concentrations. In addition, the 237 scFv tetramers allowed detection of unknown antigen(s) on Jurkat cells that could only be detected weakly by micromolar concentrations of the 237 IgG antibody or monomeric scFv (FIG. 7). The data show that 237 scFv tetramers are useful in detecting the Tn antigen on cancer cells in both diagnostic and therapeutic contexts. The soluble 237 scFv monomer also allowed the first measure of the affinity of 237 scFv for surface-expressed, full-length antigen (Tn-OTS8) on Ag104A cancer cells by flow cytometry (FIG. 9). The apparent affinity of 237 scFv toward full-length protein was 8 nM, which was 17-fold higher than the reported affinity of the 237 IgG Fab toward the Tn-OTS8 peptide (3) supporting the view that conformational differences existed between the OTS8 full-length protein (i.e., Podoplanin) and the Tn-OTS8 peptide (i.e., the region of Podoplanin linked to the Tn epitope). We also performed an ELISA-based assay to measure the binding of 237 scFv toward Tn-OTS8 peptide (KAPLVPTQRERGT (GalNAc)KPPLEELSTSATSDHDH; SEQ ID NO:12 (4)). Although this assay is not a true measure of affinity due to the binding of 237 scFv to several molecules of peptide adsorbed on an ELISA plate, the results indicated that the binding was Tn-dependent, as the scFv didn't bind to OTS8 peptide that didn't have a Tn moiety attached to it (FIG. 11).

Three cancer cell lines, i.e., ACosmc cells, Jurkat cells, and Ag104A cells, were exposed to a monomeric form of 237 scFv labeled with biotin or a tetrameric form of 237 scFv labeled with biotin and multimerized by adding streptavidin-647. Following exposure to the monomeric or tetrameric form of 237 scFv, cells were subjected to flow cytometry and the results are presented in FIG. 7. The results establish that the monomeric form of the 237 scFv binds to Ag104A and weakly to Jurkat cancer cell lines. In addition, the tetrameric form of the 237 scFv binds much more strongly to Ag104A and Jurkat cancer cell lines and, notably, the tetrameric form of the 237 scFv exhibited significantly greater sensitivity to Jurkat cancer cells compared to the monomeric form of the 237 scFv (FIG. 7). ACosmc is a mutant cell line derived from Ag104A, which has the Cosmc mutation rescued. Hence, this cell line would express very low (if any) levels of Tn antigen, and is therefore useful as a negative control for this experiment.

Figure 8:
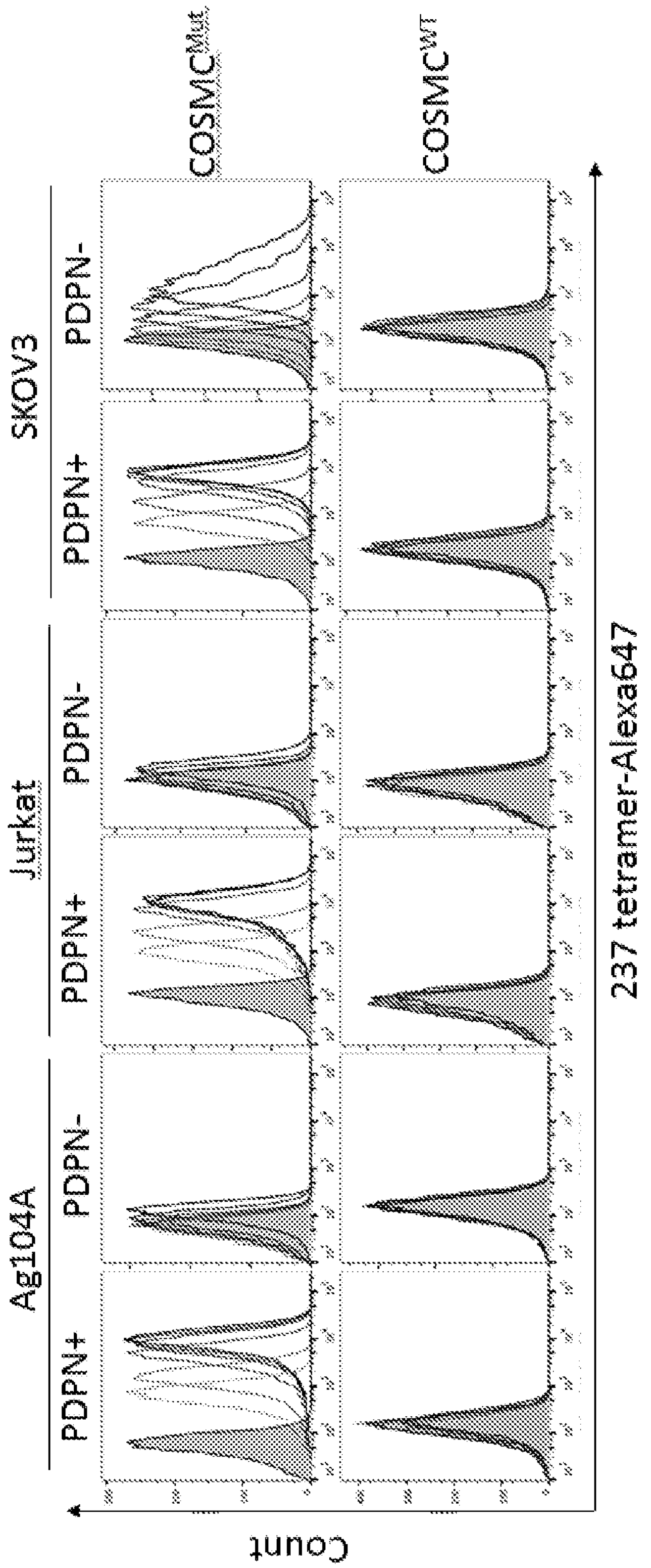
FIG. 8. Characterization of 237 scFv tetramer binding to target cells. Alexa 647-labeled 237 scFv tetramer was exposed to three cells lines, i.e., Ag104A, Jurkat and SKOV3 cells expressing a COSMC mutant ($COSMC^{Mut}$) or the wild-type COSMC ($COSMC^{WT}$) in either the presence ($PDPN^+$) or absence ($PDPN^-$) of podoplanin.

The tetrameric form of the 237 scFv was then subjected to binding assays using the cancer cell lines Ag104A, Jurkat and SKOV3 having one of the following genetic backgrounds: $Cosmc^+/PDPN^+$, $Cosmc^+/PDPN^-$, $Cosmc^-/PDPN^+$, and $Cosmc^-/PDPN^-$. The results showed that the tetrameric scFv specifically bound to each of the three cancer cell types exhibiting a $Cosmc^-$ phenotype, regardless of the PDPN genotype, but did not detectably bind to $Cosmc^+$ cancer cells, regardless of PDPN genotype (FIG. 8). Thus, the tetrameric 237 scFv is specific for the $Cosmc^-$ cancer cells characteristic of a variety of cancer types.

Figure 38:
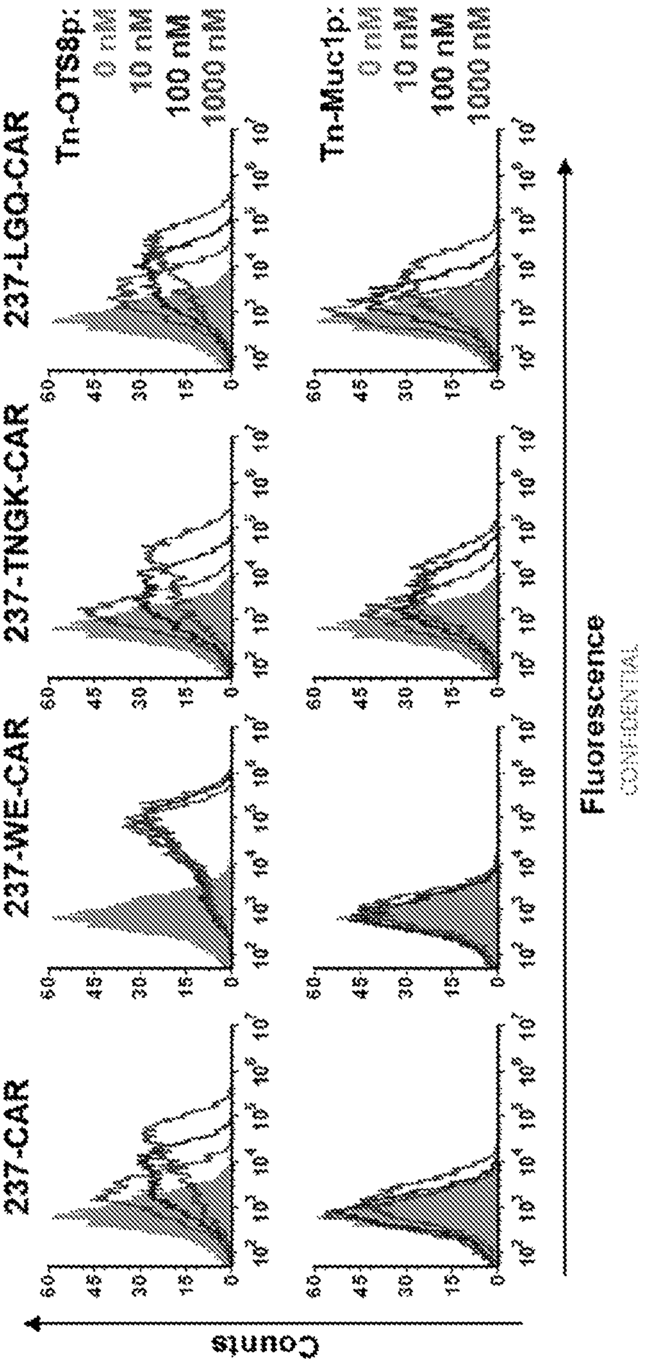
FIG. 38. Expression of WE or TNGK or LGQ mutation in the 237 CAR format. Mutations in 237 scFv obtained from either Tn-OTS8p sorts (WE variant), or Tn-Muc1p sorts (TNGK or LGQ variant) of 237 libraries were introduced in 237scFv-CD28-CD3zeta CAR. Total T cells from C57BL/6 mice were transduced with the 237-CAR or 237-WE-CAR or 237-TNGK-CAR or 237-LGQ-CAR variant. Transduced T cells were stained with various concentrations of Tn-OTS8 or Tn-Muc1 biotinylated peptides to assess binding to each peptide.
Figure 39:
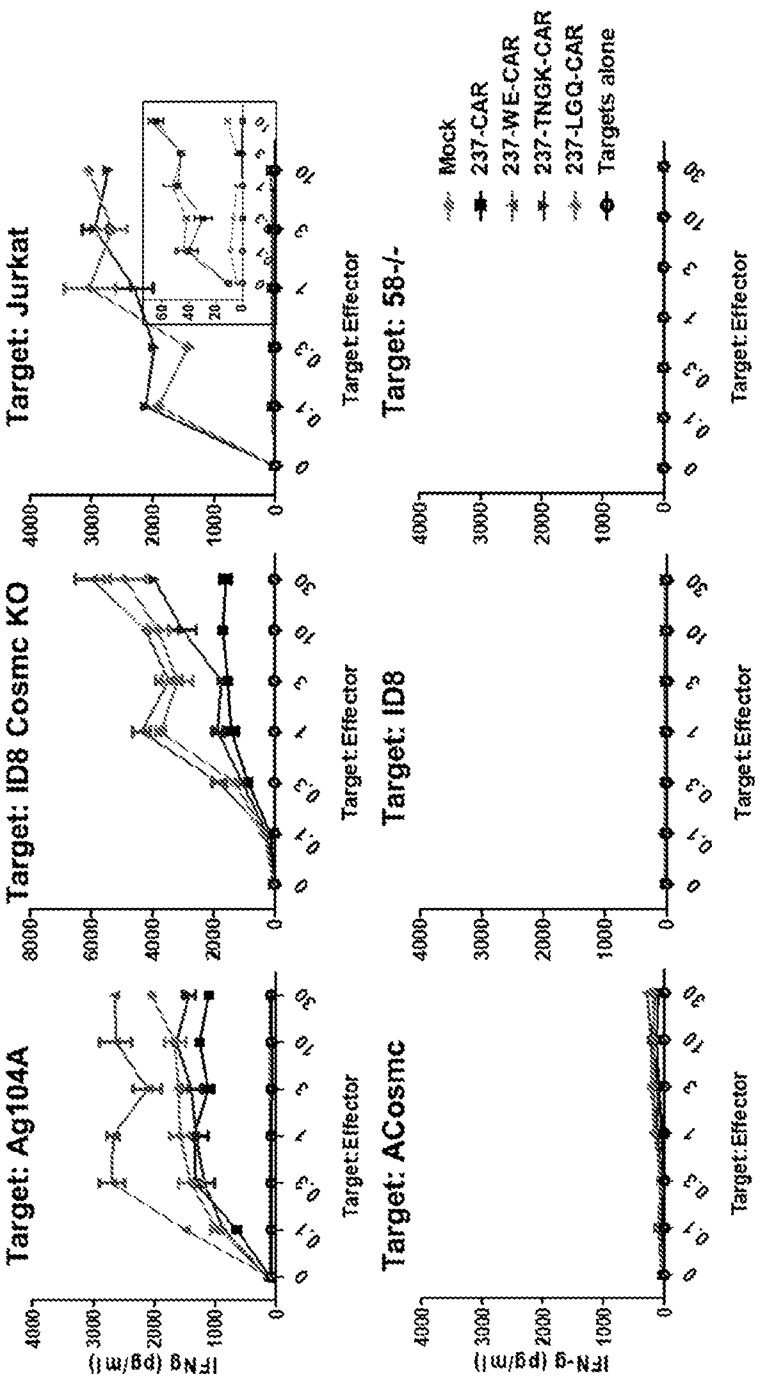
FIG. 39. Activation of T cells transduced with 237-CAR or 237-WE-CAR or 237-TNGK-CAR or 237-LGQ-CAR upon co-culture with various Tn antigen expressing cancer cell lines. Total T cells from C57BL/6 mice were transduced with 237-CAR or 237-WE-CAR or 237-TNGK-CAR or 237-LGQ-CAR. Transduced cells were separately co-cultured with Tn antigen expressing target cells (Ag104A or ID8 Cosmc KO or Jurkat, in top panel) or with control cell lines (ACosmc or ID8 or 58−/−, in bottom panel), for 24 hours at 37° C., 5% CO2 at various target:effector (T:E) ratios. The quantity of IFN-γ released in the supernatants under each co-culture condition was measured by standard ELISA assay.

In another experiment, the high affinity CAR (237-WE-CAR) and wild-type CAR transduced T cells were titrated with various concentrations of Tn-OTS8 peptide and Tn-Muc1 peptide (FIG. 38). As expected, the wild-type 237-CAR exhibited dose-dependence for binding to 10 nM to 1 μM Tn-OTS8 peptide, while the high affinity CAR (237-WE-CAR) bound equally well to the entire concentration range tested because of its high affinity for Tn-OTS8p. Unexpectedly, wild-type 237-CAR was noted to also bind to high concentrations of Tn-Muc1p. However, since the high affinity 237 mutant (237-WE-CAR) was selected for binding to Tn-OTS8p, it did not acquire binding to another Tn-linked ligand, Tn-Muc1p. The activities of wild-type and high-affinity CARs were then compared against a variety of cell lines in activation assays and secreted IFNγ was measured (FIG. 39). As shown, the high affinity CAR (237-WE-CAR) resulted in better recognition of, and activation with, murine Ag104A and ID8 Cosmc KO cell lines, compared to the wild-type. However, both CARs showed similar activity with Jurkat (a human cell line) that lacks murine OTS8. Because ACosmc, ID8 and 58−/− cell lines contain wild-type Cosmc, no activity was seen with either CAR. Hence, these cell lines served as good controls indicating specificity of 237-CARs toward Tn-linked antigens only. Although the wild-type 237-CAR and 237-BiTE are known to kill Tn-antigen bearing target cell lines, the activation data with the 237-WE-CAR indicate that the higher affinity forms are surprisingly more efficacious.

As noted, the binding affinity of the 237 scFv for cancer cells was investigated using conventional binding assays and flow cytometry to detect results. Various concentrations of biotinylated monomeric 237 scFv were exposed to ACosmc cells or Ag104A cells. Subsequently, streptavidin-647 was added and the binding was analyzed by flow cytometry. The results showed that 2 nM to 33 μM 237 scFv resulted in detectable binding to the Ag104A cancer cell line, but not to the Cosmc rescue cell line ACosmc (FIG. 9). The mean fluorescence units (MFU) of the binding of the 237 scFv to Ag104A cells was graphed as a function of the 237 binding concentration to reveal an approximate dissociation constant $K_D$=7.7±1 nM for 237 scFv binding to the OTS-8 PDPN epitope (FIG. 9). The contacts involved in the binding of the 237 scFv to the OTS-8 PDPN epitope are shown in FIG. 22 (3).

Example 3

The 237 Antibody Recognizes Podoplanin but the 237 CAR-T Cell has a Broader Activity Toward Multiple Tn-Linked Antigens The murine Tn-podoplanin (Tn-mPDPN)-specific antibody 237, when made into the single-chain CAR format and expressed on T cells, eradicated human cancer that lacked Tn-mPDPN. The 237 antibody was characterized in an immunostaining study involving an anti-Tn antibody and an anti-Podoplanin (anti-PDPN) antibody as controls. Cosmc encodes a chaperone for the T-synthase essential for elongation of glycans beyond the initial Tn-structure. Ag104A is a murine sarcoma cell line that carries a Cosmc null mutation. It results in Tn-glycosylation of all O-linked glycoproteins on the cell surface, including murine podoplanin (PDPN). For the Ag104A cell line, a PDPN-negative variant was made by CRISPR-Cas9 knockout of Pdpn; both this variant and the parental Ag104A cell line were reconstituted with wild-type Cosmc to generate the two additional variants with normal glycosylation. For the Jurkat cell line, a human T cell lymphoma cell line that carries a natural Cosmc null mutation, a Cosmc wild-type variant was made by Cosmc transduction; both the Cosmc wild-type and the parental Jurkat cell lines were transduced with Pdpn to make the two murine PDPN-expressing variants. For the SKOV3 cell line, a human ovarian cancer cell line with normal COSMC function, a Tn-glycosylated variant was made by CRISPR-Cas9 knockout of Cosmc; both the Cosmc knockout and the parental SKOV3 cell lines were transduced with Pdpn to generate the two murine PDPN-expressing variants. Each cell line was separately stained with each of the three primary murine monoclonal antibodies (mAbs) indicated in FIG. 4 (anti-Tn antibody, anti-murine PDPN antibody, 237 antibody), followed by goat-anti-mouse Ig-APC as secondary antibody. The level of monoclonal antibody binding to the cell surface is presented as the binding ratio of the MFI of samples stained with both primary and secondary antibodies divided by the MFI of samples stained with secondary antibody alone. The results, shown in FIG. 4, establish that the anti-Tn antibody bound to murine Ag104A cells, human Jurkat cells, and human SKOV3 cells harboring a mutant Cosmc gene at binding ratios about 100-fold greater than the binding to the extracts of such cells in a wild-type Cosmc background. The anti-murine PDPN antibody bound to extracts of murine Ag104A, human Jurkat, and human SKOV3 cells harboring wild-type Pdpn, regardless of Cosmc genotype, about 100-fold greater than the binding to these cell extracts obtained in a $Pdpn^-$ genetic background. The 237 antibody, in contrast, selectively bound to extracts of murine Ag104A, human Jurkat, and human SKOV3 cells that were $PDPN^+$, $Cosmc^-$ with a binding ratio in excess of 100-fold over the binding to extracts of cells that were $PDPN^-$ and/or $Cosmc^+$ (FIG. 4).

Figure 22:
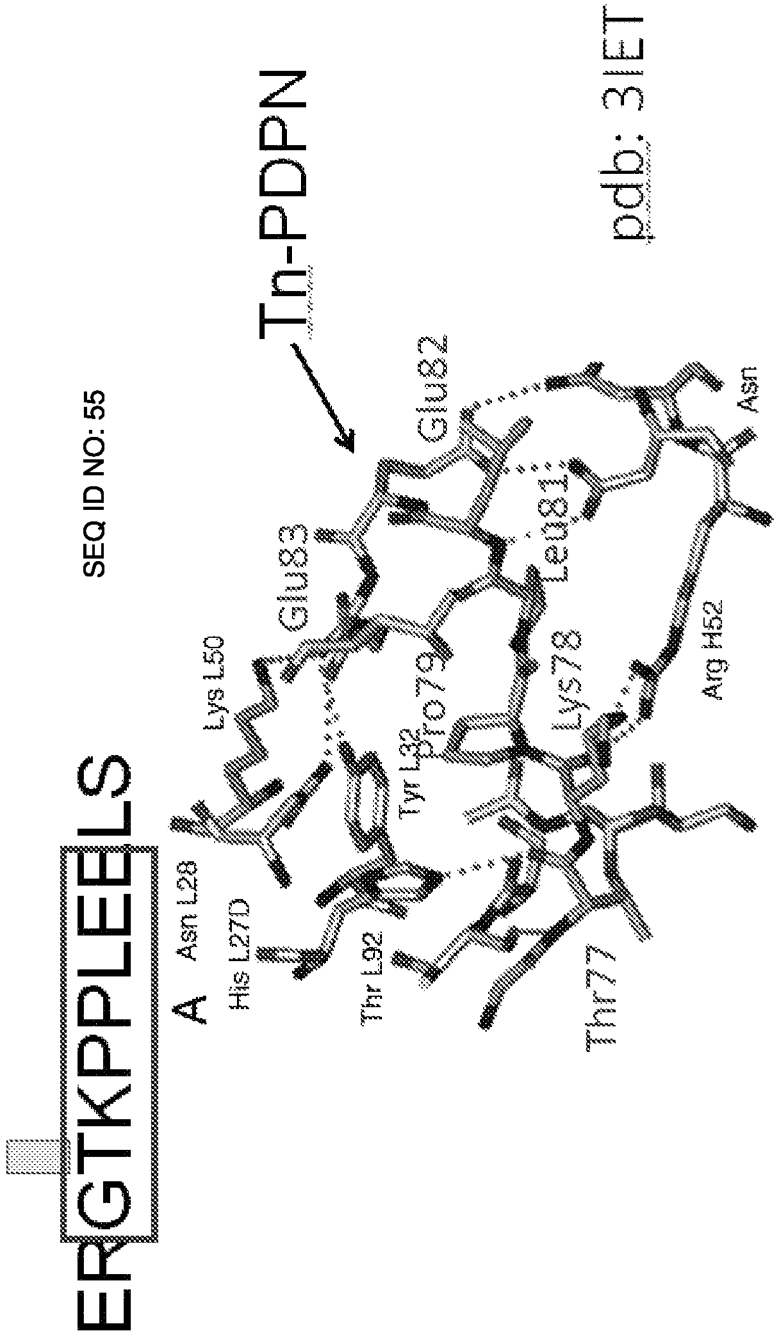
FIG. 22. Structure of the 237 antibody binding site for Tn antigen. Three-dimensional x-ray crystallographic depiction of the 237 antibody binding site for Tn-PDPN, i.e., Tn-Podoplanin. The region of Podoplanin bearing the Tn antigen is provided, i.e., GTKPPLEE (SEQ ID NO: 18), with the T residue hypoglycosylated to reveal the Tn antigen.

Analysis of the binding site interactions of PDPN and the 237 antibody led to the identification of a PDPN epitope of eight amino acids, as indicated in the inset to FIG. 22. The second amino acid in that epitope is a Threonine residue that is O-glycosylated and available for the formation of the Tn epitope in a $Cosmc^-$ background.

Example 4

CAR-T Cells Recognize Cowie Cancers Independent of Podoplanin Binding

Figure 46:
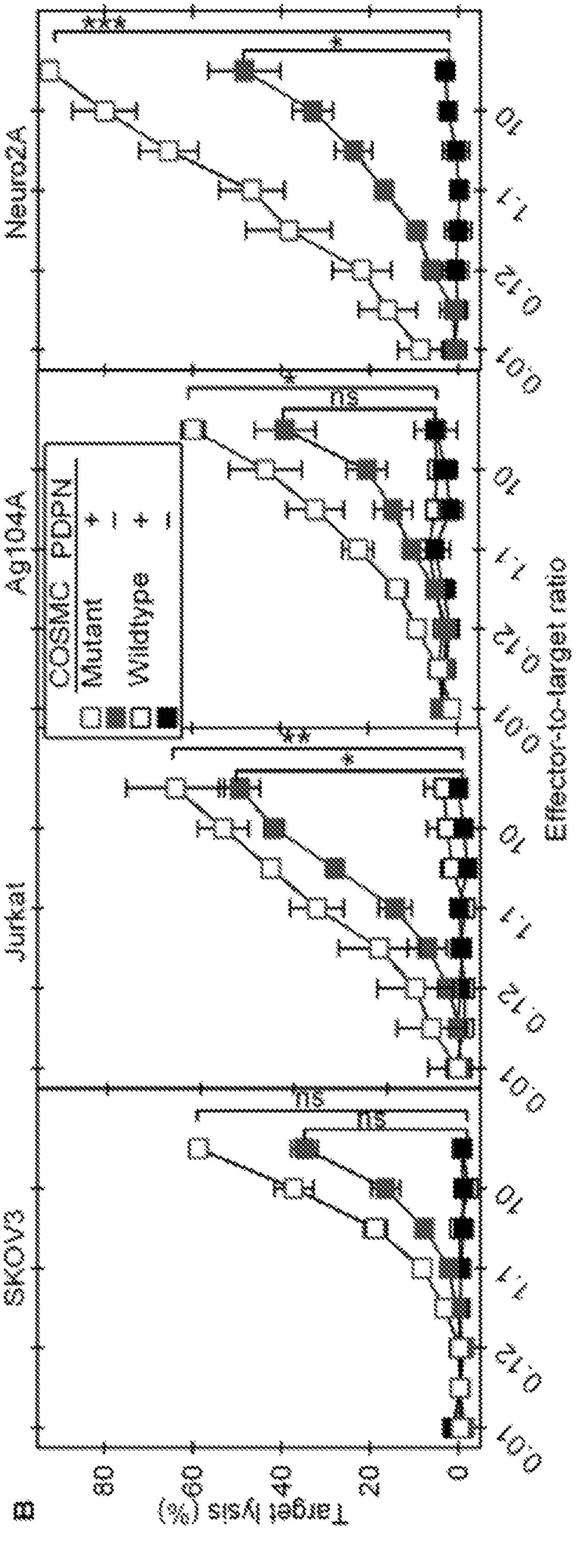
FIG. 46. 237 CART cells recognize preferentially, but not exclusively, Tn-mPDPN-expressing COSMC mutant cancers.
Figure 47:
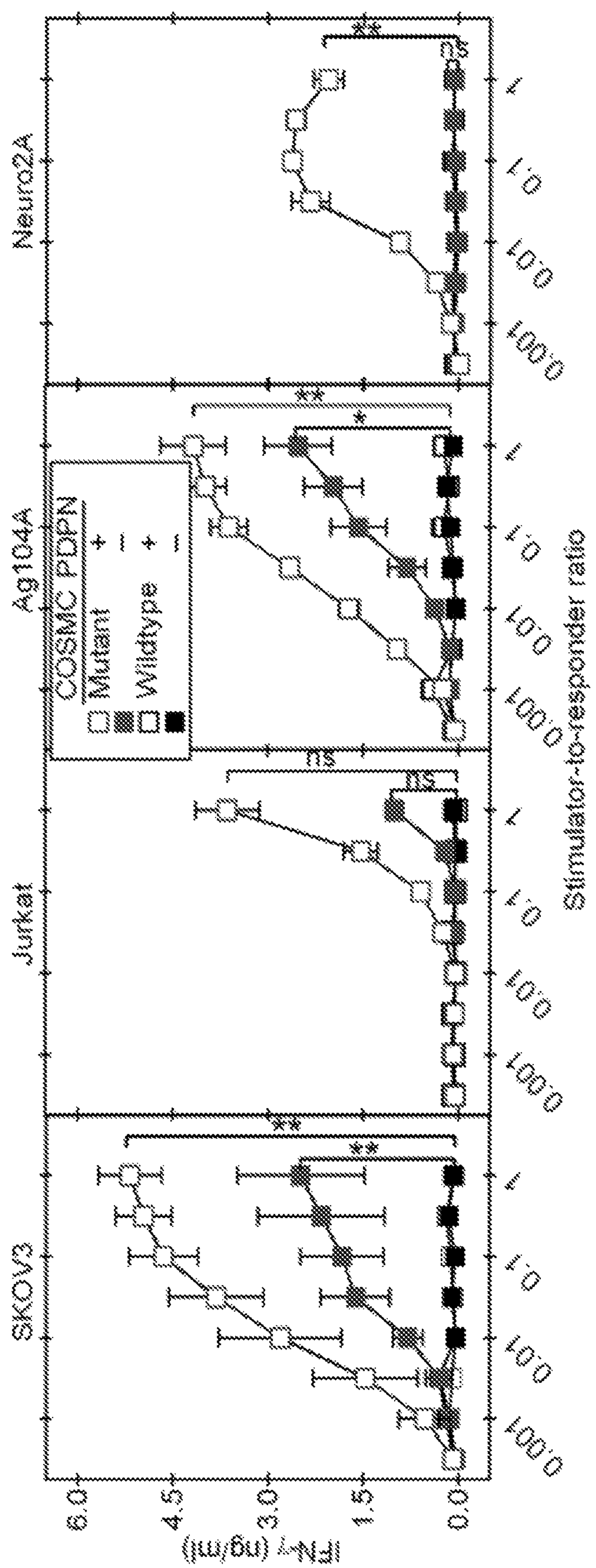
FIG. 47. The level of 237CART cell activation was determined by target lysis in a 4.5-hour $^{51}Cr$ release assay; and by IFN-γ release into the medium after a 24-hour coincubation of 237CART cells with the target cells. Mean±SEM, n=3.

Because of the discrepant reactivities of 237CART cells and 237Ab, the specificities of these two reagents for cell lines expressing or lacking Tn-mPDPN or COSMC function were compared. 237Ab selectively bound only cell lines expressing mPDPN and lacking COSMC. The 237Ab neither bound COSMC wild-type cell lines with normally glycosylated mPDPN nor COSMC-mutant cell lines lacking mPDPN expression. The ability of higher concentrations of the 237Ab to predict the cross-reactivity of the 237CART cells was examined. In contrast to the 237 antibody, the host range for the 237 CAR-T cell isn't limited to cells that are PDPN. An experiment was performed to determine the CAR-T cell effector to cancer target ratio. 237 CAR-T cells lyse COSMC null cell lines even in the absence of murine PDPN expression. 5000 $^{51}Cr$-labeled target cells per well of a 96-well plate were incubated for 4 hours with 237 CAR-T cells at the indicated effector-to-target ratio. The level of $^{51}Cr$ release into the medium by CAR-T-exposed targets (experimental release) was compared to the level of release in the absence of CAR-T cells (spontaneous release). For maximum release, targets were lysed by ZAP-OGLOBIN II. The percentage of specific lysis was calculated by the formula: % cytolysis=[(experimental release−spontaneous release)/(maximum release−spontaneous release)]×100. Spontaneous release was less than 15% of maximum release. 237 CAR-T cells were brought into contact with Ag104A, Jurkat or SKOV3 cells, and the percent cytolysis induced by the CAR-T cells was monitored at CAR-T cell:cancer cell ratios of 0.03:1, 0.33:1, 3.3:1 and 30:1. As shown in FIG. 25, $Cosmc^-$ derivatives of all three cell lines were susceptible to CAR-T cell-induced lysis. Further, the Figure shows that $Pdpn^+$ cells were more susceptible to CAR-T cell-induced lysis than $Pdpn^-$ cells for all three cell lines (i.e., Ag104A, Jurkat, and SKOV3 cells), but cancer cells remained susceptible to 237 CAR-T cell-induced lysis regardless of Pdpn genotype. The results were dramatically different for Ag104A, Jurkat and SKOV3 cells that were $Cosmc^+$. Regardless of Pdpn genotype, CAR-T cells failed to induce appreciable lysis of $Cosmc^+$ Ag104A, Jurkat or SKOV3 cells at any CAR-T cell:cancer target ratio (FIG. 25). Binding was also tested in Neuro2A cells (FIG. 46 and FIG. 47). Neuro2A is a spontaneous murine cancer cell line lacking COSMC due to somatic cancer-specific Cosmc null mutations and naturally lacks mPDPN. mPDPN-expressing Neuro2A was made by retroviral transduction of Pdpn. Even at the highest concentration (3000 nM) of the 237Ab, the staining of COSMC-mutant cancers lacking mPDPN expression was negligible. By contrast, 237CART cells clearly recognized COSMC-mutant cancers lacking mPDPN expression, even though COSMC-mutant cancer cells expressing mPDPN were preferentially recognized (FIG. 46 and FIG. 47). Thus, the 237Ab binding specificity would not have predicted the expanded 237CART cell reactivity to other COSMC mutant cancers lacking mPDPN expression. Recognition by 237CART cells requires the Tn carbohydrate moiety but tolerates extensive changes in the peptide backbone.

IFNγ is a cytokine produced by various T cells that is involved in innate and adaptive immune responses, as well as in cancer cell surveillance. Recent data indicate that IFNγ has pro-cancer as well as anti-cancer effects. An experiment was designed to examine whether varying the ratio of IFNγ level (ng/ml) to CAR-T cells (cell count) would influence the level of cytolysis in Ag104A, Jurkat and SKOV3 cells. As noted in FIG. 25, 237 CAR-T cells are stimulated by Cosmc null cell lines in activation assays to produce IFN-γ even in the absence of murine PDPN expression (FIG. 26). 5000 237 CAR-T cells per well of a 96-well plate were incubated for 24 hours with cancer cells as stimulators at the indicated ratio. The level of IFN-γ release into the supernatant was measured by sandwich ELISA. The data presented in FIG. 26 reveal that 237 CAR-T cells recognize $Cosmc^-$ cancer cells regardless of whether those cancer cells are expressing PDPN.

An experiment conducted in vivo in mice yielded consistent results. Cohorts of immunocompromised mice were injected with parental Jurkat cells, Pdpn-transduced Jurkat cell derivatives, or $Cosmc^+$, CD19-transduced Jurkat cell derivatives. Each of the three groups of mice were then sub-divided into three groups, with each group receiving treatment in the form of 237 CAR-T cells, CD19 CAR-T cells, or phosphate-buffered saline as a control treatment. Five million of each of the Jurkat cell variants, as indicated, were i.v.-injected into each NSG mouse. After Jurkat leukemia had established in the host 14 days post-transplantation, 5 million 237 CAR- or CD19 CAR-transduced OT1Rag/KO T cells were administered via i.p. injection. Injection of the same volume of PBS was used as negative control. Disease progression was followed weekly by bioluminescence (luciferase), as described in (138). Mice were monitored for 98 days following treatment, and the results shown in FIG. 27 establish that 237 CAR-T cell therapy is effective against Jurkat cancer cells regardless of Pdpn genotype, but the effectiveness of 237 CAR-T cells is diminished in cancer cells that have wild-type Cosmc. Thus, 237 CAR-T cell therapy is effective for $Cosmc^-$ cancers, regardless of PDPN genotype.

Example 5

237 scFv Mutagenesis and Characterization of 237scFv Variants

Rational Design of 237 scFv Variants

Figure 12:
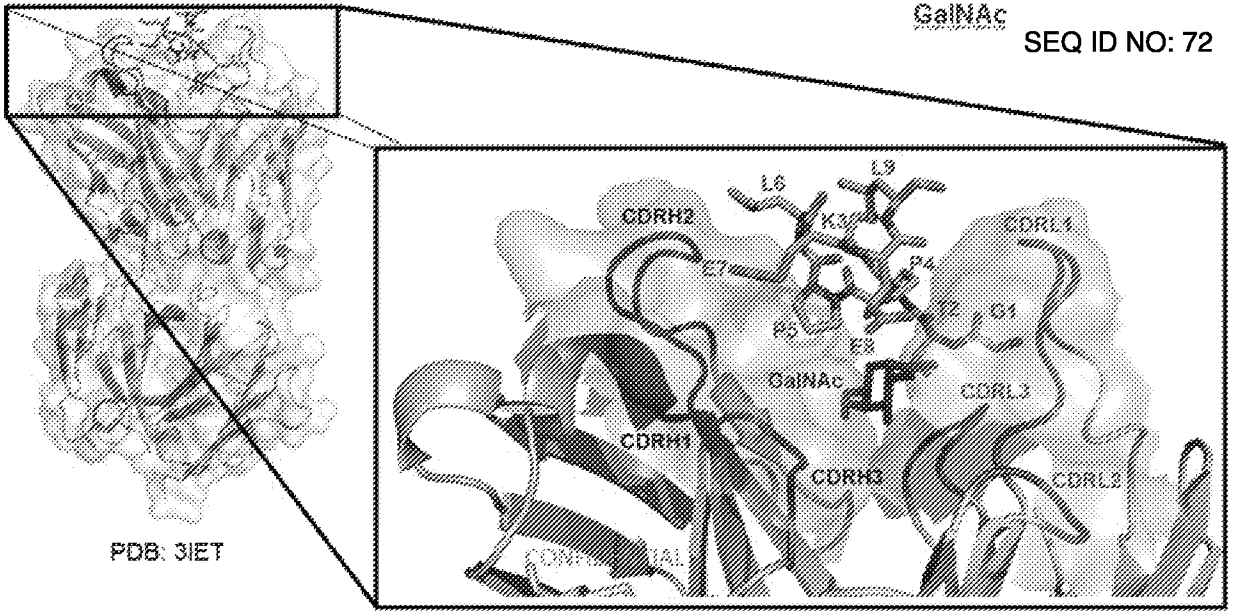
FIG. 12. Analysis of the structure of the 237 monoclonal antibody with the OTS-8 glycopeptide for rational design of 237 scFv mutated libraries. Crystal structure of 237 IgG with OTS-8 glycopeptide (PDB: 3IET) (3) was analyzed in Pymol to guide rational design of 237 scFv mutated libraries. Residues in complementarity determining regions (CDRs) of both light and heavy chains (CDRL1, L2, L3 and CDRH1, H2 and H3 respectively) that were in proximity to the sugar (GalNAc) (red) or the peptide (green) or both, were selected to make the libraries (3).

The promise of 237 scFv as the targeting moiety in an anti-cancer CAR-T cell led to efforts to develop 237 scFv variants using rational design. Rational design of the variants was based on the structure of the 237 antibody interaction with the OTS-8 glycopeptide, as illustrated in FIG. 12. Apparent from the Figure is the interaction of the 237 antibody with the OTS-8 amino acids in addition to the glycosylation pattern on the Thr residue at position 2 of the OTS-8 peptide. Interaction of the OTS-8 peptide with the 237 antibody is characterized in tabular form in FIG. 14, which shows the contacts and non-covalent bonds by antibody region. The data in FIG. 14 show that the OTS-8 peptide contacts are found exclusively in the six CDR regions of the 237 antibody, providing a focus for the rational design of 237 scFv variants. The amino acid sequence of the light chain variable region and heavy chain variable region of the 237 antibody are presented in FIGS. 15 and 16, which identify the CDR regions by sequence. The sequence information and data from the three-dimensional interaction of the OTS-8 peptide with the 237 antibody guided the use of PCR to generate 237 scFv mutant libraries that were screened using yeast display and MACS/FACS sorting, as described below.

PCR Mutagenesis and Yeast Surface Display

Yeast surface display was used to screen 237 scFv mutants binding the Tn epitope-containing peptide OTS-8. The 237 scFv was cloned in-frame with Aga-2 (a yeast mating agglutinin protein), with an N-terminal hemaglutinin (HA) and a C-terminal myc (c-myc) tag. Aga2, through its known association with yeast protein Aga1 anchored to the yeast cell wall, allowed expression of 237 scFv as a fusion protein on the yeast cell surface. In schematic terms, the construct used for yeast surface display was H2N-Aga2-Hemagglutinin (HA)-scFv (or scTCR)-c-myc-$CO_2H$, also shown in FIG. 13(A).

Figure 13:
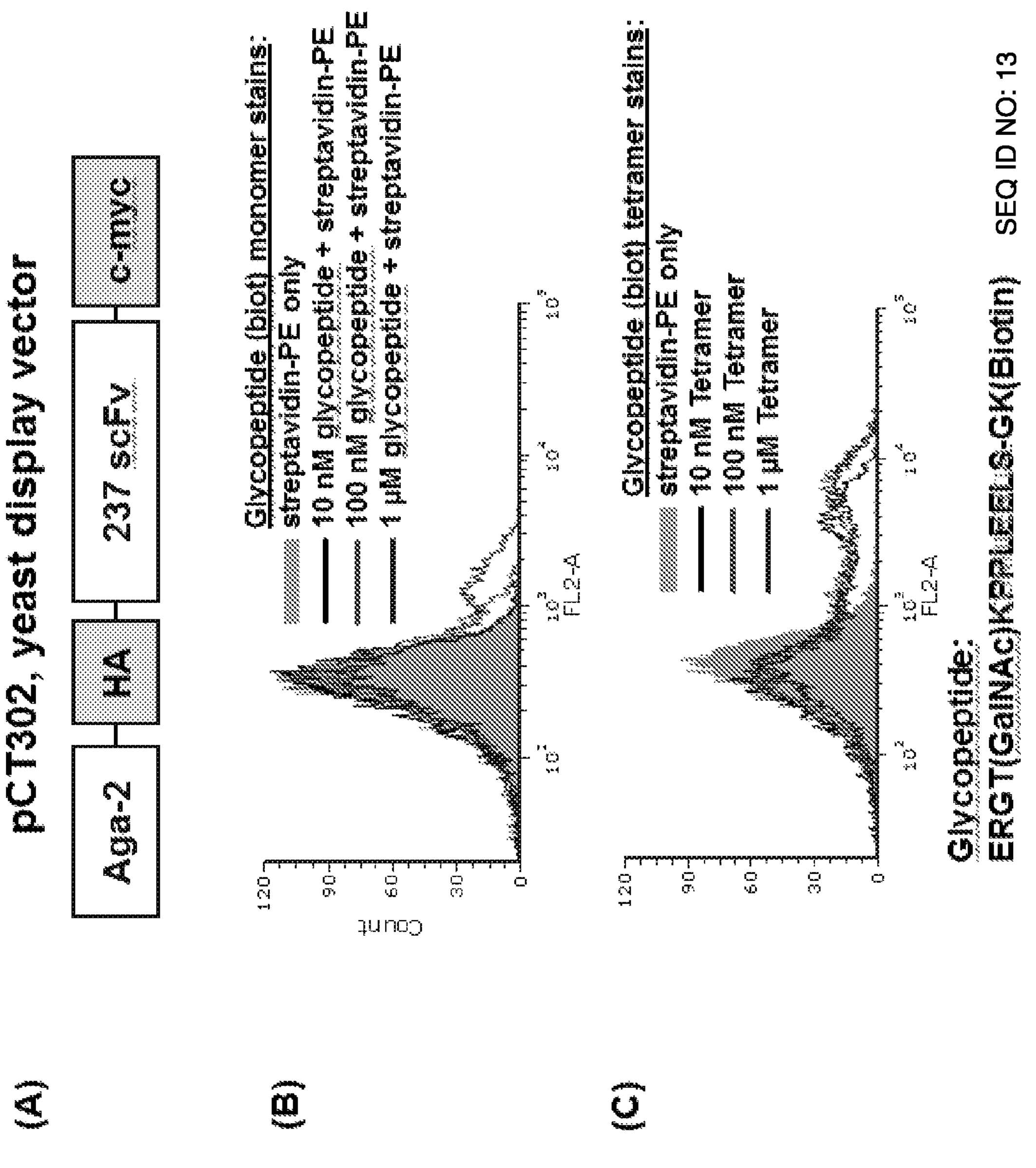
FIG. 13. Yeast surface display of 237 scFv. Schematic of 237 scFv cloned in yeast display vector, pCT302 is shown in (A). Yeast-displayed 237 scFv was stained with varying concentrations of glycosylated OTS-8 peptide (biotinylated), followed by streptavidin-PE in (B), or with tetramers of glycosylated OTS-8 peptide (C). The staining profile of yeast cells stained with streptavidin-PE only, is represented by gray peak. As indicated, surface-displayed 237 scFv weakly bound to 100 nM glycosylated OTS-8 peptide, but significantly well to OTS-8 peptide tetramers due to avidity.

Implementing screens based on yeast surface display initially involved cloning the bioreceptor gene (scFv or scTCR) into pCT302 as a suitable vector (FIG. 13). Successful cloning into the yeast display vector and expression of the encoded scFv was revealed by staining with biotinylated OTS-8 peptide and binding the biotinylated peptide with streptavidin PE (phycoerythrin), or by staining with OTS8 peptide tetramers.

PCR was used to introduce mutations into this construct, e.g., by error-prone amplification or by directed degeneracies. A library of mutated constructs was transformed into yeast by homologous recombination. The library was expanded and expression was induced. The expanded and induced library was stained using conditions designed to reveal a desired property such as protein folding, stability or affinity for a ligand. The library was sorted by degree of staining, which included, e.g., sorting for the best yeast binders to a given ligand. Expansion, expression induction, staining and sorting were then repeated 2-5 times to improve the selection. Next, the sorted clones were isolated and characterized. These clones were then used as a starting point for additional rounds of mutation and selection, ultimately resulting in the identification of a mutant bioreceptor tailored to optimize the selection criterion or criteria applied.

Diversity of CDR Libraries in 237 scFv

Nine CDR libraries were constructed from the CDRs of 237 scFv, with either 3 or 4 residues mutated at a time. Each library was transformed into electrocompetent yeast, and approximate library size was calculated based on observed transformation efficiency. Observed sizes were higher than theoretical sizes by at least an order of magnitude. Table 1 provides the observed and theoretical diversity of complementarity determining region libraries constructed in 237 scFv. The Table identifies the CDR mutated, the residues where libraries were made, the library size obtained and the theoretical library size expected.

TABLE 1

| Library (Loop-Targeted residues) | Library size obtained (Based on colony count) | Theoretical size |
|---|---|---|
| CDRL1-HSNG | $4.2 \times 10^7$ | $(32)^4 = 1.05 \times 10^6$ |
| CDRL1-GNTY | $1.7 \times 10^8$ | $(32)^4 = 1.05 \times 10^6$ |
| CDRL2-KVS | $7.1 \times 10^7$ | $(32)^3 = 3.3 \times 10^4$ |
| CDRL3-STHW | $2.6 \times 10^7$ | $(32)^4 = 1.05 \times 10^6$ |
| CDRH1-DAW | $1 \times 10^8$ | $(32)^3 = 3.3 \times 10^4$ |
| CDRH2-EIRN | $2 \times 10^7$ | $(32)^4 = 1.05 \times 10^6$ |
| CDRH2-NKAN | $1.3 \times 10^7$ | $(32)^4 = 1.05 \times 10^6$ |
| CDRH2-NNHE | $1 \times 10^8$ | $(32)^4 = 1.05 \times 10^6$ |
| CDRH3-KVR | $7.1 \times 10^7$ | $(32)^3 = 3.3 \times 10^4$ |

Sequences of clones from each CDR library showed mutational diversity in the expected region. Plasmid DNA isolated from single colonies of each library was sequenced to confirm mutational diversity in the targeted regions. All libraries showed mutational diversity in expected regions, as shown in Table 2.

TABLE 2

| Library | Colonies sequenced | Mutations at library location in colonies | Mutations outside library location in colonies (n of mutations) |
|---|---|---|---|
| HSNG | 10 | 10/10 | 3/10 (n = 1) |
| GNTY | 10 | 10/10 | 1/10 (n = 1) |
| KVS | 10 | 10/10 | 2/10 (n = 1) |
| STHV | 10 | 10/10 | 1/10 (n = 1); 1/10 (n = 2) |
| DAW | 8 | 8/8 | 2/8 (n = 1) 1/8 (n = 2) |
| EIRN | 10 | 10/10 | — |
| NKAN | 4 | 4/4 | 2/4 (n = 1) |
| NNHE | 9 | 9/9 | 2/9 (n = 1); 1/9 (n = 2) |
| KVR | 10 | 10/10 | — |

Figure 19:
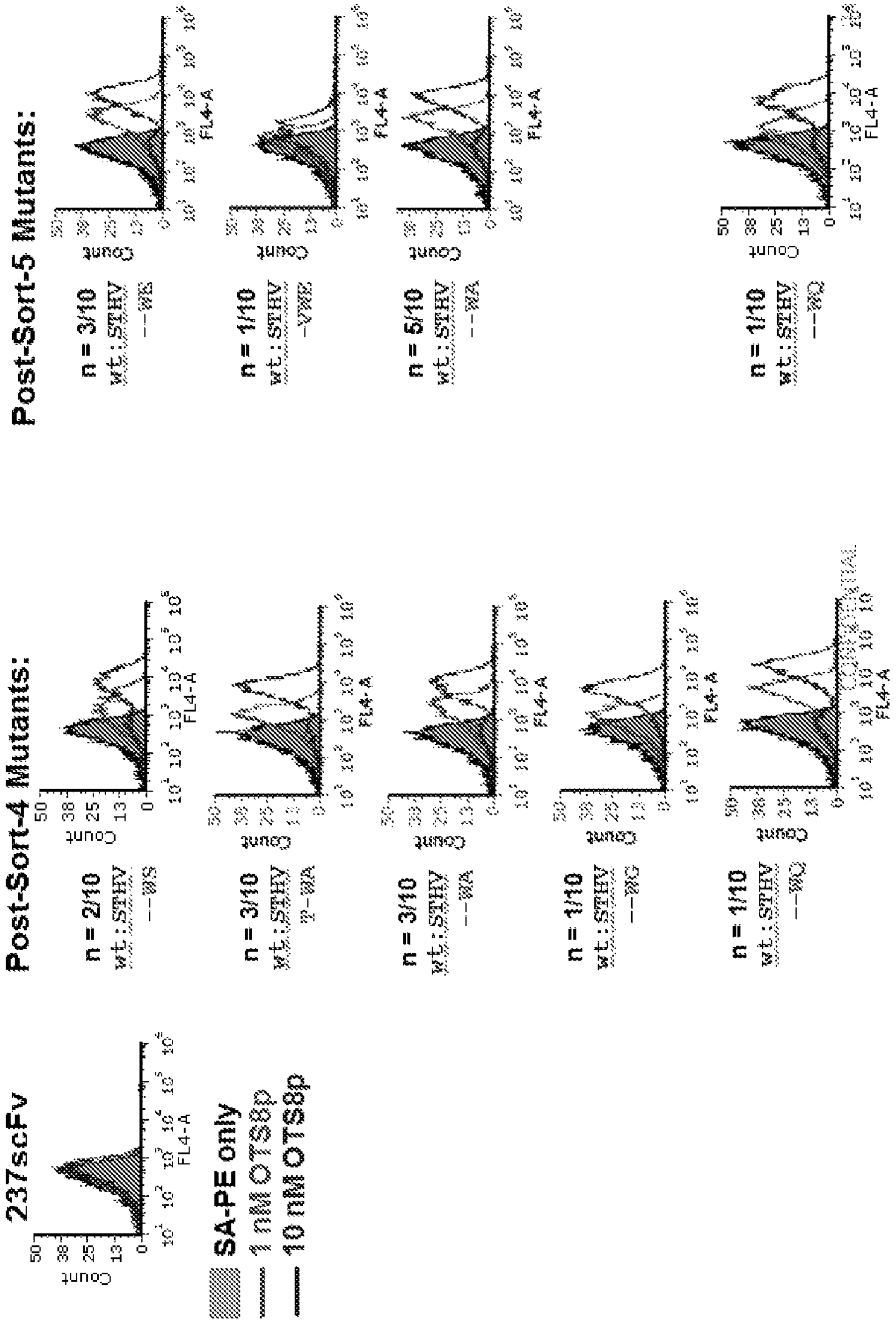
FIG. 19. Mutants isolated from Tn-OTS8p-sorted 237 CDR libraries contain mutations in CDRL3. 10 clones were isolated from Tn-OTS8 peptide-sorted post-sort-4 and post-sort-5 populations. Each clone was stained with 1 or 10 nM Tn-OTS8 peptide and analyzed by flow cytometry. As indicated, each clone exhibited superior staining with Tn-OTS8 peptide compared to the parent 237 scFv. In addition, plasmid DNA was isolated from each clone to determine the kind of mutation(s), and frequency of mutation(s) (n). The sequence of wild-type (wt) and mutated residues is shown in black and maroon, respectively.
Figure 20:
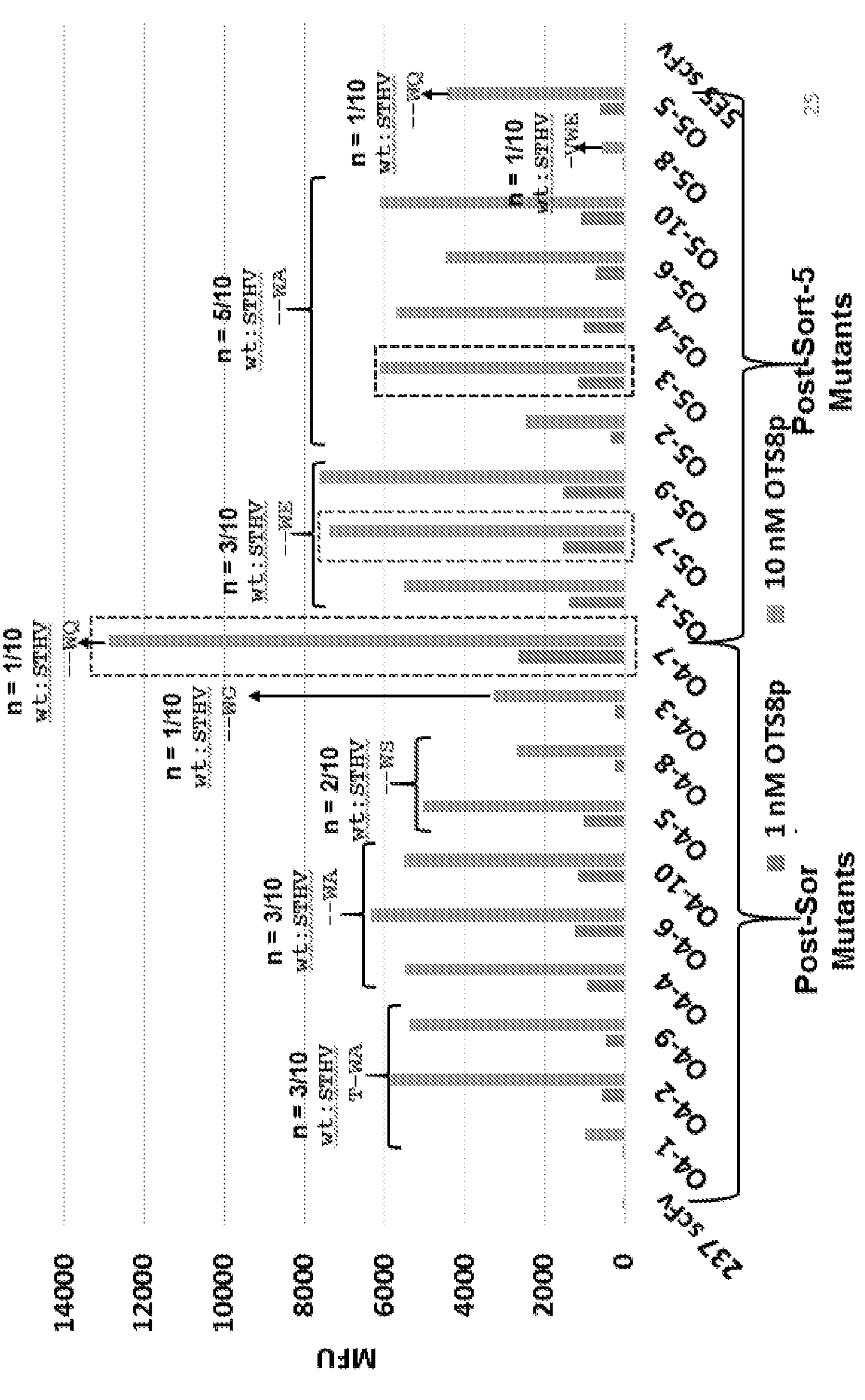
FIG. 20. Mutants isolated from Tn-OTS8p-sorted 237 CDR libraries contain mutations in CDRL3. 10 clones were isolated from Tn-OTS8 peptide-sorted post-sort-4 and post-sort-5 populations. Each clone was stained with 1 or 10 nM Tn-OTS8 peptide and analyzed by flow cytometry. The mean fluorescence units (MFUs) of each clone is plotted on Y-axis. As indicated, each clone exhibited superior staining with OTS8 peptide compared to the parent 237 scFv. In addition, plasmid DNA was isolated from each clone to determine the kind of mutation(s), and frequency of mutation(s) (n). The sequence of wild-type (wt) and mutated residues is shown in black and maroon, respectively.
Figure 23:
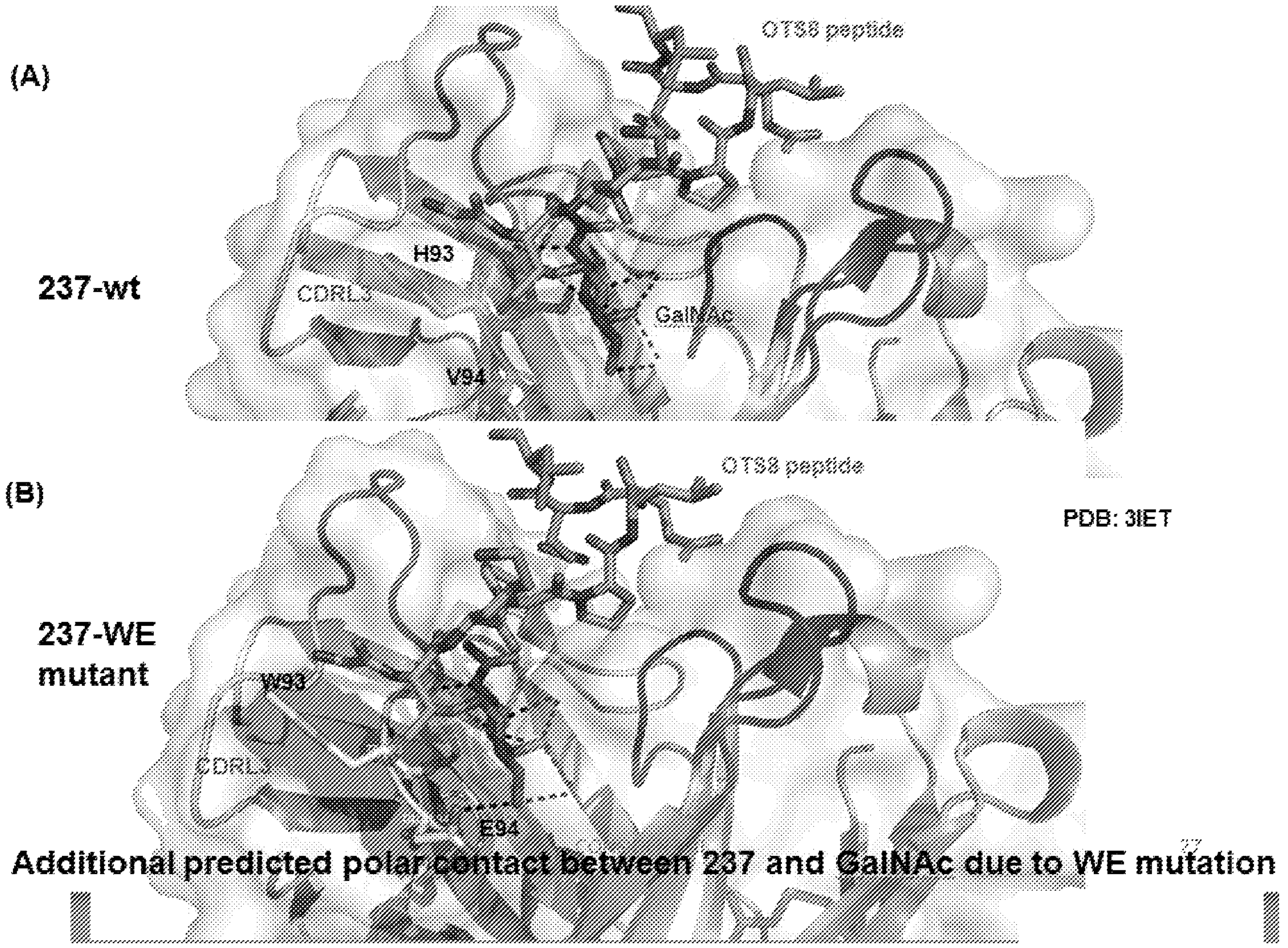
FIG. 23. Predicted location of the Trp-Glu (WE) mutation: Modeling based on the 237:OTS8p crystal structure. In order to gain insight into the possible mechanism by which the WE mutation imparted a 30-fold increase in affinity compared to the parent 237 scFv, the WE mutation was inserted into the crystal structure of 237 IgG with OTS-8 glycopeptide (PDB: 3IET) (Brooks et al., PNAS, 2010) by Pymol. As shown, the software predicted an additional polar contact between 237 and GalNAc due to WE mutation (B), compared to the wild-type (A).
Figure 36:
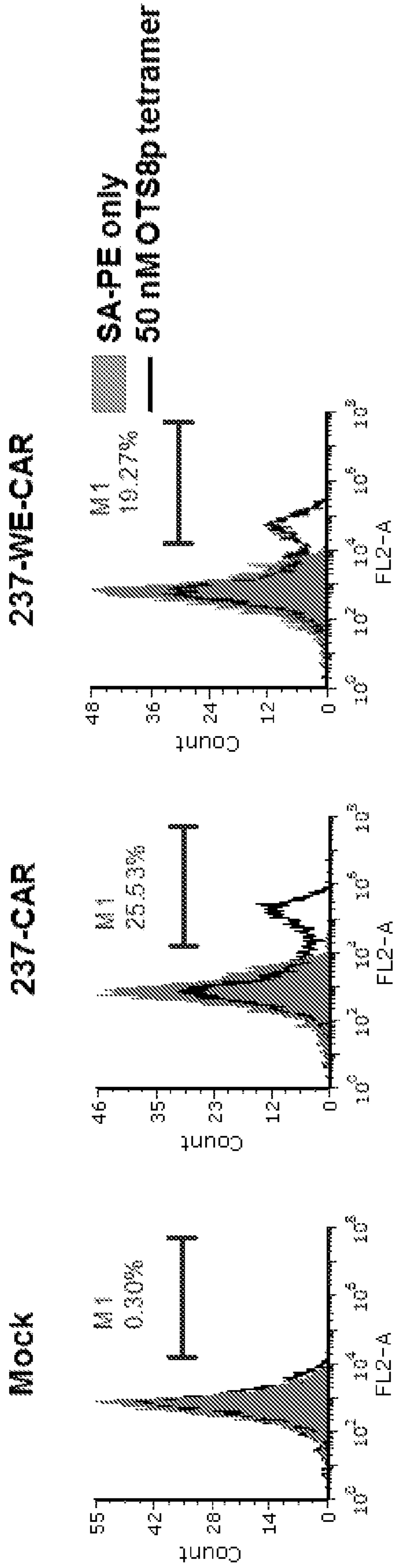
FIG. 36. Expression of the WE mutation in the 237 CAR format. In order to assess the impact of WE mutation in 237-CAR format, the mutation was inserted in 237scFv-CD28-CD3zeta CAR. Both wild-type and WE mutant CAR were introduced into total T cells from C57/BL6 mice, with an approximate transduction efficiency of 20%. Left panel—mock transduced T cells serving as a control; middle panel—T cells transduced with the 237 CAR; right panel—T cells transduced with the WE variant of the 237 CAR, designated 237-WE-CAR, were stained with 50 nM Tn-OTS8p tetramer (to assess transduction efficiency or CAR expression), or with streptavidin-PE only (gray)

Exemplary data showing the binding of 237 scFv variants containing mutations in CDRL3 (see FIG. 15, Table 1) that demonstrates the ability of the 237 scFv variants to bind the OTS-8 peptide after Sorts 4 and 5 are presented in FIGS. 19 and 20. The WE mutant at positions 98 and 99 of CDRL3 of the 237 scFv produced a scFv variant that showed promising specificity and avidity for the Tn epitope of the OTS-8 peptide. Without wishing to be bound by theory, FIG. 23 shows the additional ligand contact that is expected between the OTS-8 peptide and the 237 scFv WE variant. Beyond the WE variant, several variants that were constructed, including the WQ and WA variants (variant CDRL3 sequences), showed strong, specific binding to the Tn epitope-containing OTS-8 peptide, as shown in FIG. 21. To assess and compare the properties of 237 scFv wild-type and WE variant in CAR format, 237 CAR and 237-WE-CAR were generated and introduced into mouse T cells, and assessed for their binding to Tn-OTS8p tetramers (FIG. 36). The WE variant of the 237 CAR-T cell (and the 237 scFv) is, therefore, expressed and functional in binding the Tn epitope of the OTS-8 peptide.

The data disclosed herein supports the capacity of the 237 CAR-T cell, and 237 CAR-T cell variants, in particular variants in which 1, 2, 3, or 4 amino acids in one or more CDR regions have been substituted, to be effective in specifically binding to the Tn epitope found on various peptides and proteins, and thereby providing anti-cancer therapies for $Cosmc^-$ cancers.

Example 6

Isolation of 237scFv and 237 scFv Variants

Figure 17:
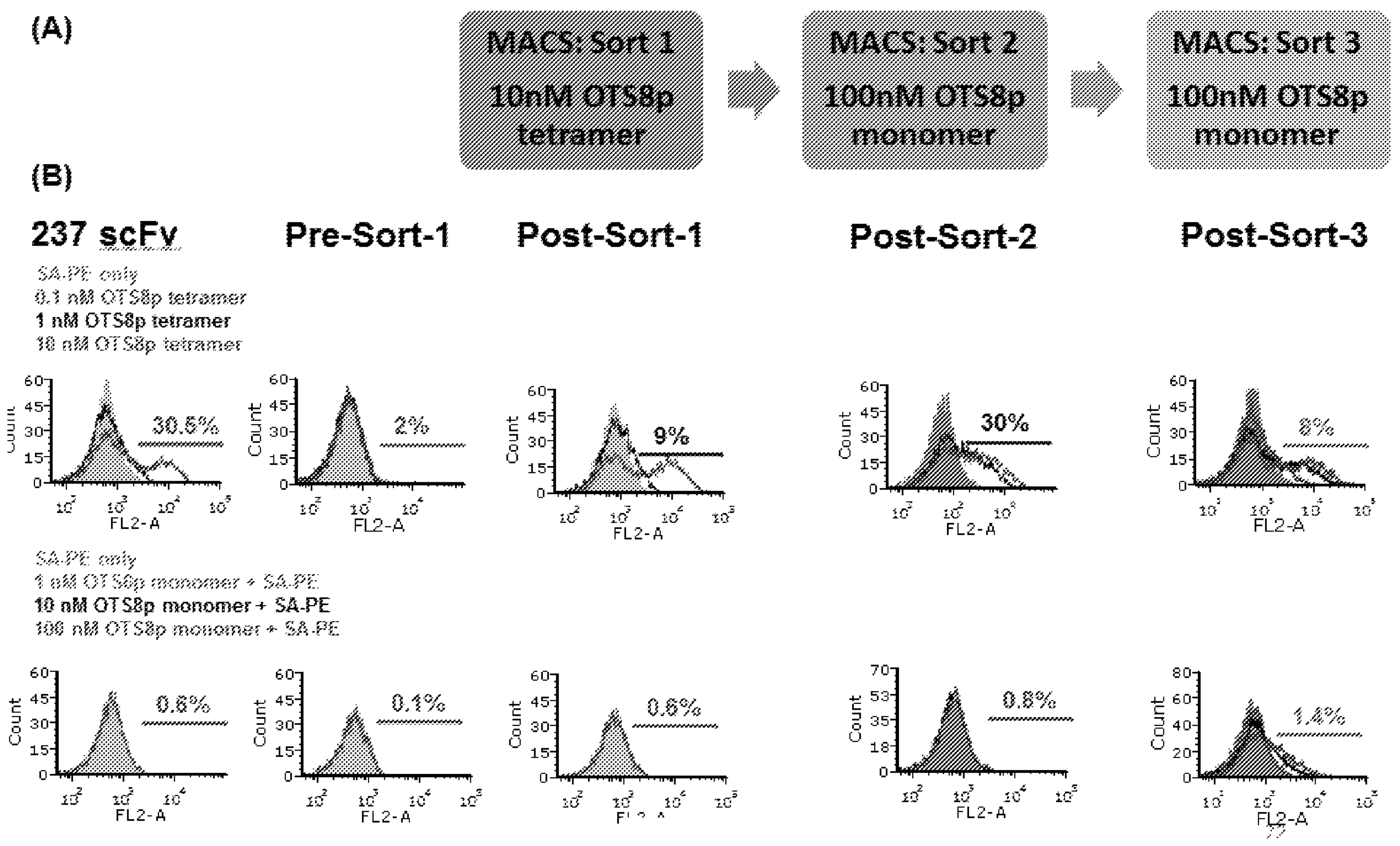
FIG. 17. Sorting 237 CDR libraries with cognate ligand, Tn-OTS8p, for higher affinity clones. (A) The progression of various sorts of 237 libraries, including the technique used (MACS/FACS), and the sorting reagent (Tn-OTS8 peptide as tetramer or monomer) is shown. (B) 237 scFv as well as the various stages of 237 libraries (Pre-sort and post-sort) were stained with various concentrations of Tn-OTS8 peptide as tetramer or monomer to determine the ligand concentration for subsequent sort, and to track enrichment. Marker populations indicate increase in percent positive population compared to negative control (in gray).
Figure 18:
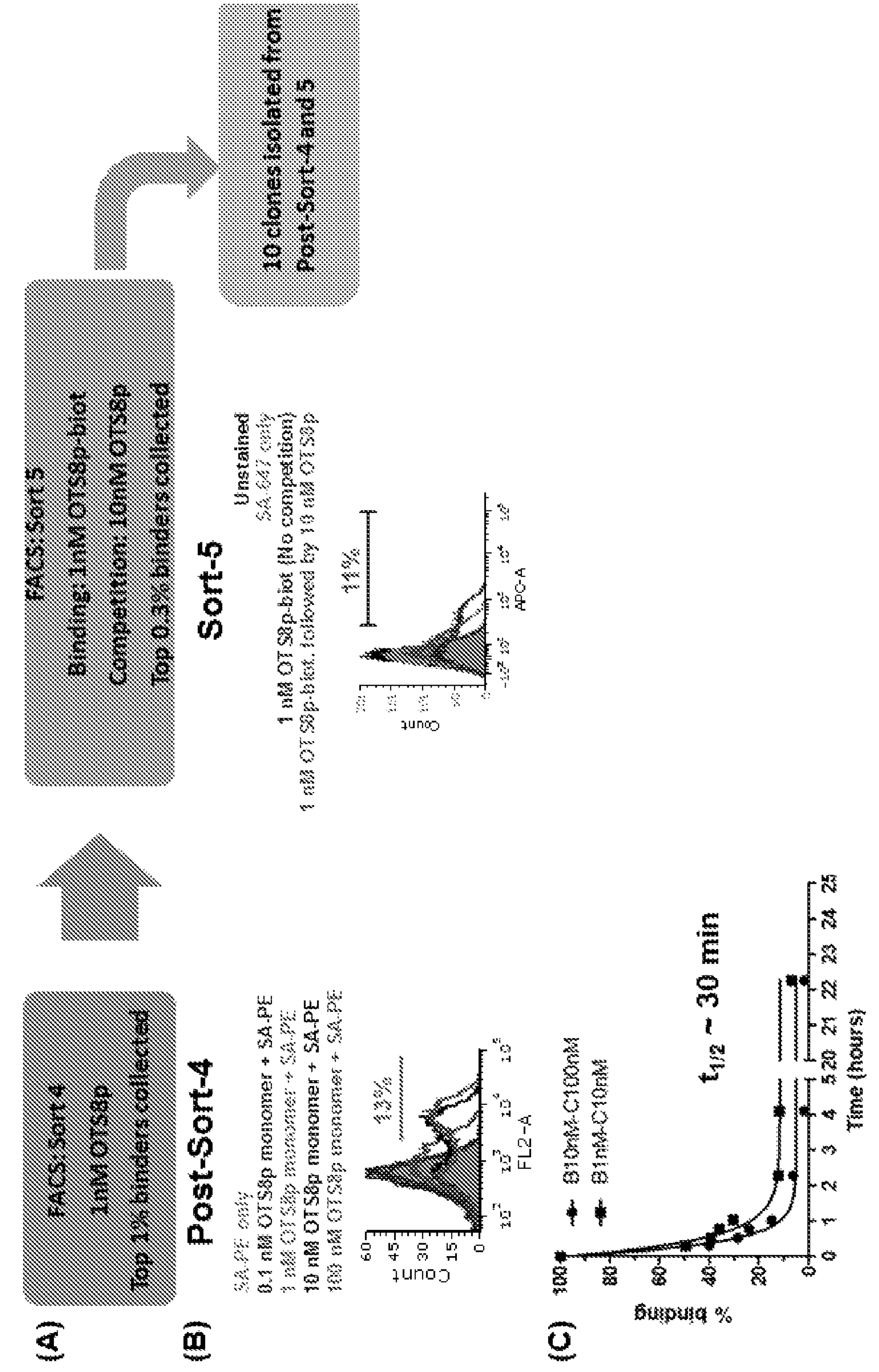
FIG. 18. Sorting 237 CDR libraries with cognate ligand, Tn-OTS8p, for higher affinity clones. (A) The progression of various sorts of 237 libraries, including the technique used (MACS/FACS), and the sorting reagent (Tn-OTS8 peptide as tetramer or monomer) is shown. (B) 237 scFv as well as the various stages of 237 libraries (Pre-sort and post-sort) were stained with various concentrations of Tn-OTS8 peptide as tetramer or monomer to determine the ligand concentration for subsequent sort, and to track enrichment. Marker populations indicate increase in percent positive population compared to negative control (in gray). (C) After sort-4, the library was stained with 10 or 1 nM Tn-OTS8p (biotinylated). After washing, the library was stained with 100 nM or 10 nM Tn-OTS8p (not biotinylated) respectively. The decrease in binding of libraries to biotinylated Tn-OTS-8p was measured over a period of 24 hours, to calculate approximate half-life ($t_{1/2}$) of sorted libraries. This information was used to conduct the sort-5 (off-rate limited) of 237 libraries, following which 10 clones were isolated from sorted libraries.

The 237 scFv and 237 scFv variants generated by mutagenesis as described herein were isolated using both Fluorescence Activated Cell Sorting (FACS) and Magnetically Activated Cell Sorting (MACS). In particular, the sorting scheme involved a combination of MACS and FACS. The combined approach was adopted to take advantage of both sorting techniques. MACS is a rapid sorting technique capable of sorting $10^9$ cells in 15 minutes, but small subpopulations of cells cannot be enriched using this technique. FACS typically sorts about $2\times10^7$ cells per hour, but subpopulations of cells of interest can be enriched. The combined sorting scheme was used to isolate 237 scFv variants having higher affinity than the wild-type 237 scFv (FIGS. 17 and 18). The identities and sequences of wild-type 237 scFv and various 237 scFv mutants recognizing Tn-linked antigens are provided in Table 3.

TABLE 3

| Tn-linked antigen | scFv | SEQUENCE IDENTIFIER | Sequence of scFv |
|---|---|---|---|
| Tn-OTS8 peptide | 237-wt | 19 | DIQLTQSPLSLPVSLGDQASISCRSSQSLVHSNGNTYLHWYLQ KPGQSPKLLIYKVSNRFSGVPDRFSGSGSGTDFTLKISSVEAE DLGVYFCSQSTHVPTFGGGTKLEIKGGGGSGGGGSGGGGSQVQ LQQSGGGLVQPGGSMKIFCAASGFTFSDAWMDWVRQSPEKGLE WVAEIRNKANNHETYYAESVKGRFTITRDDSKSRMSLQMNSLR AEDTGIYYCSGGKVRNAYWGQGTTVTVSS |
| Tn-OTS8 peptide | 237-WE | 20 | DIQLTQSPLSLPVSLGDQASISCRSSQSLVHSNGNTYLHWYLQ KPGQSPKLLIYKVSNRFSGVPDRFSGSGSGTDFTLKISSVEAE DLGVYFCSQST**WE**PTFGGGTKLEIKGGGGSGGGGSGGGGSQVQ LQQSGGGLVQPGGSMKIFCAASGFTFSDAWMDWVRQSPEKGLE WVAEIRNKANNHETYYAESVKGRFTITRDDSKSRMSLQMNSLR AEDTGIYYCSGGKVRNAYWGQGTTVTVSS |
| Tn-OTS8 peptide | 237-LGQ | 21 | DIQLTQSPLSLPVSLGDQASISCRSSQSLVHSNGNTYLHWYLQ KPGQSPKLLIYKVSNRFSGVPDRFSGSGSGTDFTLKISSVEAE DLGVYFCSQS**LGQ**PTFGGGTKLEIKGGGGSGGGGSGGGGSQVQ LQQSGGGLVQPGGSMKIFCAASGFTFSDAWMDWVRQSPEKGLE WVAEIRNKANNHETYYAESVKGRFTITRDDSKSRMSLQMNSLR AEDTGIYYCSGGKVRNAYWGQGTTVTVSS |
| Tn-OTS8 peptide | 237-TNGK | 22 | DIQLTQSPLSLPVSLGDQASISCRSSQSLVHSNGNTYLHWYLQ KPGQSPKLLIYKVSNRFSGVPDRFSGSGSGTDFTLKISSVEAE DLGVYFCSQ**TNGK**PTFGGGTKLEIKGGGGSGGGGSGGGGSQVQ LQQSGGGLVQPGGSMKIFCAASGFTFSDAWMDWVRQSPEKGLE WVAEIRNKANNHETYYAESVKGRFTITRDDSKSRMSLQMNSLR AEDTGIYYCSGGKVRNAYWGQGTTVTVSS |
| Tn-MUC1 peptide | 237-LGQ | 23 | DIQLTQSPLSLPVSLGDQASISCRSSQSLVHSNGNTYLHWYLQ KPGQSPKLLIYKVSNRFSGVPDRFSGSGSGTDFTLKISSVEAE DLGVYFCSQS**LGQ**PTFGGGTKLEIKGGGGSGGGGSGGGGSQVQ LQQSGGGLVQPGGSMKIFCAASGFTFSDAWMDWVRQSPEKGLE WVAEIRNKANNHETYYAESVKGRFTITRDDSKSRMSLQMNSLR AEDTGIYYCSGGKVRNAYWGQGTTVTVSS |
| Tn-MUC1 peptide | 237-TNGK | 24 | DIQLTQSPLSLPVSLGDQASISCRSSQSLVHSNGNTYLHWYLQ KPGQSPKLLIYKVSNRFSGVPDRFSGSGSGTDFTLKISSVEAE DLGVYFCSQ**TNGK**PTFGGGTKLEIKGGGGSGGGGSGGGGSQVQ LQQSGGGLVQPGGSMKIFCAASGFTFSDAWMDWVRQSPEKGLE WVAEIRNKANNHETYYAESVKGRFTITRDDSKSRMSLQMNSLR AEDTGIYYCSGGKVRNAYWGQGTTVTVSS |

FACS and MACS were used in combination to sort 237 libraries. Initial sorts were conducted by MACS that facilitated the screening of high mutational diversity (approximately, $7\times10^8$ transformants after pooling nine 237 libraries) in initial stages. In order to identify individual mutants from the libraries, later sorts, involving lower levels of mutational diversity, were conducted with FACS, which facilitated the collection of a specific percentage of cells of interest.

Sorts were also used to obtain variants of 237 scFv that would bind to other Tn-linked epitope(s), not just to the Tn epitope found on PDPN (i.e., the OTS-8 peptide). Using MUC-1, which bears an O-glycosylated residue that can yield the Tn epitope, binding studies were performed on the 237 scFv and on the 5E5 scFv (i.e., the scFv derived from the anti-MUC1 antibody recognizing the MUC1 Tn epitope). The results of serial sorting shown in FIGS. 33 and 34, and the sort data of FIG. 35, reveal that 237 scFv variants can be isolated that can also bind to Tn-MUC-1 peptide (in addition to Tn-OTS8 peptide), confirming the ability to adjust the specificity of the 237 scFv, and 237 CAR-T cell, to specifically bind to the Tn epitope regardless of protein bearing that epitope.

Example 7

Activation of T Cells

Following the purification of the 237 CAR-T cell and 237 variant CAR-T cells, these cells were investigated to determine if they would be activated by cancer cells due to the presence of a cell-surface, cancer-associated antigen to activate the T cells. Total T cells were initially isolated from C57BL/6 mice and transduced with either 237-CAR (237) or WE-CAR (WE) to yield 237 CAR-T cells and WE-237 CAR-T cells. These T cells were then separately co-cultured with 25,000 target cells of (A) murine Ag104A cancer cells, or (B) $58^{-/-}$ control murine cells, for 24 hours at 37° C., 5% $CO_2$ at various effector:target (E:T) ratios. The amount of IFN-γ released in the supernatants under each co-culture condition was measured by ELISA. The results shown in FIG. 37 establish that the Ag104A cancer cells induced steadily increasing levels of IFN-γ while mock-infected or Ag104A cells alone did not produce detectable levels of IFN-γ, as shown in panel (A) of FIG. 37. Consistently, exposure of 237 CAR-T cells or WE-CAR-T cells to $58^{-/-}$ murine control cells led to undetectable levels of IFN-γ production for mock-infected cells, for 58−/− target cells incubated alone, and for both 237 CAR-T cells and WE-CAR-T cells exposed to $58^{-/-}$ cells. Thus, both wild-type 237 CAR-T cells and 237 variant CAR-T cells, e.g., WE-CAR-T cells, are specifically activated by cancer cells bearing the Tn epitope.

Example 8

Engineering 237 scFv for More Effective Targeting of Tn-Linked Antigens

To optimize the targeting of Tn-linked antigens on cancer cells, an antibody form with high affinity against the targeting agent is desired, whether the antibody form is a CAR, a BiTE, or another antibody form. For T cell receptors (TCRs), the optimal affinity window is narrow due to their higher sensitivities because of the involvement of CD3 subunits and other cellular signaling machinery (98, 99). CARs and soluble reagents like antibodies or BiTEs, however, often require higher affinity (e.g., low nanomolar to picomolar $K_D$ values) for higher efficacy. For example, Lynn et al. demonstrated efficacy of a high affinity, folate receptor beta-targeted CAR ($K_D$=2.5 nM) in a mouse model of human acute myeloid leukemia (AML), and against primary human AML (109). In fact, the scFv used in the FDA-approved CD19 CAR for the treatment of acute lymphoblastic leukemia (ALL), and relapsed or refractory large B-cell lymphoma, exhibits a $K_D$ of 5 nM for CD19 (113, 114, 129, 130). In addition, density of the cancer antigen also has an impact on the affinity requirement. A low density target may require a high affinity CAR for efficient targeting; however, its affinity may need fine tuning to discriminate tumor from normal tissue expressing low levels of antigen (87, 107, 126). In the case of BiTEs, however, lower affinities are correlated with higher therapeutic potential. For example, the FDA-approved Blinatumomab for ALL has an affinity of 1 nM for CD19, and was shown to induce lymphoma-directed T cell cytotoxicity at very low concentrations (10-100 pg/ml) (100, 108). This BiTE has now been shown to induce durable responses in patients at low doses in several studies (82, 137). Similarly, ImmTACs, which replace high affinity scFv in BiTEs with high affinity TCRs (nanomolar to low picomolar $K_D$) but target intracellular antigens, have been shown to allow T-cell mediated killing of tumor lines, and control tumor growth in mouse models (74, 115).

Figure 15:
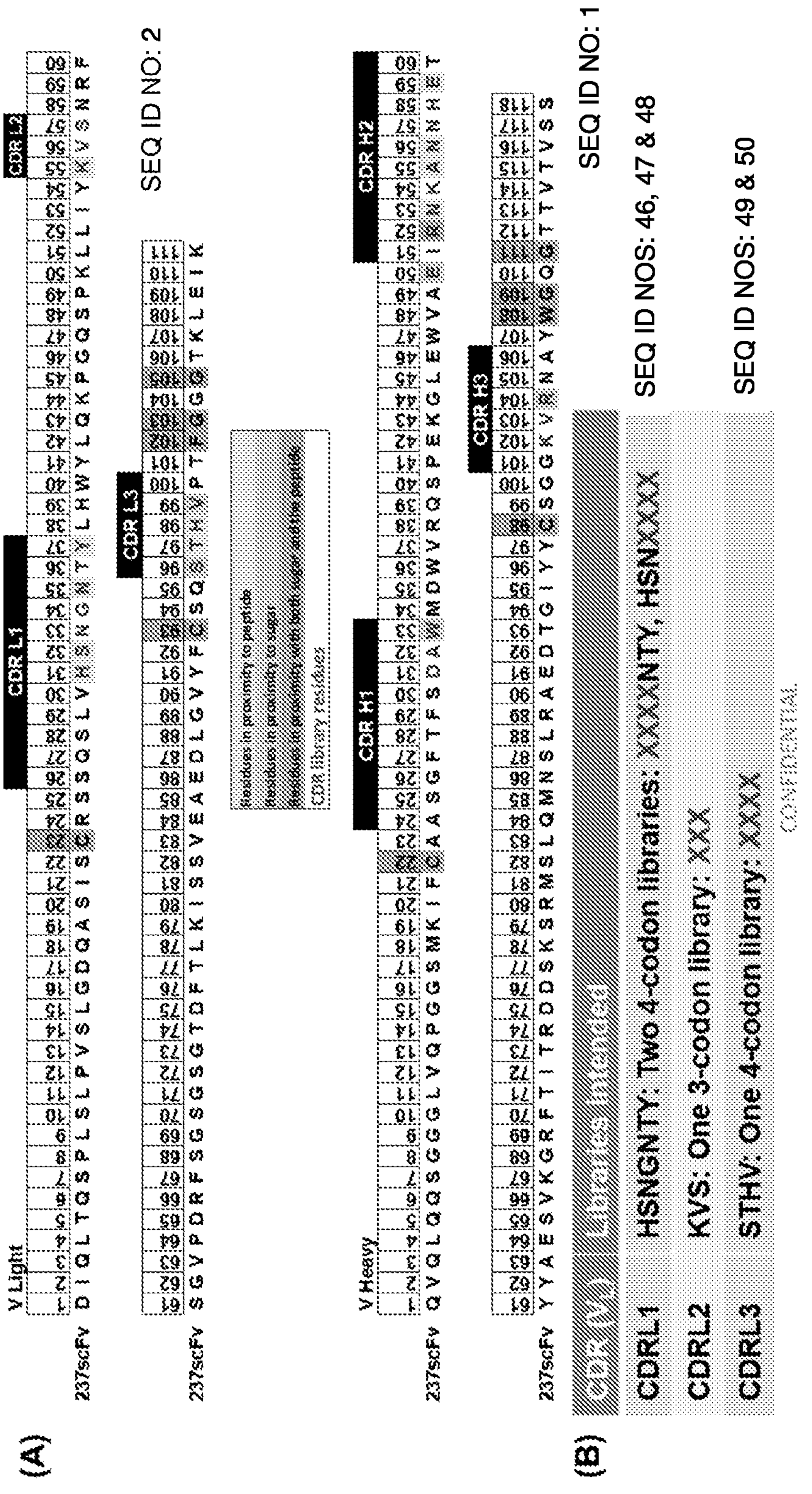
FIG. 15. CDR light chain mutational libraries constructed in 237 scFv using PCR. (A) Sequence of 237 scFv is shown. The residues in proximity to OTS8 peptide, sugar (GalNAc) or both are highlighted in yellow, tan and green respectively. (B) Sequences of CDRs in light chain and number of libraries prepared are tabulated. Targeted residues for making 3- or 4-codon libraries are indicated as "X" (red).
Figure 16:
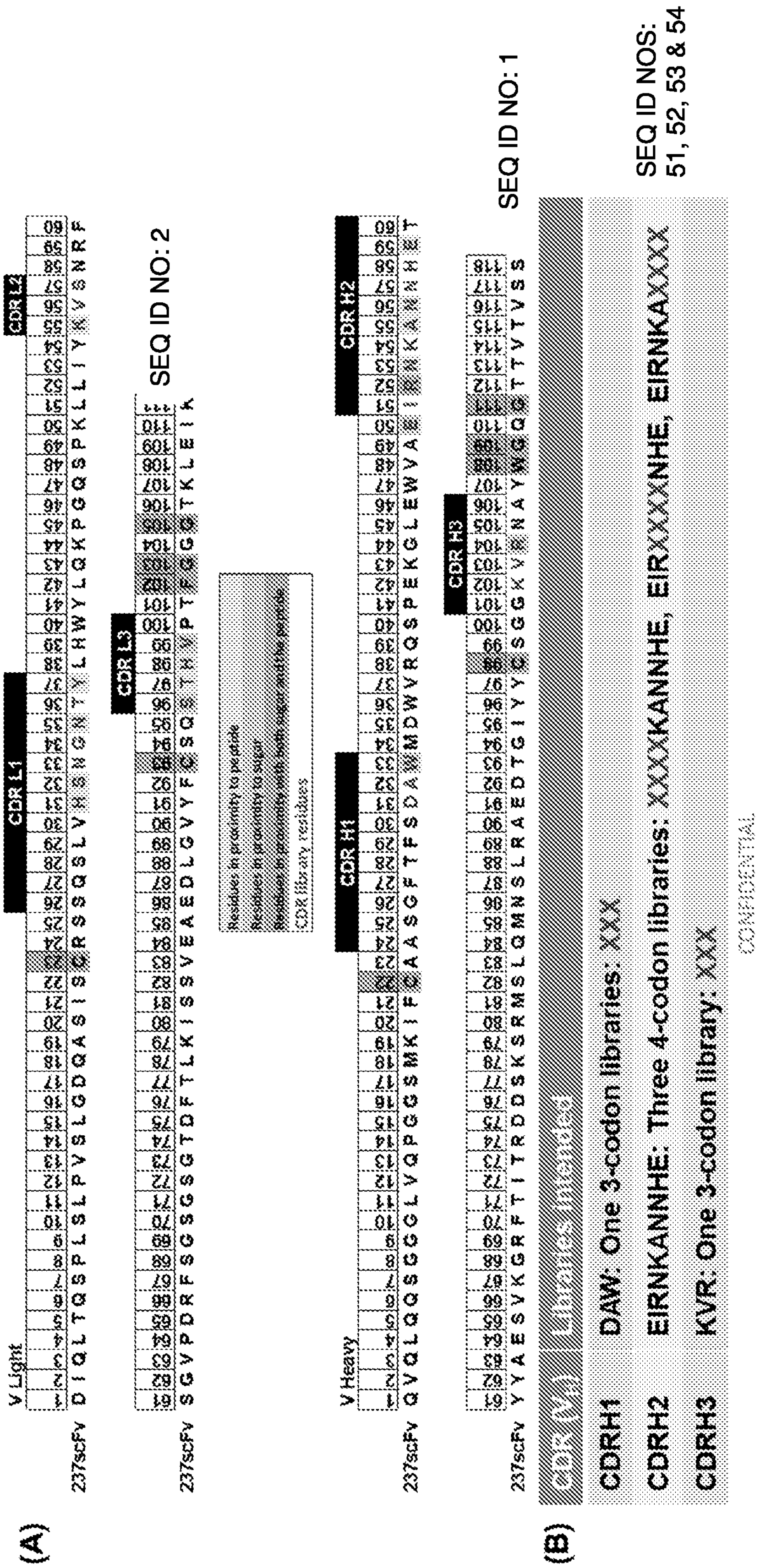
FIG. 16. CDR heavy chain mutational libraries constructed in 237 scFv using PCR. (A) Sequence of 237 scFv is shown. The residues in proximity to OTS8 peptide, sugar (GalNAc) or both are highlighted in yellow, tan and green respectively. (B) Sequences of CDRs in heavy chain and number of libraries prepared are tabulated. Targeted residues for making 3- or 4-codon libraries are indicated as "X" (red).
Figure 37:
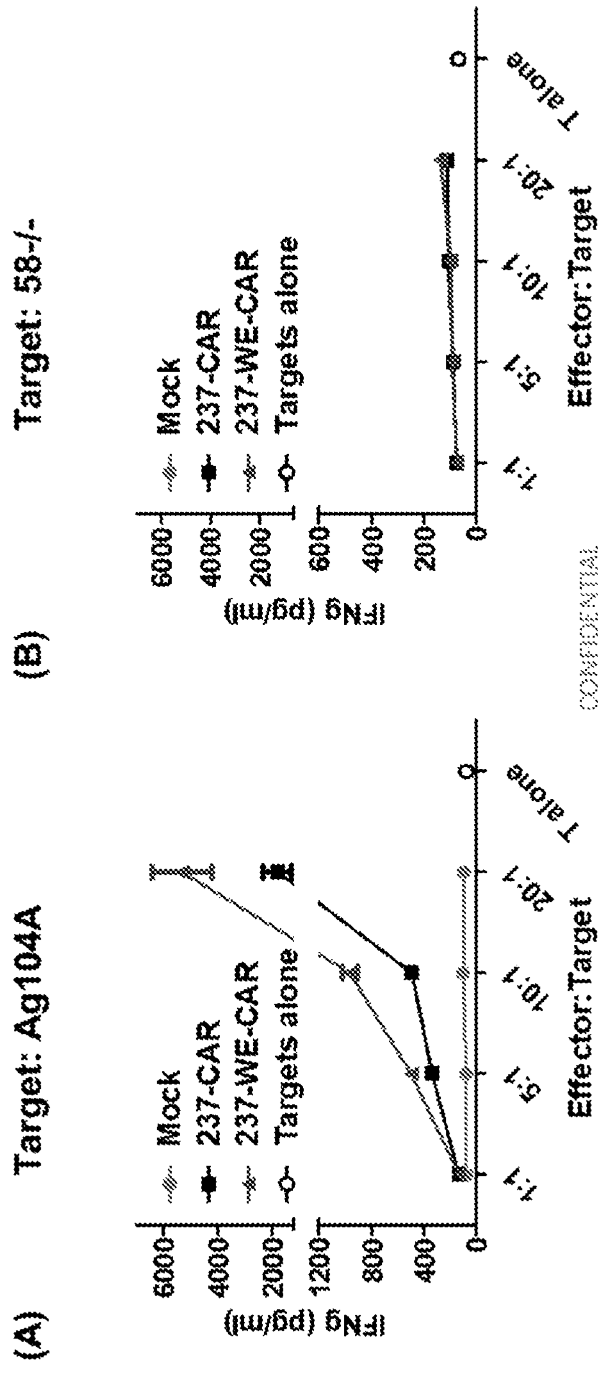
FIG. 37. Activation of T cells transduced with 237-CAR or 237-WE-CAR upon co-culture with Ag104A murine cancer cells, but not after co-culture with control murine cell line $58^{-/-}$. Total T cells from C57BL/6 mice were transduced with the 237 CAR (237) or the 237-WE-CAR (WE) variant. Transduced cells were separately co-cultured with 25,000 target cells (Ag104A (A), or $58^{-/-}$ (B)), for 24 hours at 37° C., 5% $CO_2$ at various effector:target (E:T) ratios. The quantity of IFN-γ released in the supernatants under each co-culture condition was measured by standard ELISA assay.

In order to develop Tn-specific CARs and BiTEs that are able to efficiently target a cancer antigen of interest, a panel of high-affinity 237 scFv mutants was engineered using yeast display. For this purpose, a structure-guided approach was used to design libraries of 237 scFv mutants in residues that are in proximity to, or mediate binding to, the antigen (e.g., the sugar-binding and peptide-binding residues of the 237 antibody that contact Tn-OTS8) (FIG. 12, 14) (3). Yeast surface display was used to construct nine libraries in complementarity determining regions (CDRs) of heavy and light chains of 237 scFv (FIGS. 13, 15, 16). These diverse libraries (Tables 2, 3) were expressed on the surface of yeast cells and subjected to a combination of magnetic cell sorting (MACS) and fluorescence-activated cell sorting (FACS) with tetrameric or monomeric Tn-OTS8 peptide (ERGT(GalNAc)KPPLEELSGK-biotin; SEQ ID NO:13). Sorts 1 to 3 were conducted by MACS that allowed the screening of libraries with high mutational diversity (approximately $7 \times 10^8$ transformants after pooling nine 237 libraries) in initial stages (FIG. 17). In order to identify individual high affinity mutants from the libraries, sorts 4 and 5 were conducted with FACS, which allowed for the collection of a specific percentage of cells of interest binding to low concentrations of Tn-OTS8 peptide (FIG. 18). After the fourth and fifth sorts, ten 237 scFv mutants were isolated and analyzed for binding to low concentrations (1 or 10 nM) Tn-OTS8 peptide, and compared with the parent 237 scFv. The data show that all isolated mutants exhibited higher binding to Tn-OTS8 peptide compared to the parent 237 scFv (FIGS. 19, 20). Sequencing indicated that these mutants contained mutations in the CDR3 domain of the light chain of 237 scFv, which was shown to interact with GalNAc (Tn) on OTS8 peptide in the crystal structure (FIGS. 19, 20) (3). Three 237 scFv mutants (WQ, WA, WE) were further analyzed by flow cytometry-based Tn-OTS8 peptide-binding titration, and were shown to exhibit affinities that were 30-fold higher than the parental 237 scFv (FIG. 21) (3). Modeling the highest affinity mutation (the WE mutation) in the co-crystal structure of the 237 antibody and the Tn-OTS8 peptide (3) led to the expectation that one mechanism responsible for the increase in affinity was the additional polar contact of the GalNAc moiety with the 237 scFv-WE mutant (FIG. 23). The highest affinity mutation was then introduced into a 237-CAR (237scFv-CD28-CD3zeta) to generate 237-WE-CAR, and the cell surface expression of both of these CARs was confirmed after transduction into mouse T cells (FIG. 36). These CARs were then compared in an activation assay with the Ag104A and $58^{-/-}$ cell lines as targets, and cytokine (IFN-γ) release was measured (FIG. 37). As shown, the high affinity CAR (237-WE-CAR) transduced T cells were activated more than the wild-type 237-CAR transduced T cells when co-cultured with Ag104A cancer cells, indicating that the high affinity mutation resulted in better recognition of the target antigen (Tn-OTS8) on Ag104A cells (FIG. 37A). A negative control cell line that did not express Tn-OTS8 (i.e., $58^{-/-}$, a murine T cell line) did not induce IFN-γ release from Mock-, 237-CAR-, or 237-WE-CAR-transduced T cells (FIG. 37B).

Figure 10:
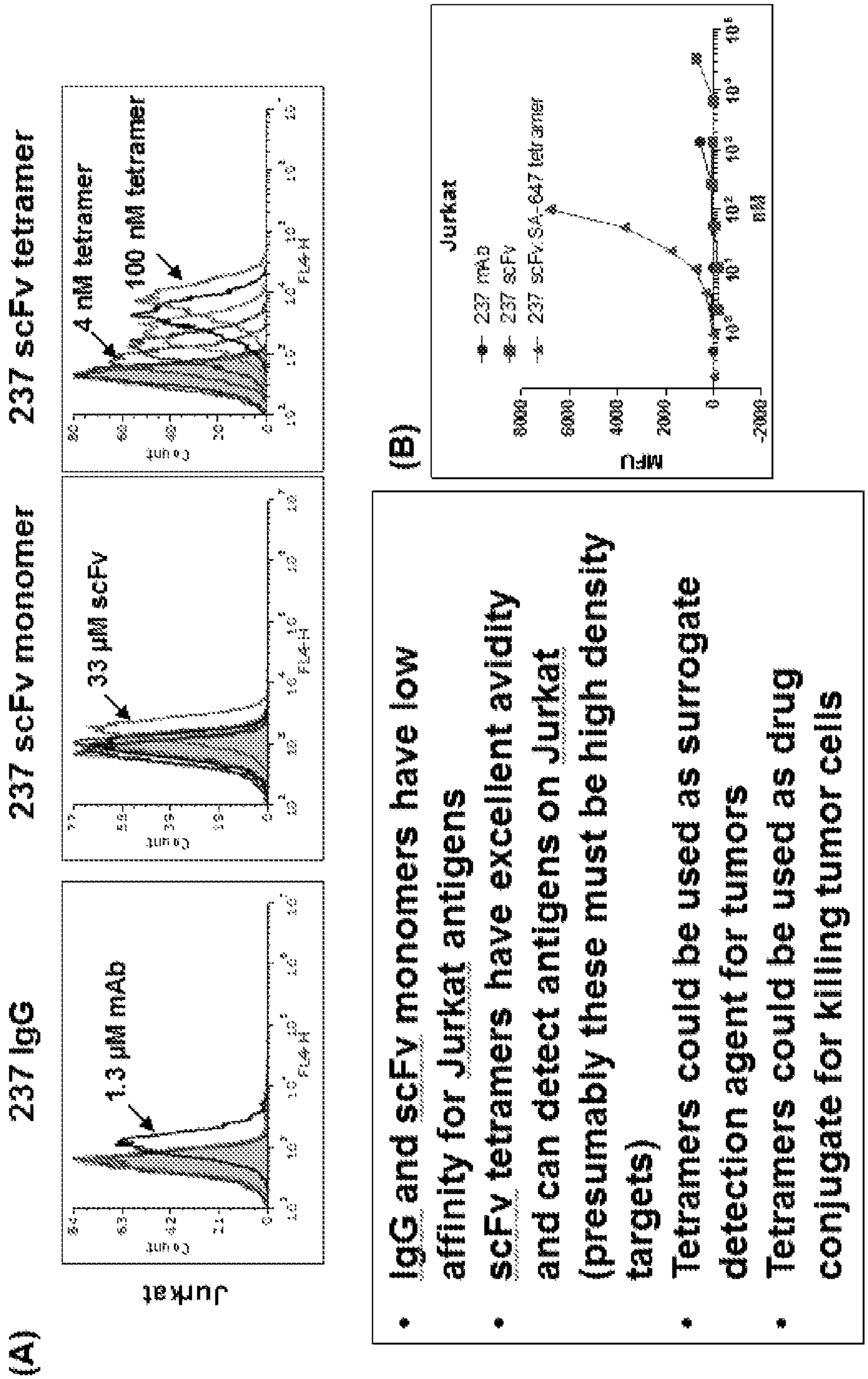
FIG. 10. Binding of various compositions of 237 antibody to Jurkat cells. (A) Jurkat cells were stained with various concentrations of 237 IgG or 237 scFv monomer (biotinylated) or 237 scFv tetramers (prepared with biotinylated 237 scFv and streptavidin-647), and analyzed by flow cytometry. The staining profile of cells stained with secondary reagent only is represented by the gray peak. (B) Mean fluorescence units (MFU) from (A) were plotted against concentration of 237 IgG or scFv or scFv tetramer to obtain binding curves.

An experiment was also conducted to compare the binding of the monomeric and tetrameric forms of the 237 scFv to Jurkat cancer cells. The 237 scFv monomer was labeled with biotin, and the tetramer was produced by adding streptavidin-647. As a control, the 237 antibody was also exposed to Jurkat cancer cells. Various concentrations of these binding agents were exposed to Jurkat cancer cells and binding was analyzed by flow cytometry. The results of the binding study are shown in FIG. 10(A). Mean fluorescence units from these binding studies were graphed as a function of the concentration of the binding agent to yield the binding curves shown in FIG. 10(B). The results establish that both the 237 antibody and the 237 scFv monomer bound to Jurkat cancer cells weakly, but the binding of the 237 scFv tetramer to Jurkat cancer cells exhibited significantly greater sensitivity. The 237 scFv tetramer has excellent avidity for the antigen on Jurkat cells and is a useful reagent for detecting such cancer cells and the antigens on the cell surface of such cancer cells. These results establish the 237 scFv tetramer as a versatile anti-cancer targeting agent in a variety of applications, including cancer treatment, cancer diagnosis, and the identification of cancer patients amenable to $Cosmc^{-}$ cancer-based treatments.

Example 9

237 scFv Binding to OTS8 Peptide Epitope Variants

The OTS-8 epitope of PDPN that binds the 237 scFv was chosen for further studying its binding interactions with 237 scFv. An initial binding titration was performed by coating microtiter wells with unglycosylated OTS-8 peptide (OTS8p) at 2.5 or 5 μg/ml, or with the OTS-8 peptide exhibiting the Tn epitope, again at 2.5 or 5 μg/ml. Biotinylated 237 scFv was added to the wells at various concentrations, and bound 237 scFv was detected using streptavidin-HRP by ELISA. The results, shown in FIG. 11, establish that the 237 scFv does not bind unglycosylated OTS-8 peptide, but does bind to either concentration of the Tn-OTS8 peptide, with detectable binding beginning in the low nanomolar range of about 2-3 nM. The binding curve generated in this study led to the calculation of an apparent $K_D$=5±1 nM.

The binding of 237 scFv to the OTS-8 epitope of PDPN led to an exploration of the essential content of that epitope required for binding to the 237 scFv. As shown in FIG. 28, a series of Ala mutants of the OTS-8 epitope were generated, as described in the following Example, and these OTS-8 variants were subjected to binding studies using the 237 antibody and the 237 CAR-T cell. The OTS-8 variants were coated in microtiter wells at varying concentrations ranging from 0.1 to 1000 nM and the $OD_{450}$ was measured to detect 237 antibody binding while IFNγ production (pg/ml) was used to measure 237 CAR-T cell activation. The results shown in FIG. 28 reveal that significant activation occurred with the 237 CAR-T cell using OTS-8 peptides having sequences that varied significantly from the wild-type OTS-8 sequence and, as the variation from the wild-type OTS-8 sequence varied more, 237 CAR-T cells retained the capacity for activation where detectable binding of the 237 antibody had fallen off. Thus, the 237 CAR-T cell recognizes cancer epitopes with fewer invariant residues than recognized by the 237 parent antibody, indicating that the 237 CAR-T cell exhibits an unexpectedly wider range in binding cancer epitopes.

The greater range of cancer epitopes recognized by the 237 CAR-T cell compared to the parent 237 antibody was confirmed by examining binding to OTS-8 variants containing multiple Ala substitutions. Again, the binding assay assessed 237 antibody binding to immobilized OTS-8 variant peptide using a colorimetric assay detected at $OD_{450}$ and assessed 237 CAR-T cell activation by measuring IFNγ production. The results shown in FIG. 29 reveal that binding of the 237 antibody falls off with more than four Ala substitutions, where binding by the 237 CAR-T cell does not diminish until at least 5 Ala residues have been substituted into the wild-type OTS-8 peptide epitope. These results confirm the broader binding range of the 237 CAR-T cell relative to the parent 237 antibody, an unexpected finding.

Another experiment was designed to assess the capacity of the various binding agents to bind to OTS-8 variants that differed in length. The binding assay compared 237 antibody binding and 237 CAR-T cell binding to immobilized OTS-8 length variants. The OTS-8 length variants were a series of OTS-8 variants beginning with the 4-Ala substitute (see above), the OTS-8 variant of greatest divergence from wild-type OTS-8 that was still bound by both the 237 antibody and the 237 CAR-T cell. The length variants involved a progressive shortening of the epitope peptide by one Ala residue deleted from the C-terminus, yielding a nested set of OTS-8 length variants. For 237 antibody binding, a colorimetric assay was used with results detected at $OD_{450}$. For the 237 CAR-T cell, activation was measured by IFNγ production. FIG. 30 shows that 237 antibody binding diminished when a second Ala residue was removed, but activation of the 237 CAR-T cell did not diminish until a third Ala residue was removed. These results are consistent with the experiments on binding to OTS-8 variants described above that demonstrate the fewer requirements for binding, and thus the broader binding range for cancer cells, exhibited by the 237 CAR-T cell compared to the parent 237 antibody.

Example 10

Variants of 237 scFv with Broadened Specificity

In order to broaden the number of Tn-linked cancer antigens that can be targeted with a single reagent, such as a CAR or a BiTE, 237 scFv mutants were sought that could bind to several members of the mucin family of proteins, which have been shown to be upregulated in a variety of human cancers. For example, MUC1 is upregulated in breast cancer, colon cancer, multiple myeloma, lymphoma and myeloid leukemia; MUC4 is upregulated in colon and pancreatic cancer; and MUC16 is upregulated in pancreatic and ovarian cancer (80, 83, 85, 93, 94, 96, 104, 105, 106, 121, 123, 134). MUC16 is diagnostically very significant as its extracellular portion (also known as CA125) is shed into blood, and is established as a biomarker for diagnosing and monitoring ovarian cancer patients in FDA-approved assays (83).

Mucin proteins contain tandem repeat structures containing multiple N- and O-linked glycosylation sites. They are normally heavily glycosylated, and their aberrant glycosylation leads to formation of several Tn-linked antigens during cancer, which are expected to be recognizable, and thus targetable, by 237 scFv mutants (and ultimately, 237 CARs and BiTEs). While the pathways and the enzymes involved in glycosylation have been extensively studied, there seems to be limited knowledge about the exact sequence of Tn antigens arising from these mucin proteins. Several antibodies have been isolated that bind to the CA125 epitope of MUC16, e.g., OC125-like antibodies, M11-like antibodies, OV197-like antibodies and 5E11. While it has been challenging to precisely identify the epitopes of these antibodies, 5E11 was generated against a minimal epitope (FNTTER; SEQ ID NO:14) (84, 110, 111). In terms of offering therapeutic advantage, an OC125-like antibody (B43.13) that binds with high affinity ($K_D$ of 0.1 nM) to tandem repeats of MUC16 was shown to induce immune responses in patients that led to improvement in overall survival, and currently this therapy is in clinical trials (NCT03162562, NCT03100006) (116). Additionally, a CAR based on another MUC16-directed antibody (4H11) has been shown to be effective against human ovarian cancer cell lines, and in mouse models of human ovarian cancer, and is also in clinical trials currently (NCT02498912) (88, 90). Interestingly, most of these antibodies have been shown to recognize epitopes on MUC16 that are not glycosylated (84, 97, 110, 111). Regarding MUC4, the 8G7 antibody was isolated against the STGDTTPLPVTDTSSV (SEQ ID NO:15) epitope and its binding was also not dependent on the level of glycosylation (117). Another study established a MUC4 peptide (GHAT(GalNAc)PLPVTD; SEQ ID NO:16) that could be glycosylated (135). In the case of MUC1, 5E5 antibody that binds with Tn-MUC1 (VT(GalNAc)SAPDTR-PAPGS(GalNAc)T(GalNAc)APPAHG; SEQ ID NO:17) with high affinity ($K_D$ of 1.7 nM) was isolated by Clausen and colleagues (35, 36, 106). They also isolated additional Tn-MUC1 antibodies (for example, 2D9 and VU3C6) and established their minimal epitope requirements in MUC1, i.e., the GSTA motif for antibodies 5E5 and 2D9, and the PDTR motif for the VU3C6 antibody (5). Clausen and colleagues also demonstrated the presence of autoantibodies against MUC1 peptides in serum of breast, ovarian and prostate cancer patients (48), indicating the importance of MUC1 as a target for cancer therapy. The inventors thus investigated whether 237 scFv mutants could target a Tn epitope of a mucin family protein expected to be associated with cancer.

Figure 33:
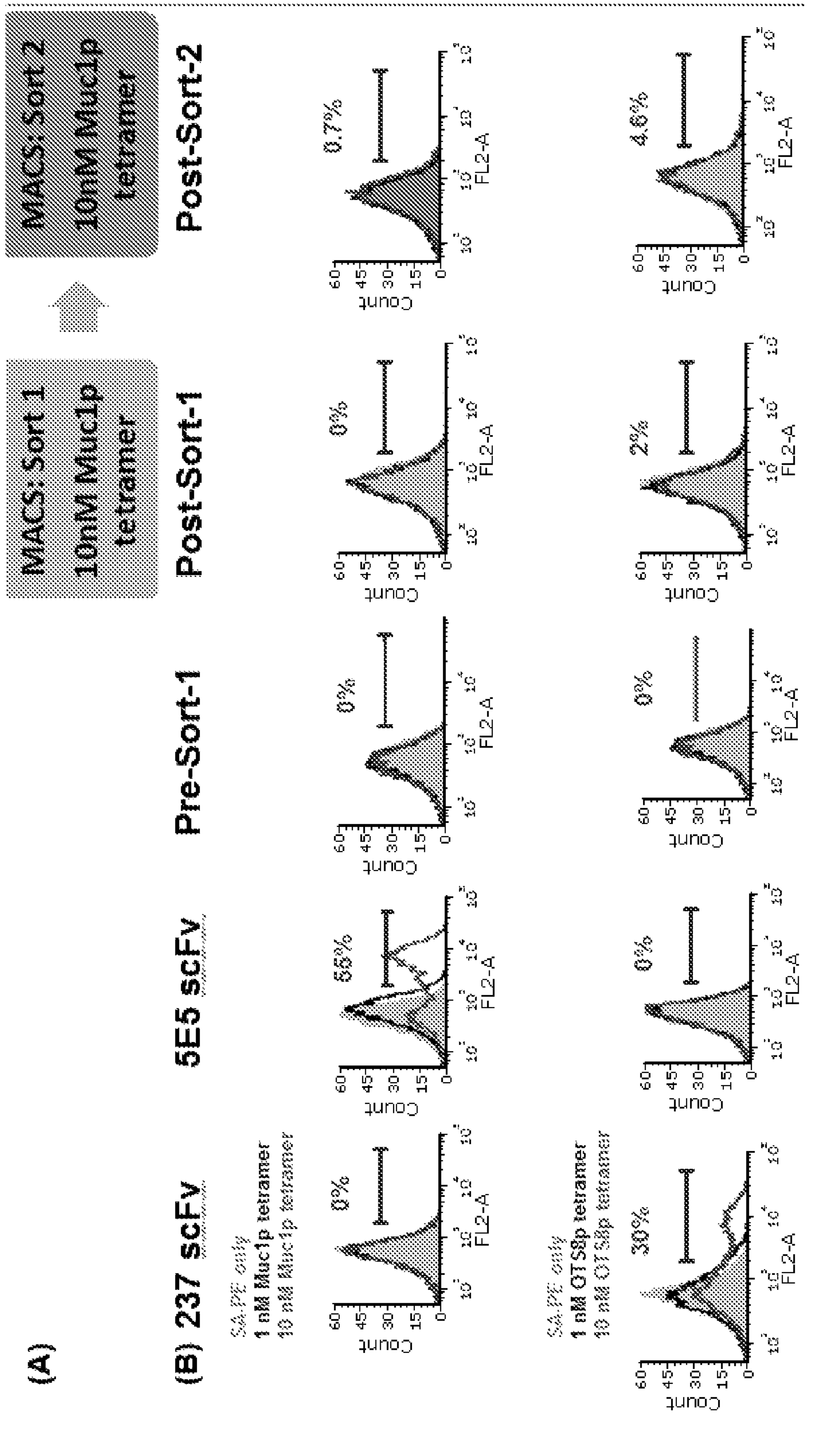
FIG. 33. Sorting 237 CDR libraries to isolate mutants that bind to non-cognate ligand (Tn-Muc1p). (A) The progression of various sorts of 237 libraries, including the technique used (MACS/FACS), and the sorting reagent (Tn-Muc1 peptide as tetramer or monomer) is shown. (B) 237 scFv, 5E5 scFv as well as the various stages of 237 libraries (Pre-sort and post-sort) were stained with various concentrations of Tn-Muc1 or Tn-OTS8 peptide as tetramer to determine the ligand concentration for subsequent sort, and to track enrichment. Marker populations indicate increase in percent positive population compared to negative control (in gray).
Figure 34:
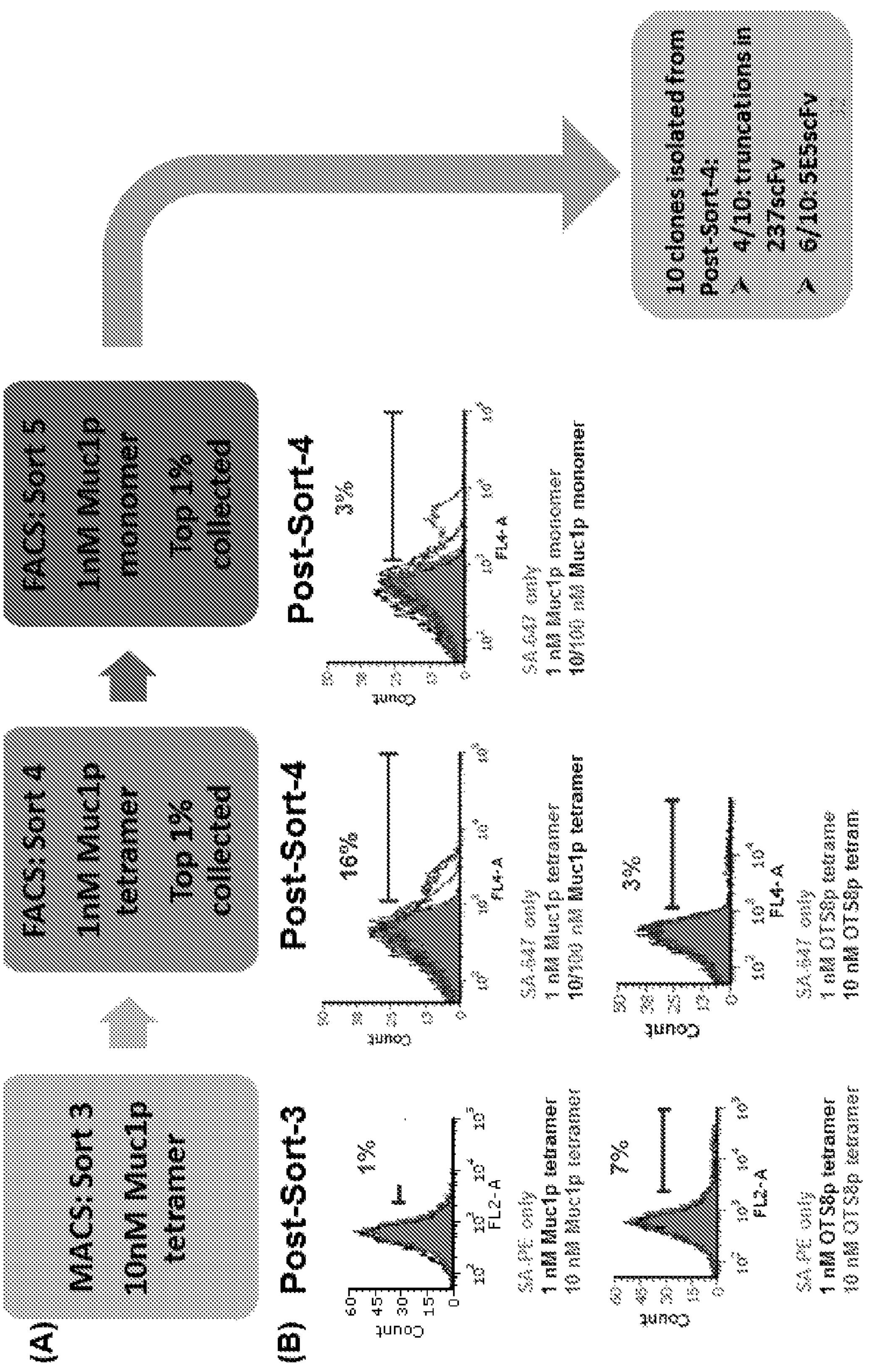
FIG. 34. Sorting 237 CDR libraries to develop binding to non-cognate ligand (Tn-Muc1p). (A) The progression of various sorts of 237 libraries, including the technique used (MACS/FACS), and the sorting reagent (Tn-Muc1 peptide as tetramer or monomer) is shown. (B) Various stages of sorted 237 libraries were stained with various concentrations of Tn-Muc1 or Tn-OTS8 peptide as tetramer to determine the ligand concentration for subsequent sort, and to track enrichment. Marker populations indicate increase in percent positive population compared to negative control (in gray).
Figure 35:
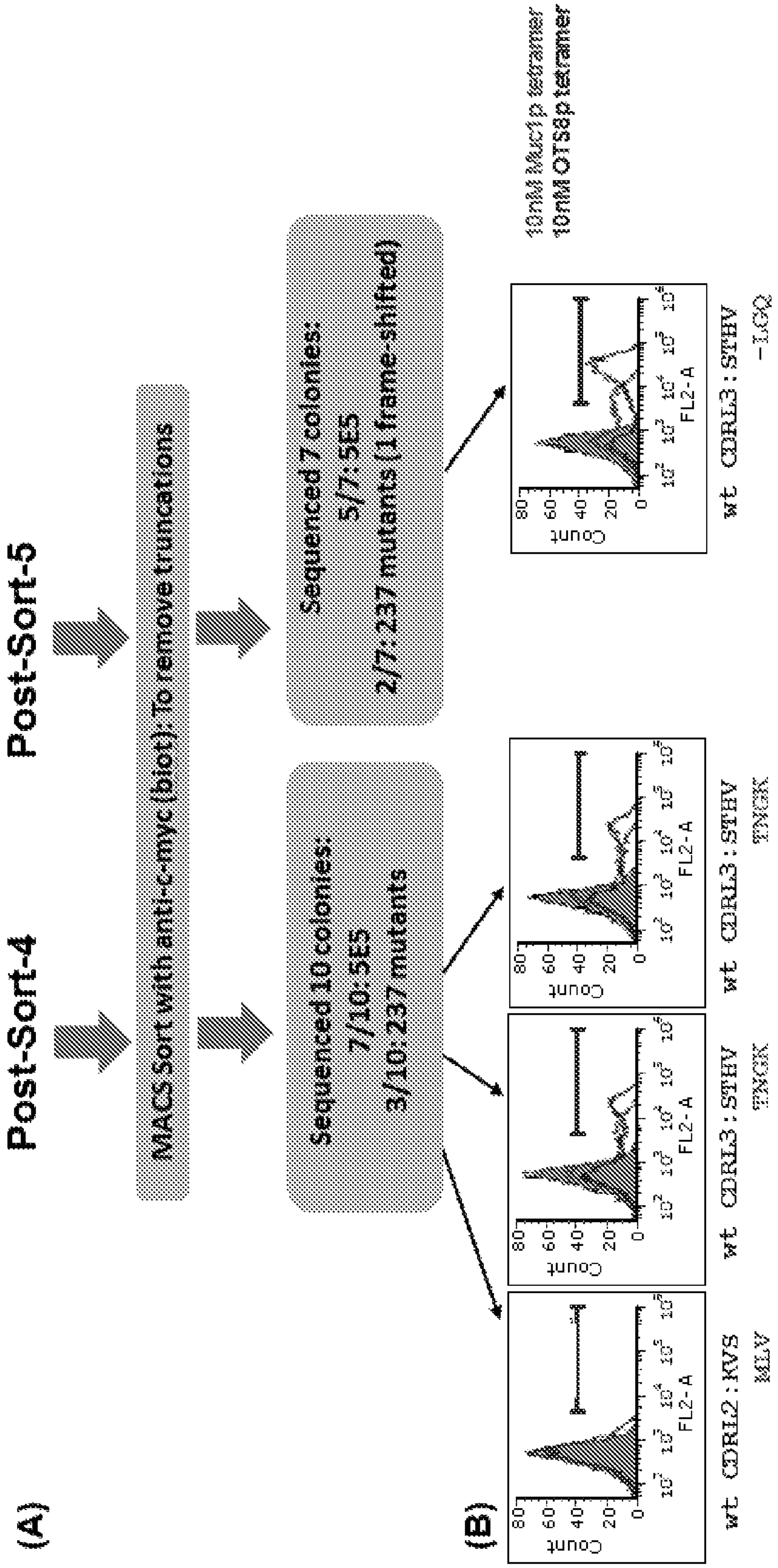
FIG. 35. Further sorting of 237 CDR libraries identified mutants that bound to non-cognate ligand (Tn-Muc1p). (A) In order to get rid of truncations from Tn-Muc1-sorted libraries (FIG. 34), the 237 scFv libraries were sorted with anti-c-myc. Single colonies were cultured, and plasmid DNA isolated from them was sequenced. (B) Certain clones (237 scFv mutants only) were stained with 10 nM Tn-OTS8 peptide tetramer, or 10 nM Tn-Muc1p tetramer, and analyzed by flow cytometry. As indicated, two unique mutants (TNGK and LGQ) were identified that stained with both Tn-OTS8 peptide and Tn-Muc1 peptide tetramers. The sequence of wild-type (wt) and mutated residues is shown in black and maroon, respectively.

The experimental design reflected an interest in isolating 237 scFv mutants that could either bind to an antigen of choice (for example, Tn-MUC1 peptide), or have broadened specificity so as to target multiple Tn-linked antigens (for example, both Tn-MUC1 and Tn-OTS8 peptides). As a starting point, 237 libraries were sorted with a Tn-MUC1p peptide (FIG. 33, 34, 35). After several MACS sorts, two 237 scFv mutants were obtained that bound not only to their natural Tn-OTS8 peptide antigen, but also to Tn-MUC1 peptide (FIG. 35). CAR derivatives of these mutants with "dual-specificity" were designed, and introduced into mouse T cells to assess their effectiveness against several cell lines that express Tn antigen on their surface. In order to assess their affinity to both Tn-OTS8 peptide and Tn-Muc1 peptide, CAR-transduced T cells were titrated with various concentrations of each peptide. As shown in FIG. 38, 237-CAR exhibited binding to low concentrations (10 nM) of its natural ligand (Tn-OTS8p) due to high sensitivity in the CAR format, but also unexpectedly bound to high concentrations (1 μM) of Tn-Muc1p. On the other hand, the CARs with dual specificity (i.e., 237-TNGK-CAR and 237-LGQ-CAR) exhibited dose-dependent binding to both Tn-OTS8p and Tn-Muc1p. When comparing activation assays with various target lines, these CARs with dual specificity surprisingly exhibited higher activation with Jurkat cells (a human cell line that lacks murine OTS8), compared to 237-WE-CAR, which is specific to Tn-OTS8p and the wild-type 237-CAR. 237-TNGK-CAR and 237-LGQ-CAR were also able to recognize Tn-linked antigens on murine cell lines (Ag104A and ID8 Cosmc KO) due to their broadened specificity. No activation was observed with cell lines lacking mutated Cosmc (ACosmc/ID8/$58^{-/-}$). These observations demonstrated for the first time that the specificity of 237 can be changed (broadened) to target multiple Tn-linked antigens hence provide a powerfully flexible approach to cancer treatment in general. The results disclosed herein establish that 237 scFv mutants can be developed that possess novel Tn-specificities and the results establish that 237 libraries can be sorted with other Tn-linked cancer antigens (e.g., MUC4 or MUC16) that are associated with various human cancers, resulting in new therapeutics and diagnostics useful in recognizing and treating cancer.

Figure 48:
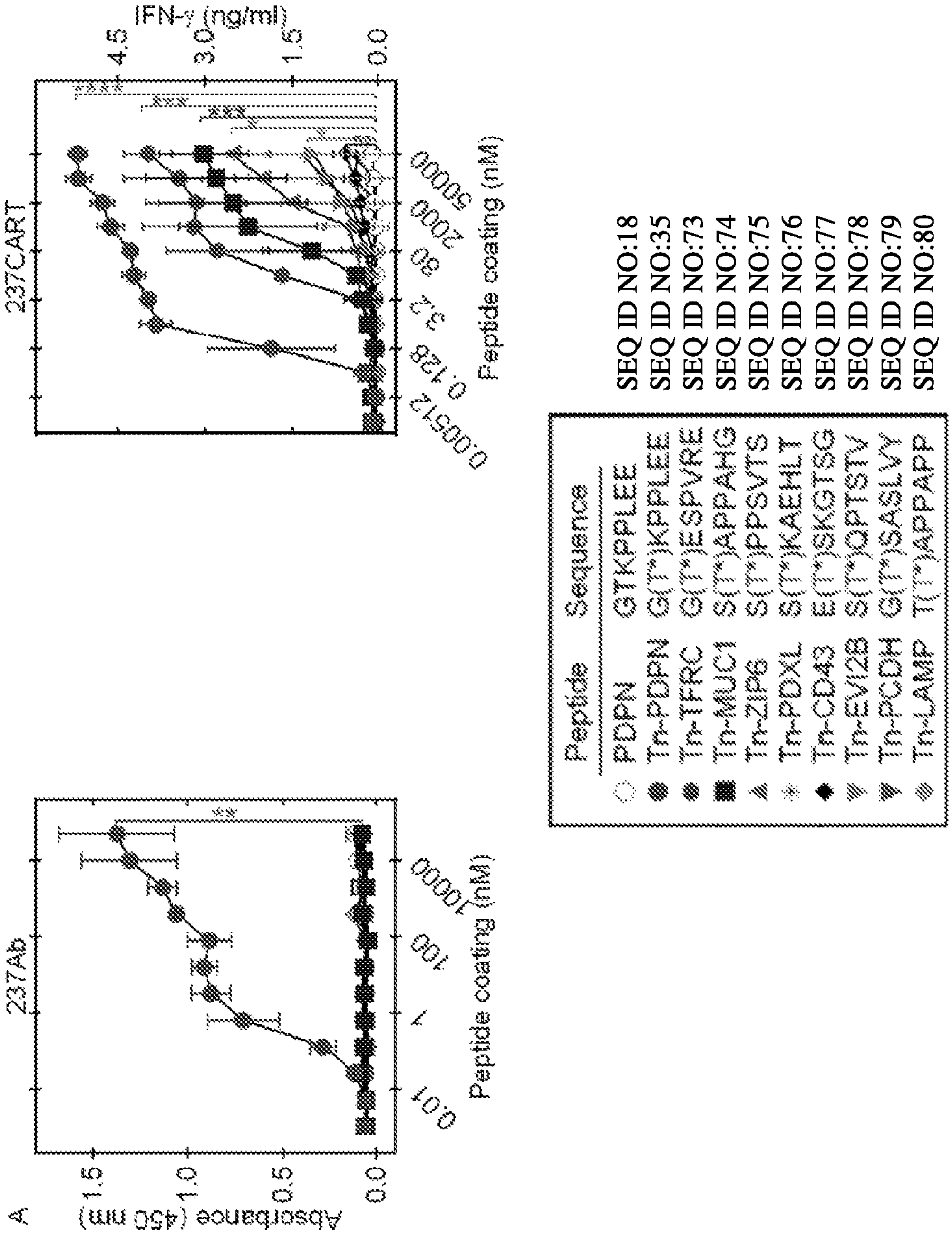
FIG. 48. CART cells derived from a Tn-glycopeptide-specific Ab can recognize multiple different Tn-glycopeptide epitopes expressed on different surface molecules. 237 CART cells made from the Tn-mPDPN-specific 237Ab recognize multiple different Tn-glycopeptides from Jurkat cells. 237Ab binding (left) would not have predicted the cross-reactivity of 237CART cells (right).

Because Jurkat cells were effectively eliminated by 237CART cells even though Jurkat cells lacked Tn-mPDPN, the reactivity of 237CART cells to other Tn-glycopeptide antigens found in Jurkat cells was tested. 237Ab binding can be detected only with Tn-mPDPN, whereas 237CART cells reacted with multiple Tn-glycopeptides from Jurkat cells at different levels. 237CART cells made from the Tn-m-PDPN-specific 237Ab recognize multiple different Tn-glycopeptides from Jurkat cells. 237Ab binding would not have predicted the cross-reactivity of 237CART cells (FIG. 48).

Figure 31:
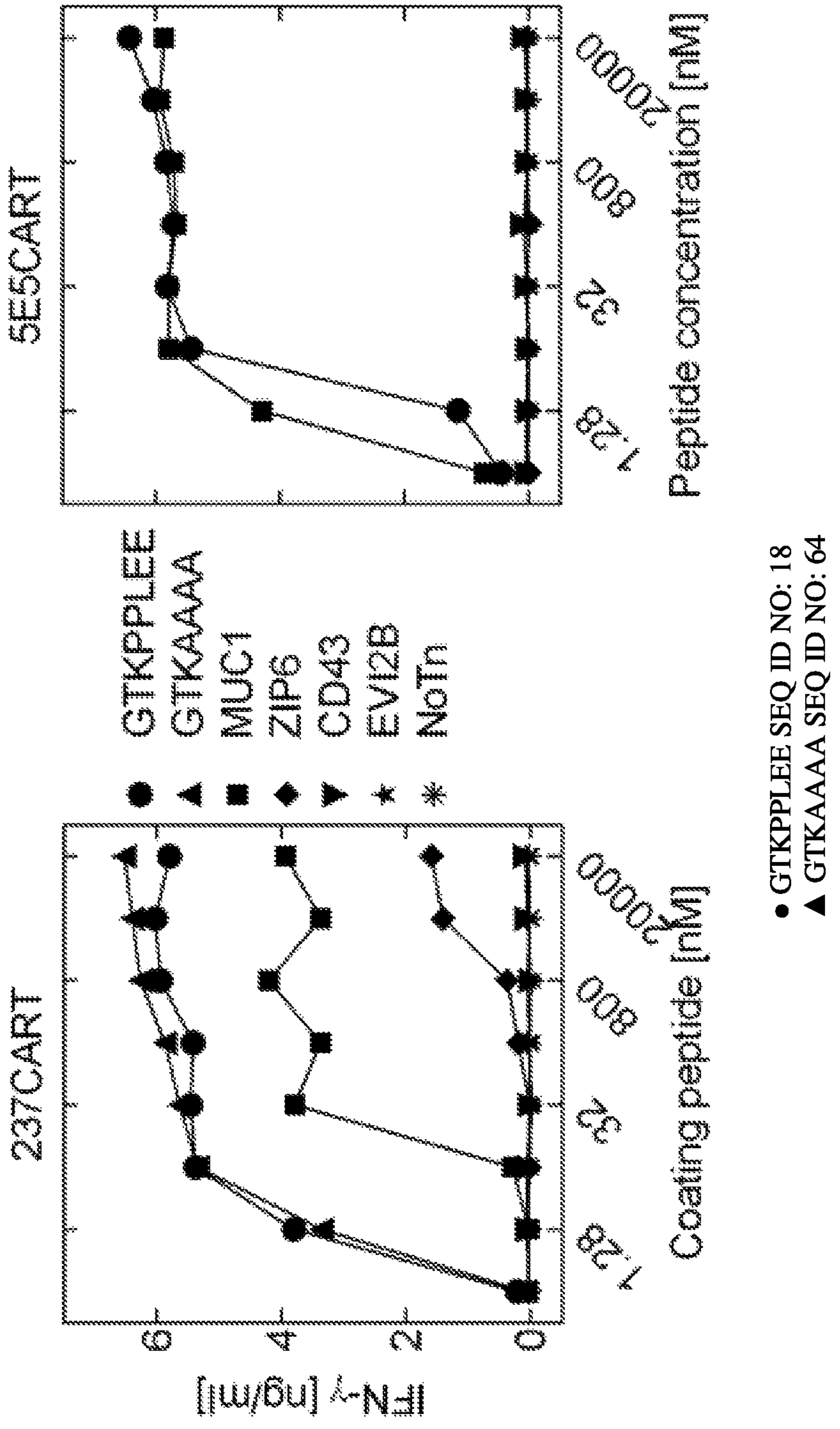
FIG. 31. CAR-T cell recognition of different glycopeptides. Activation of 237 CAR-T cells was compared to activation of 5E5 CAR-T cells upon exposure to varying concentrations of a number of different peptides coated on microtiter wells. The peptides coated on the wells were wild-type Podoplanin (GTKPPLEE; SEQ ID NO:18), Podoplanin bearing four Ala substitutions in the 237 antibody binding site (GTKAAAA; SEQ ID NO:10), MUC1, ZIP6, CD43, EV12B and NoTn. IFN-γ secretion levels of the 237 CAR-T cells and 5E5 CAR-T cells were measured following exposure to one of the coated peptides.
Figure 43:
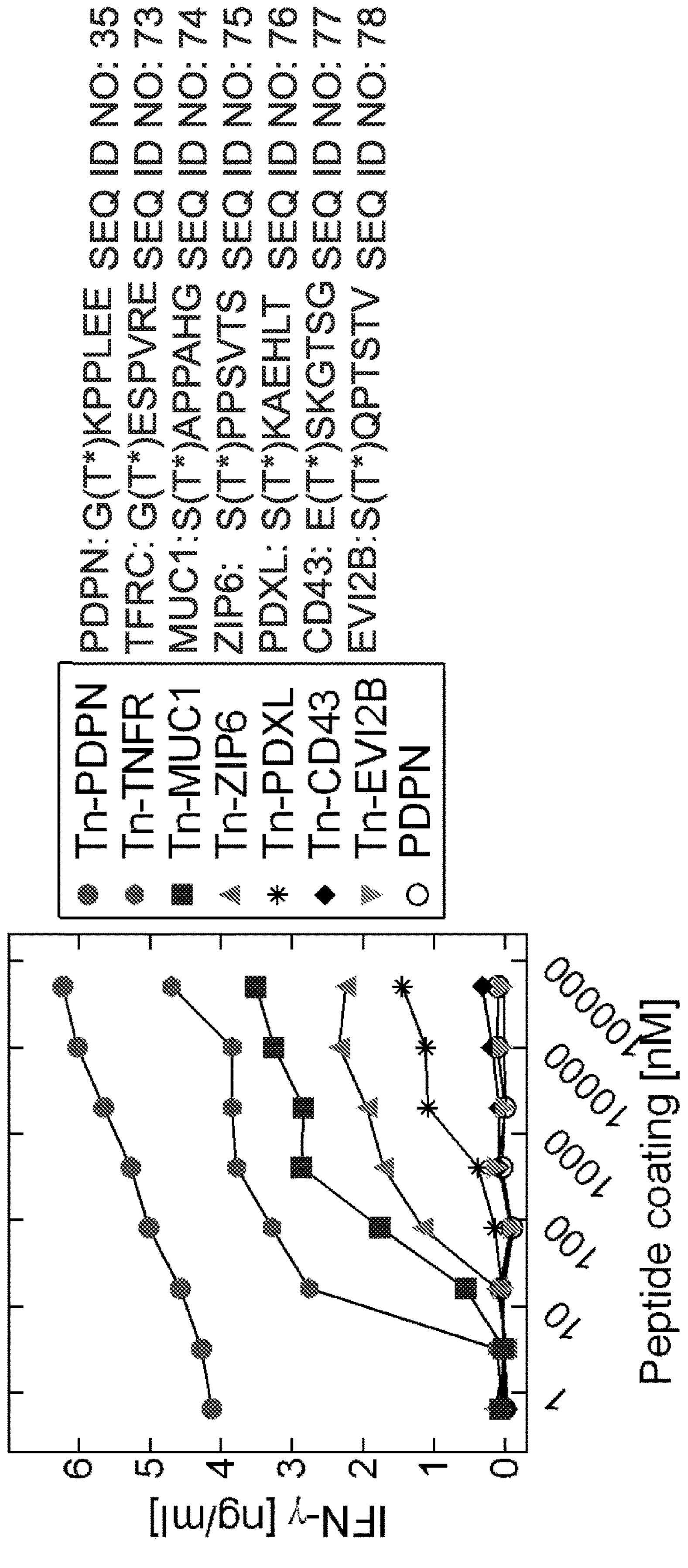
FIG. 43. 237 CAR-T cell recognition of multiple Tn glycopeptides. 237 CAR-T cells recognize a wider range of Tn-glycopeptides than what is predicted by 237 Antibody binding. 237 CAR-T cells recognize a variety of different Tn-glycopeptides. Biotinylated Tn glycopeptides were chemically synthesized and immobilized on streptavidin-coated plates. 237 CAR-T cell recognition was tested by determining the level of IFN-gamma release by 5000 237 CAR-T cells into the supernatant after 24 hours co-incubation with immobilized peptides on plate surfaces.
Figure 49:
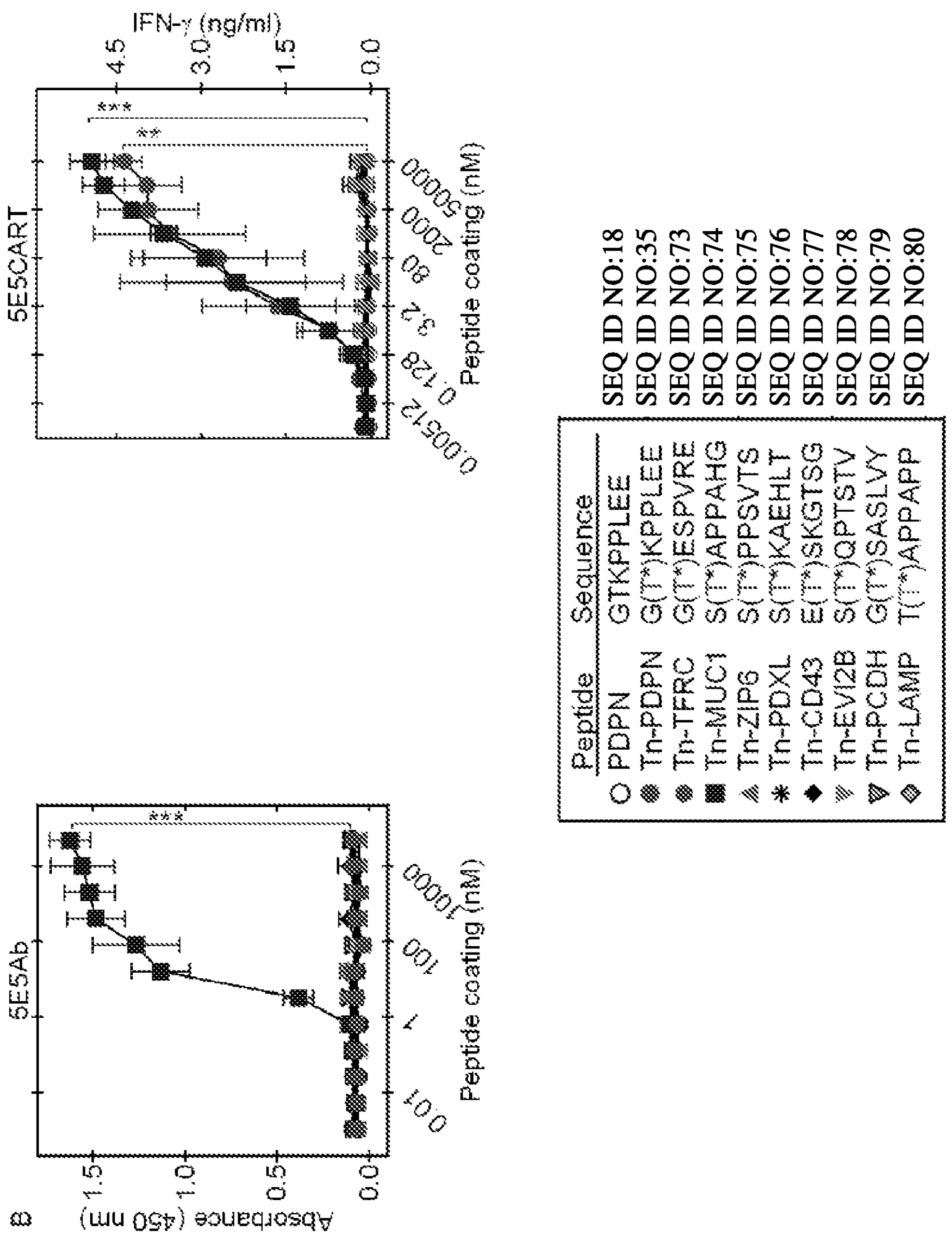
FIG. 49. CART derived from a Tn-glycopeptide-specific Ab can recognize multiple different Tn-glycopeptide epitopes expressed on different surface molecules. The specific binding of 5E5Ab to Tn-MUC1 would not have predicted the reactivity of 5E5CART cells to Tn-mPDPN. No other Tn-glycopeptides, however, were recognized by the 5E5CART cells.

To test the generality of these observations, a different Tn-glycopeptide-specific antibody, converted into the single-chain CAR format and expressed on T cells, was examined to determine whether it would cross-react with other Tn-glycopeptides. The 5E5CAR was derived from 5E5Ab that had been generated by immunizing a mouse with Tn-glycosylated human mucin 1 (Tn-MUC1). Consistent with the foregoing, an experiment was conducted that revealed that the 237 CAR-T cell bound to a broader range of different peptides than a CAR-T cell constructed based on an anti-MUC1 antibody, i.e., the 5E5 CAR-T cell, which recognizes a Tn epitope on MUC1. The following peptides were coated on microtiter wells: GTKPPLEE (SEQ ID NO:18), GTKAAAA (SEQ ID NO:10), MUC1, ZIP6, CD43, EV12B, and NoTn. All peptides except NoTn had O-glycosylation sites capable of forming a Tn epitope. The concentration of peptide coated in the wells varied from 1 nM to 20 μM. IFNγ production was used to measure activation. The 237 CAR-T cell was activated in the presence of all tested peptides except CD43, EV12B and NoTn (FIG. 31). While the 5E5Ab only recognized the Tn-MUC1, 5E5CART cells also recognized Tn-mPDPN, indicating that 5E5CART cells also recognized a Tn-glycopeptide not predicted by 5E5Ab binding. Interestingly, the pattern of cross-reactivity was different than that of 237CART cells because 5E5CART cells did not recognize any of the other Tn-glycopeptides tested (FIG. 49). In contrast, the 5E5 CAR-T cell was only activated in the presence of immobilized GTKPPLEE (SEQ ID NO:18) and MUC1 (FIG. 31). The data show that, in addition to exhibiting reduced requirements for a specific cancer epitope (OTS-8), the 237 CAR-T cell can recognize a greater variety of epitopes compared to the 5E5 CAR-T cell. Table 4 presents the epitope sequences of a number of peptides bound by the 237 CAR-T cell. In addition, a study was conducted with a variety of immobilized peptides exhibiting a Tn epitope being exposed to 237 CAR-T cells, and the results presented in FIGS. 43 and 44 show that CAR-T cells did bind to the various Tn peptides, inducing the expression of IFN-γ. The data support the position that the 237 CAR-T cell is a construct that recognizes the Tn epitope without constraints imposed by the amino acid sequence exhibiting the modified glycosylation pattern of the Tn epitope, in contrast to the protein-specific antibodies recognizing particular Tn epitopes, such as the Tn epitope of MUC1 recognized by the 5E5 CAR-T cell. 5E5CART cells recognized COSMC-mutant cancers independent of Tn-MUC1 or Tn-mPDPN expression. MUC1-knockout significantly compromised but did not abrogate recognition of COSMC-mutant SKOV3 cancer cells. Absence of MUC1 had no detectable influence on the 5E5CART cell recognition of Jurkat cells and knocking-out mPDPN affected Neuro2A cell recognition only marginally. Ag104A does not express Tn-MUC1 but was nevertheless recognized by 5E5CART cells. Mean±SEM, n=3. Importantly, 5E5CART cells not only killed cancers expressing Tn-MUC1 as reported (119), but also recognized COSMC mutant cancers that did not express MUC1, supporting the generality of the discovery made with 237CART cells.

Figure 32:
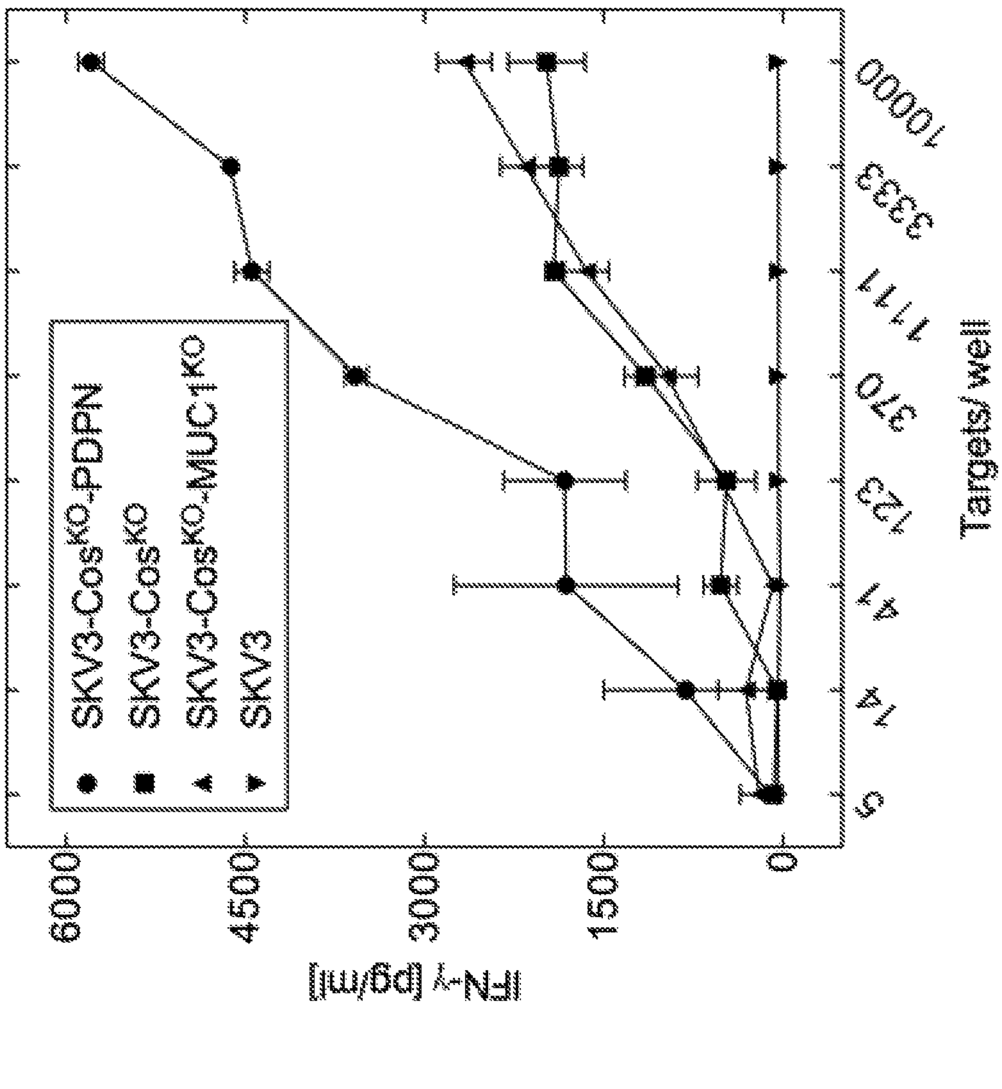
FIG. 32. MUC1 expression does not affect 237 CAR-T cell activation upon recognition of SKOVC3-Cosmc$^{KO}$. SKV3 in the inset refers to SKOV3. MUC1 is not required for 237 CAR-T activation. 5000 237 CAR-T cells per well of 96-well plate were incubated with target cancer cells at the number as indicated for 24 hours. The level of IFN-γ release into the supernatant was measured by sandwich ELISA.

Consistent with the foregoing observation, an experiment was conducted to determine if MUC1 expression would affect the activation of 237 CAR-T cells exposed to $Cosmc^-$ SKOV3 cancer cells. The experiment tested the effect of four target cells on 237 CAR-T cell activation using an activation assay in which each target was varied from 4 targets/well to 10000 targets/well, as shown in FIG. 32. The four target cells were SKOV3 cells that were $Cosmc^-$, $PDPN^-$ (SKV3-$Cos^{KO}$-PDPN); SKOV3 cells that were $Cosmc^-$, $PDPN^+$ (SKV3-$Cos^{KO}$; SKOV3 cells that were $Cosmc^-$, $MUC1^-$ (SKV3-$Cos^{KO}$-$MUC1^{KO}$; and SKOV3 cells (SKV3). The results presented in FIG. 32 show that SKOV3 cells did not activate the 237 CAR-T cell, but the $Cosmc^-$ $PDPN^-$ SKOV3 cancer cells did activate the 237 CAR-T cell. Moreover, the $Cosmc^-$ $PDPN^-$ SKOV3 cells did activate 237 CAR-T cells, but not to the same extent as the activation induced by $Cosmc^-$ $PDPN^-$ SKOV3 cells, reinforcing the observation that the Tn epitope recognized by the 237 CAR-T cell was not limited to the Tn epitope of PDPN. Finally, FIG. 32 shows that $Cosmc^-$ $MUC1^-$ SKOV3 cells activated 237 CAR-T cells to about the same extent as $Cosmc^-$ SKOV3 cells activated 237 CAR-T cells, demonstrating that MUC1 expression had no effect on 237 CAR-T cell activation.

TABLE 4

| | | | Sequence Identifier | (−1, +3) | −1 | 0 | +1 | +2 | +3 | +4 | +5 | +6 | (−1, +6) | score |
|---|---|---|---|---|---|---|---|---|---|---|---|---|---|---|
| + | PDPN | GTKPPLEE | 18 | 0 | 0 | 0 | 0 | 0 | 0 | 0 | 0 | 0 | 0 | |
| + | MUC1 | STAPPAHG | 37 | −3.4 | −2.7 | 0 | −0.7 | 0 | 0 | −1 | −6 | −1 | −10.9 | |
| − | CD43 | ETPHATSH | 38 | −5.18 | −0.3 | 0 | −0.8 | −4.1 | −0.7 | −3 | −1.2 | −3 | −12.9 | |
| 1 | Zinc transporter ZIP6 | STPPSVTS | 39 | −2.8 | −2.7 | 0 | −0.8 | 0 | 0.6 | 1 | −4 | −2 | −7.63 | |
| 3 | Protein EV12B | STQPTSTV | 40 | −3.23 | −2.7 | 0 | −0.6 | 0 | 0 | −2 | −4 | −1 | −9.95 | |
| 5 | LAMP1 | TTAPPAPP | 41 | −3.5 | −2.8 | 0 | −0.7 | 0 | 0 | −1 | −3 | −5 | −12.7 | |
| 6 | Podocalyxin | STKAEHLT | 42 | −3/9 | −2.7 | 0 | 0 | 0.3 | −1.6 | −0 | −6 | −3 | −13 | |
| 7 | CD43 | TTSITSDP | 43 | −4.47 | −2.8 | 0 | −1.7 | 0 | 0 | −2 | −1 | −5 | −11.9 | |
| 8 | Seizure 6-like protein 2 | TTAVTPNG | 44 | −5.21 | −2.8 | 0 | −0.7 | −1.7 | 0 | −5 | −2 | −1 | −13 | |
| 9 | Transferrin receptor protein 1 | GTESPVRE | 45 | −5.5 | 0 | 0 | −1.5 | −4 | 0 | 1 | −3 | 0 | −7.95 | |

Example 11

Cancer Treatment

Figure 40:
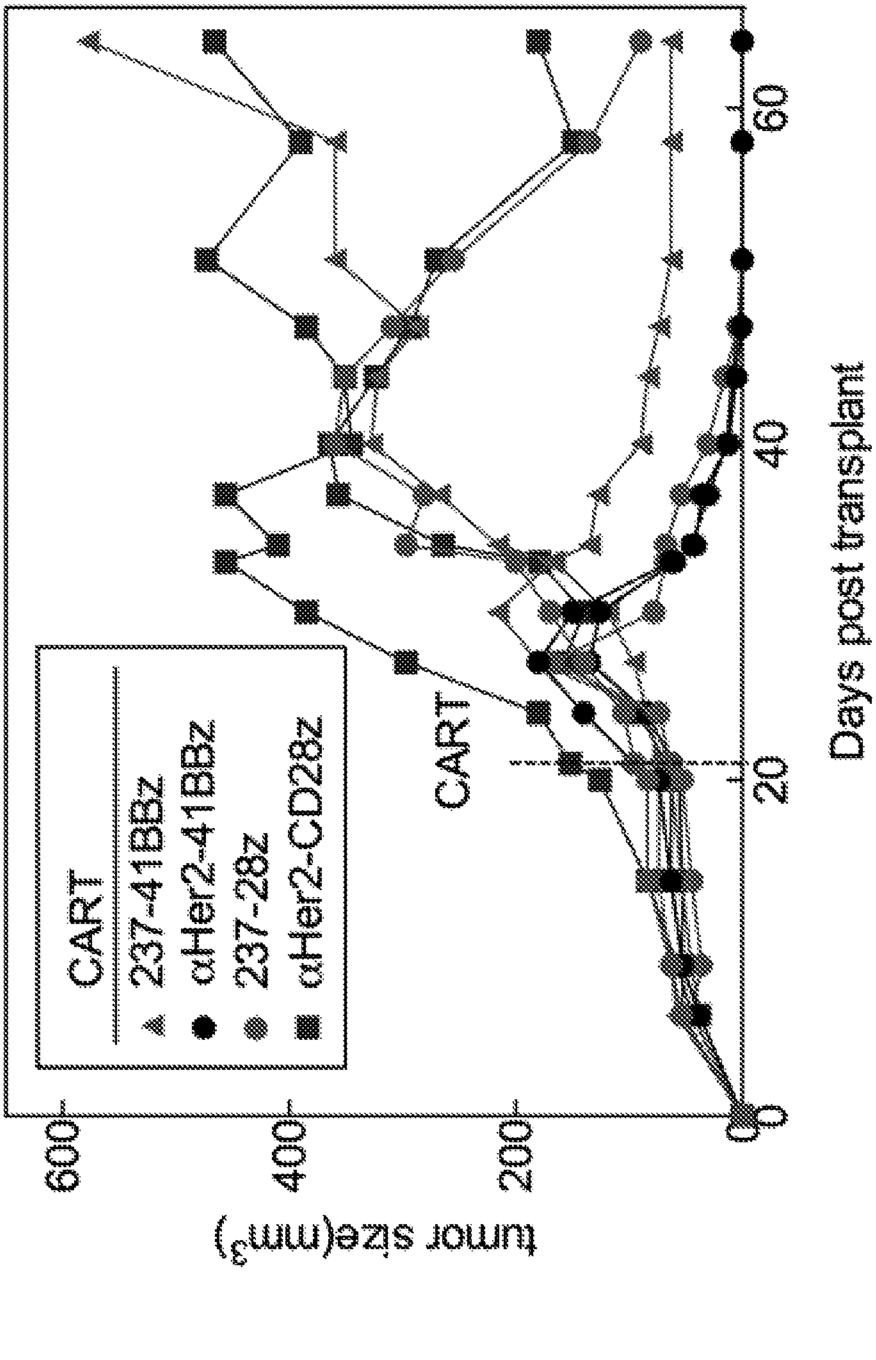
FIG. 40. Responses of SKOV3-Cosmc$^{KO-O1E}$ to CAR-T cell treatment. 237 CAR-T cells eradicate established cancers in vivo by recognizing Tn-glycopeptide epitopes not predicted by 237 full IgG binding. 237 CAR-T cell eradication of established solid tumor. 5 million SKOV3-COSMCKO-PDPN cells were s.c.-injected into each NSG mouse. 21 days post-transplantation, 5 million 237-41BBz or 237-28z transduced OT1Rag1KO T cells were given via i.p. injection. Injection of the same volume of PBS was also used as a negative control. Disease progression was followed by measuring tumor dimensions.
Figure 41:
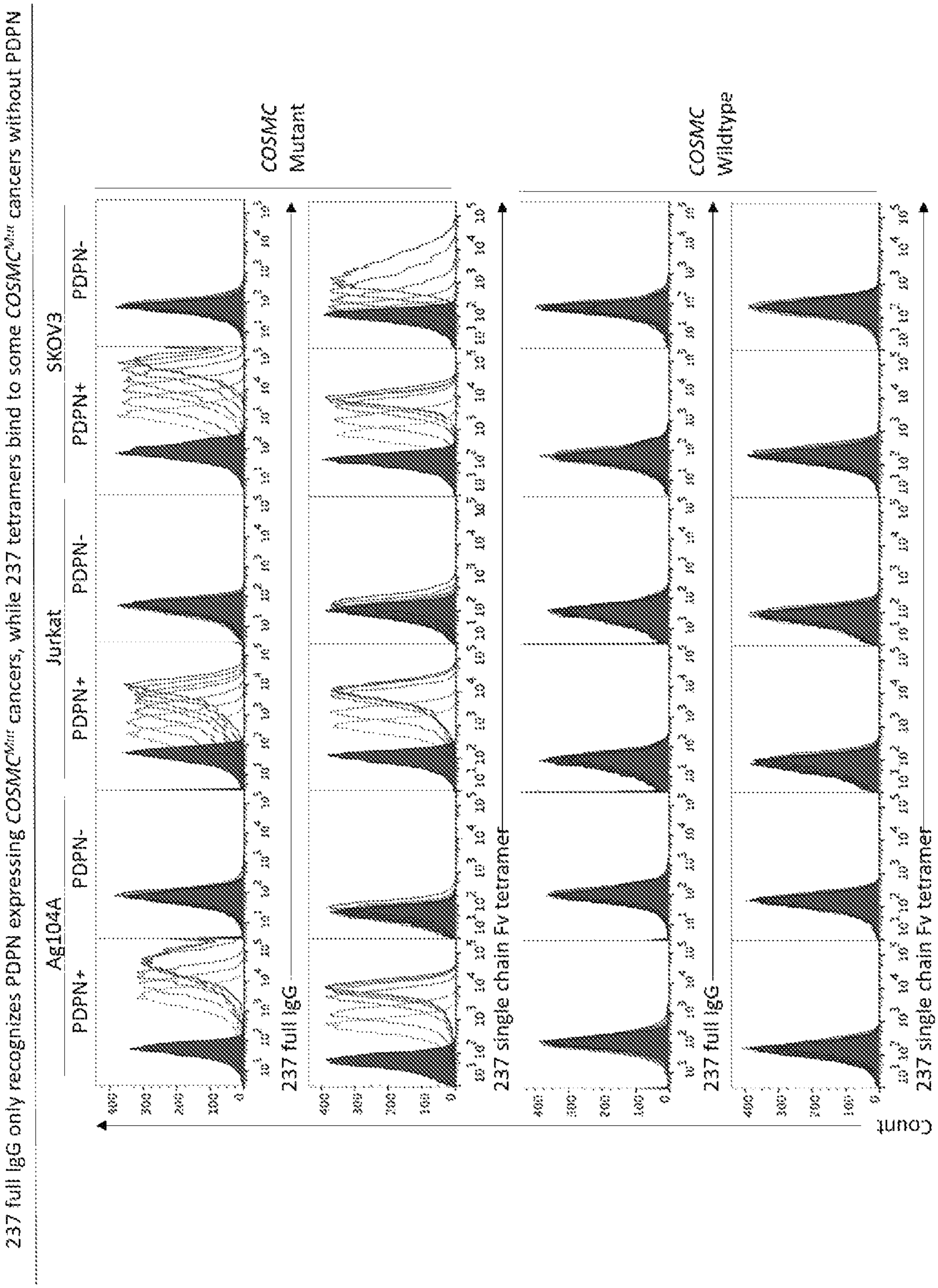
FIG. 41. Avidity improves the sensitivity of 237 Antibody recognizing COSMC mutant cancers that do not express PDPN. Serial 3-fold dilutions of 237 full IgG starting at the concentration of 3 μM, or 237 scFv tetramers starting at the concentration of 30 nM were used to stain cell lines: Ag104A, Jurkat and SKOV3 variants that are either COSMC mutant or wild-type, with or without PDPN expression. Ag104A is a murine sarcoma cell line that naturally carries a Cosmc null mutation and expresses murine podoplanin (PDPN). The two PDPN-negative variants were made by CRISPR-Cas9 knockout of Pdpn, and the two Cosmc wild-type variants were made by retroviral reconstitution of the wild-type Cosmc gene. Jurkat is a human T cell lymphoma cell line that naturally carries a COSMC null mutation. The two PDPN-expressing variants were made by retroviral transduction of murine Pdpn. The two COSMC wild-type variants were made by retroviral COSMC transduction. SKOV3 is a human ovarian cancer cell line with normal COSMC function. The two COSMC mutant variants were made by CRISPR-Cas9 knockout of COSMC. Both the COSMC knockout and the parental SKOV3 cell lines were transduced with Pdpn to generate the two PDPN-expressing variants.
Figure 42:
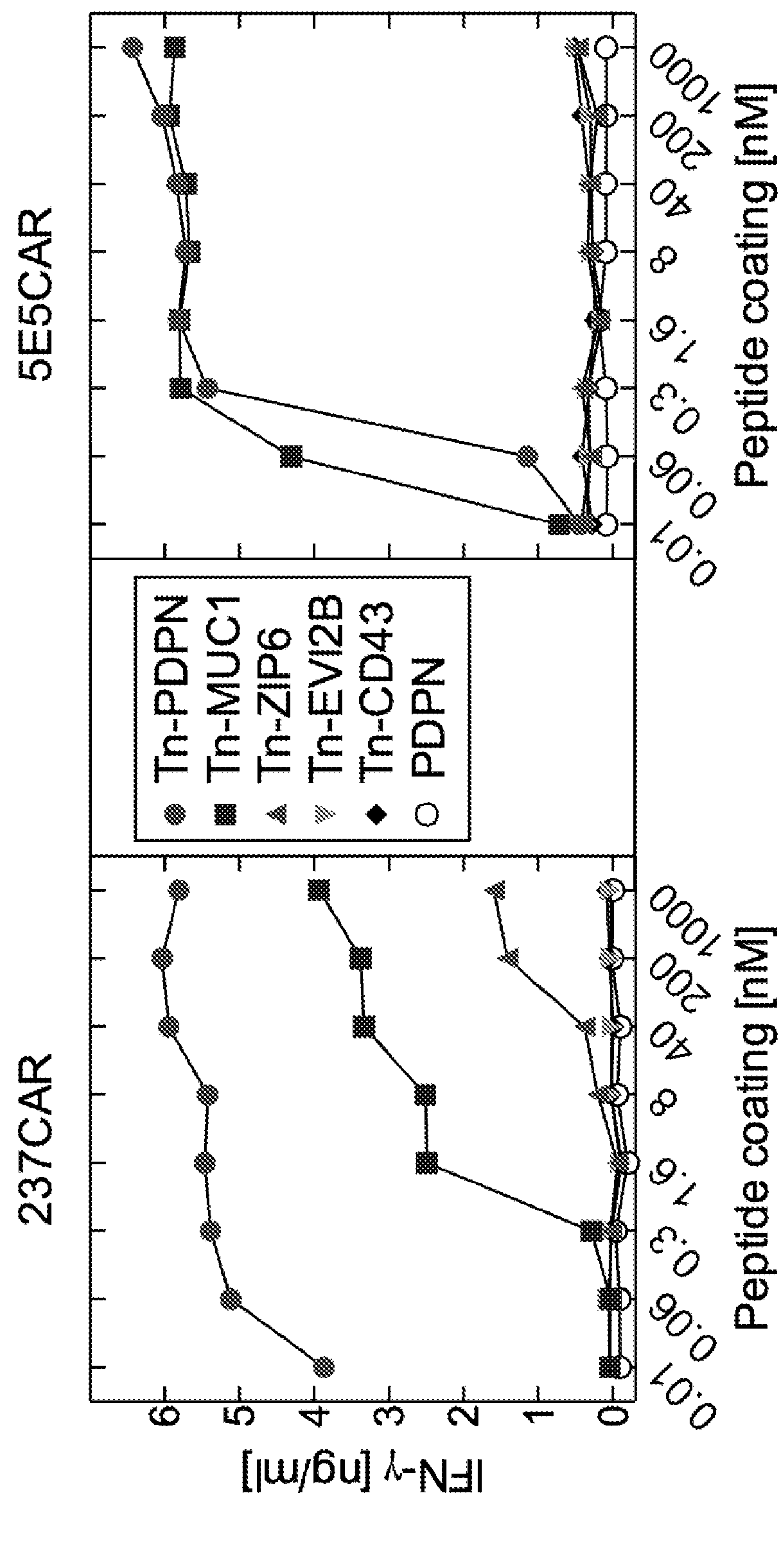
FIG. 42. Comparison of 237 CAR-T and 5E5 CAR-T cells recognizing different Tn-glycopeptides. Biotinylated Tn-glycopeptides were chemically synthesized and immobilized on streptavidin-coated plated. 237 CAR-T recognition was tested by determining the level of IFN-gamma release by 5000 237 CAR-T cells into the supernatant after 24 hours co-incubation with immobilized peptides on a plate surface.

An experiment was conducted to determine the effectiveness of the 237 CAR-T cell as an anti-cancer therapy in vivo. Mice were transplanted with SKOV3-COSMC$^{KO}$-PDPN cells and tumors were allowed to develop. Two separate trials were run with mice divided into four groups for treatment, i.e., group 1 received 237 CAR-T cell therapy using a (237)-(4-1BB)-(CD28ζ) CAR construct, group 2 received CAR-T cell therapy using an (α-Her2)-(4-1BB)-(CD28ζ) CAR construct, group 3 received CAR-T cell therapy using a (237)-(CD28ζ) construct, and group 4 received CAR-T cell therapy using an (α-Her2)-(CD28ζ) CAR construct. Tumor size was monitored over time, and the results are presented in FIG. 40. The results showed that the 237 CAR-T cell constructs were as effective, or better, than the α-Her2 CAR-T cell constructs at inhibiting tumor growth through about day 50 post-transplant of tumor cells. Additionally, the (237)-(CD28ζ) CAR-T cell appeared to be more effective at treating the tumor than the (237)-(4-1BB)-(CD28ζ) CAR-T cell, although the most effective treatment appeared to be the (α-Her2)-(4-1BBζ) CAR construct.

Although the specificity of an antibody predicts the reactivity of CARs derived from the antibody, proteins such as enzymes and antibodies may have polyfunctional combining regions for recognition of structurally related ligands. As disclosed herein, two different CARs exhibited cross-reactivity to structurally related but molecularly different ligands. This ability of the CART cells to recognize multiple different Tn-glycopeptides on Jurkat leukemia cells may have contributed to the absence of antigen loss variants (ALVs) and the long-term disease-free survival observed in in vivo experiments.

One of the mechanisms for the observed cross-reactivity could be an enhanced avidity of 237CARs compared to 237Ab. CART cells commonly express several 100,000 CARs per cell and use as few as 100-200 CAR engagements per cell to lyse a target. Without wishing to be bound by theory, recognition of multiple weak-binding or a few strong-binding Tn glycopeptide mimotopes may have a cumulative effect on signaling by the immunological synapse, and this could be the reason for 237CART cells recognizing multiple target molecules and different cancer cells. By contrast, 237Ab has only two binding sites and a flow-cytometric signal requires the presence of at least about 1000 epitopes for detecting any binding. A second, not mutually exclusive, explanation could be that the single-chain variable fragment (scFv) used for the 237CAR construction has an altered specificity. Construction of sc237CAR requires an artificial peptide linker to replace the natural disulfide bonds that link VH and VL of the 237Ab and this could possibly result in altered specificity.

Cumulative recognition of weak ligands or ligands expressed at very low levels could be problematic for CART cells, as this could lead to serious toxicity if the ligand were expressed on normal cells. Fortunately, in the case of the Tn-glycopeptide-specific 237CART cells, cross-reactions have only been detected with other Tn-glycopeptide antigens and remained cancer-specific because of the essential requirement of the GalNAc moiety (Tn) for 237 binding. The molecular basis of this observation may be explained by our previous crystallographic analyses showing that the 237mAb uses a deep pocket encoded entirely by germ-line residues of the antibody to envelop the GalNAc carbohydrate moiety completely and this seems to make binding entirely dependent on the presence of the carbohydrate moiety of the epitope. In the normally glycosylated normal cells, the Tn antigens are hidden by the extended O-linked glycosylation and therefore no longer fit inside the pocket. In addition to enveloping Tn within the pocket, there are also some interactions between the 237 complementarity determining regions (CDRs) and the peptide backbone, explaining the preference of 237CART cells to bind some Tn-glycopeptide antigens over others. Aberrant Tn expression can be found in various type of human cancers.

COSMC mutation is one major mechanism that leads to Tn expression, which can be found in 1-6% of human cancers across various cancer types (FIG. 3). Altered expression or localization of different types of GalNAc-transferases can lead to Tn-glycosylation as well. Epigenetic silencing of COSMC and/or T-synthase expression is another mechanism that results in stable Tn expression. Surface Tn expression has been exclusively found in cancers, except for a rare form of acquired hemolytic anemia (42). Thus, the exclusive cancer specificity and the broad recognition of various Tn-glycopeptide antigens makes the 237CART cell a desirable candidate for treating human cancers with Tn-expression on the cell surface.

Example 12 Methods and Materials

Mice. C57BL/6-Rag1$^{-/-}$ (B6.129S7-Rag1tm1Mom/J), OT-1(C57BL/6-Tg(TcraTcrb)1100Mjb/J) and NSGTM NOD.Cg-Prkdcscid Il2rgtm1Wjl/SzJ were purchased from the Jackson Laboratory (Bar Harbor, ME). The B6-Rag1$^{-/-}$ was subsequently bred to OT-1 to generate OT-1Rag$^{-/-}$ mice.

Cell lines. Ag104A and Neuro2A are spontaneous murine cancer cell lines lacking COSMC due to somatic cancer-specific Cosmc null mutations. COSMC-expressing variants were generated by retrovirally transducing a wild-type Cosmc pMFG vector. Ag104A naturally expresses high levels of mPDPN. mPDPN-negative Ag104A variants were made by CRISPR-Cas9 targeting exon 1 of Pdpn using the guiding sequence GAT ATT GTG ACC CCA GGT AC (SEQ ID NO:32). Jurkat is a human T cell leukemia line carrying a null mutation of COSMC. The Jurkat E6-1 cell line was either retrovirally transduced with mPDPN or we lentivirally truncated human CD19 (thCD19, which lacks the intracellular signaling domain) in tandem with the gene coding for wild-type COSMC linked by a P2A sequence. Neuro2A naturally lacks mPDPN. mPDPN-expressing variants of SKOV3, Jurkat and Neuro2A were made by retroviral transduction of Pdpn. SKOV3 and T47D are human cancer cell lines with normal COSMC function. COSMC was knocked out by CRISPR-Cas9 using CAC CGG GAC ACA TTA GGA TTG G (SEQ ID NO:33) as guiding sequence to target exon 1 of COSMC. Targeting exon 1 of MUC1 with the CRISPR-Cas9 guiding sequence CGG CCA CGG AAC CAG CTT CA (SEQ ID NO:34) was used to generate MUC1 knockout variants of SKOV3 and Jurkat cells. Cancer cell lines and their variants were maintained in DMEM except Jurkat lines were maintained in RPMI1640. Culture media were supplemented with 10% FCS.

CRISPR-Cas9 vectors. For CRISPR/Cas9-mediated gene knockouts, guiding sequences (gsRNA) were generated using the gsRNA designer from the Broad Institute and cloned over a BbsI side into the vector pSPCas9(BB)-2A-GFP (PX458, Addgene) as described (145). Cell lines were transfected by calcium phosphate and sorted for GFP-positive populations using FACSAriaII.

Flow cytometry. Samples were incubated with primary Abs followed by secondary APC-goat anti-mouse IgG(H+L) polyclonal Ab (SouthernBiotech). Cytometry data were collected on LSR II (BD Bioscience), and analyzed by Flowjo (TreeStar). The binding ratio represents the value of median fluorescence intensity (MFI) of a cell line stained with primary and secondary Abs divided by the MFI when stained with the secondary Ab only. Typically, Ab staining of cell surface antigens is performed at concentrations of about 10 μg/ml (about 67 nM), but we started at 3000 nM concentrations.

T cell transduction. 237CAR, 5E5CAR or CD19CAR was retrovirally transduced into T cells isolated from OT-1Rag$^{-/-}$ splenocytes, as described in (146).

Cytokine release assay. IFN-γ released for 24 hours into the medium by the 10,000 CART cells upon recognition of stimulator cells or after co-incubation with immobilized peptides was measured by ELISA (146).

Cytotoxicity assay. The capability of CART cells to lyse target cells was evaluated in a 4-hour $^{51}$Cr release assay, as described (8).

Ab binding to peptides immobilized on plate surfaces. 50 μl of 10 μg/ml 237Ab or 5E5Ab was added to each well containing immobilized peptides and incubated for one hour at room temperature. Ab binding was detected by sandwich ELISA according to the manufacturer's protocol (Invitrogen).

Bioluminescence imaging. Jurkat cells were modified to express Click Beetle Green. $5\times10^6$ Jurkat cells were injected through the tail vein and disease progression was monitored by weekly bioluminescence imaging on a Xenogen IVIS-200 Spectrum camera (Perkin Elmer), as described (119).

Statistical analysis. Data were analyzed using Prism software (GraphPad). For comparison of two groups with normally distributed data, the two-tailed Student's t-test was used. For comparison of non-parametric data, the Wilcoxon Rank Sum Test was employed. The significance level of the difference among the survival of animals from the different treatment groups was determined by the log-rank Mantel-Cox test. In the figure legends, ns stands for $P>0.05$, * stands for $P\leq0.05$, ** stands for $P\leq0.01$.

REFERENCES

1. Moreau, R., J. Dausset, J. Bernard, and J. Moullec. 1957. Acquired hemolytic anemia with polyagglutinability of erythrocytes by a new factor present in normal blood. Bull Mem Soc Med Hop Paris 73:569-587.
2. Dausset, J., J. Moullec, and J. Bernard. 1959. Acquired hemolytic anemia with polyagglutinability of red blood cells due to a new factor present in normal human serum (Anti-Tn). Blood 14:1079-1093.
3. Brooks, C. L., A. Schietinger, S. N. Borisova, P. Kufer, M. Okon, T. Hirama, C. R. Mackenzie, L. X. Wang, H. Schreiber, and S. V. Evans. 2010. Antibody recognition of a unique tumor-specific glycopeptide antigen. Proc Natl Acad Sci USA 107:10056-10061.
4. Steentoft, C., K. T. Schjoldager, E. Clo, U. Mandel, S. B. Levery, J. W. Pedersen, K. Jensen, O. Blixt, and H. Clausen. 2010. Characterization of an immunodominant cancer-specific O-glycopeptide epitope in murine podoplanin (OTS8). Glycoconj J 27:571-582.
5. Blixt, O., E. Clo, A. S. Nudelman, K. K. Sorensen, T. Clausen, H. H. Wandall, P. O. Livingston, H. Clausen, and K. J. Jensen. 2010. A high-throughput O-glycopeptide discovery platform for seromic profiling. J Proteome Res 9:5250-5261.
6. Monach, P. A., S. C. Meredith, C. T. Siegel, and H. Schreiber. 1995. A unique tumor antigen produced by a single amino acid substitution. Immunity 2:45-59.
7. Liu, R. B., B. Engels, A. Arina, K. Schreiber, E. Hyjek, A. Schietinger, D. C. Binder, E. Butz, T. Krausz, D. A. Rowley, B. Jabri, and H. Schreiber. 2012. Densely Granulated Murine NK Cells Eradicate Large Solid Tumors. Cancer Res 72:1964-1974.
8. Morgan, R. A., J. C. Yang, M. Kitano, M. E. Dudley, C. M. Laurencot, and S. A. Rosenberg. 2010. Case report of a serious adverse event following the administration of T cells transduced with a chimeric antigen receptor recognizing ERBB2. Mol Ther 18:843-851.
9. Parkhurst, M. R., J. C. Yang, R. C. Langan, M. E. Dudley, D. A. Nathan, S. A. Feldman, J. L. Davis, R. A. Morgan, M. J. Merino, R. M. Sherry, M. S. Hughes, U. S. Kammula, G. Q. Phan, R. M. Lim, S. A. Wank, N. P. Restifo, P. F. Robbins, C. M. Laurencot, and S. A. Rosenberg. 2011. T cells targeting carcinoembryonic antigen can mediate regression of metastatic colorectal cancer but induce severe transient colitis. Mol Ther 19:620-626.
10. Fong, Y. 2012. Minutes of the Recombinant DNA Advisory Committee, 6/19/12. In Recombinant DNA Advisory Committee. U.S. DEPARTMENT OF HEALTH AND HUMAN SERVICES, National Institutes of Health, Bethesda, MD 1-34.
11. Morgan, R. A., N. Chinnasamy, D. Abate-Daga, A. Gros, P. F. Robbins, Z. Zheng, M. E. Dudley, S. A. Feldman, J. C. Yang, R. M. Sherry, G. Q. Phan, M. S. Hughes, U. S.

Kammula, A. D. Miller, C. J. Hessman, A. A. Stewart, N. P. Restifo, M. M. Quezado, M. Alimchandani, A. Z. Rosenberg, A. Nath, T. Wang, B. Bielekova, S. C. Wuest, N. Akula, F. J. McMahon, S. Wilde, B. Mosetter, D. J. Schendel, C. M. Laurencot, and S. A. Rosenberg. 2013. Cancer Regression and Neurological Toxicity Following Anti-MAGE-A3 TCR Gene Therapy. J Immunother 36:133-151.

12. Ju, T., V. I. Otto, and R. D. Cummings. 2011. The Tn antigen-structural simplicity and biological complexity. Angew Chem Int Ed Engl 50:1770-1791.

13. Springer, G. F. 1984. T and Tn, general carcinoma autoantigens. Science 224:1198-1206.

14. Springer, G. F., and H. Tegtmeyer. 1981. Origin of anti-Thomsen-Friedenreich (T) and Tn agglutinins in man and in White Leghorn chicks. Br J Haematol 47:453-460.

15. Spiotto, M. T., P. Yu, D. A. Rowley, M. I. Nishimura, S. C. Meredith, T. F. Gajewski, Y. X. Fu, and H. Schreiber. 2002. Increasing tumor antigen expression overcomes "ignorance" to solid tumors via crosspresentation by bone marrow-derived stromal cells. Immunity 17:737-747.

16. Schietinger, A., M. Philip, B. A. Yoshida, P. Azadi, H. Liu, S. C. Meredith, and H. Schreiber. 2006. A mutant chaperone converts a wild-type protein into a tumor-specific antigen. Science 314:304-308.

17. Ju, T., G. S. Lanneau, T. Gautam, Y. Wang, B. Xia, S. R. Stowell, M. T. Willard, W. Wang, J. Y. Xia, R. E. Zuna, Z. Laszik, D. M. Benbrook, M. H. Hanigan, and R. D. Cummings. 2008. Human tumor antigens Tn and sialyl Tn arise from mutations in Cosmc. Cancer Res 68:1636-1646.

18. Prokop, O., and G. Uhlenbruck. 1969. [N-acetyl-D-galactosamine in tumor cell membranes: demonstration by means of Helix agglutinins]. Med Welt 46:2515-2519.

19. Springer, G. F., P. R. Desai, and I. Banatwala. 1974. Blood group MN specific substances and precursors in normal and malignant human breast tissues. Naturwissenschaften 61:457-458.

20. Springer, G. F., P. R. Desai, and I. Banatwala. 1975. Blood group MN antigens and precursors in normal and malignant human breast glandular tissue. J Natl Cancer Inst 54:335-339.

21. Hirohashi, S., H. Clausen, T. Yamada, Y. Shimosato, and S. Hakomori. 1985. Blood group A cross-reacting epitope defined by monoclonal antibodies NCC-LU-35 and -81 expressed in cancer of blood group O or B individuals: its identification as Tn antigen. Proc Natl Acad Sci USA 82:7039-7043.

22. Wen, F. T., R. A. Thisted, D. A. Rowley, and H. Schreiber. 2012. A systematic analysis of experimental immunotherapies on tumors differing in size and duration of growth. Oncoimmunology 1:172-178.

23. Coulie, P. G., F. Lehmann, B. Lethe, J. Herman, C. Lurquin, M. Andrawiss, and T. Boon. 1995. A mutated intron sequence codes for an antigenic peptide recognized by cytolytic T lymphocytes on a human melanoma. Proc. Natl. Acad. Sci. U.S.A 92:7976-7980.

24. Wölfel, T., M. Hauer, J. Schneider, M. Serrano, C. Wölfel, E. Klehmann-Hieb, E. De Plaen, T. Hankeln, K. H. Meyer zum Buschenfelde, and D. Beach. 1995. A p16INK4a-insensitive CDK4 mutant targeted by cytolytic T lymphocytes in a human melanoma. Science 269:1281-1284.

25. Dubey, P., R. C. Hendrickson, S. C. Meredith, C. T. Siegel, J. Shabanowitz, J. C. Skipper, V. H. Engelhard, D. F. Hunt, and H. Schreiber. 1997. The immunodominant antigen of an ultraviolet-induced regressor tumor is generated by a somatic point mutation in the DEAD box helicase p68. J. Exp. Med. 185:695-705.

26. Yang, L., C. Lin, and Z. R. Liu. 2005. Phosphorylations of DEAD box p68 RNA helicase are associated with cancer development and cell proliferation. Mol Cancer Res 3:355-363.

27. Suzuki, H. I., K. Yamagata, K. Sugimoto, T. Iwamoto, S. Kato, and K. Miyazono. 2009. Modulation of microRNA processing by p53. Nature 460:529-533.

28. Fuller-Pace, F. V. 2006. DExD/H box RNA helicases: multifunctional proteins with important roles in transcriptional regulation. Nucleic Acids Res 34:4206-4215.

29. Schreiber, K., A. Arina, B. Engels, M. T. Spiotto, J. Sidney, A. Sette, T. Karrison, R. R. Weichselbaum, D. A. Rowley, and H. Schreiber. 2012. Spleen cells from young but not old immunized mice eradicate large established cancers. Clin Cancer Res 18:2526-2533.

30. Apostolopoulos, V., E. Yuriev, P. A. Ramsland, J. Halton, C. Osinski, W. Li, M. Plebanski, H. Paulsen, and I. F. McKenzie. 2003. A glycopeptide in complex with MHC class I uses the GalNAc residue as an anchor. Proc Natl Acad Sci USA 100:15029-15034.

31. Napoletano, C., A. Rughetti, M. P. Agervig Tarp, J. Coleman, E. P. Bennett, G. Picco, P. Sale, K. Denda-Nagai, T. Irimura, U. Mandel, H. Clausen, L. Frati, J. Taylor-Papadimitriou, J. Burchell, and M. Nuti. 2007. Tumor-associated Tn-MUC1 glycoform is internalized through the macrophage galactose-type C-type lectin and delivered to the HLA class I and II compartments in dendritic cells. Cancer Res 67:8358-8367.

32. Ju, T. and R. D. Cummings. 2002. A unique molecular chaperone Cosmc required for activity of the mammalian core 1 beta 3-galactosyltransferase. Proc Natl Acad Sci USA 99:16613-16618.

33. Fu, J., B. Wei, T. Wen, M. E. Johansson, X. Liu, E. Bradford, K. A. Thomsson, S. McGee, L. Mansour, M. Tong, J. M. McDaniel, T. J. Sferra, J. R. Turner, H. Chen, G. C. Hansson, J. Braun, and L. Xia. 2011. Loss of intestinal core 1-derived O-glycans causes spontaneous colitis in mice. J Clin Invest 121:1657-1666.

34. Blixt, O., O. I. Lavrova, D. V. Mazurov, E. Clo, S. K. Kracun, N. V. Bovin, and A. V. Filatov. 2012. Analysis of Tn antigenicity with a panel of new IgM and IgG1 monoclonal antibodies raised against leukemic cells. Glycobiology 22:529-542.

35. Sorensen, A. L., C. A. Reis, M. A. Tarp, U. Mandel, K. Ramachandran, V. Sankaranarayanan, T. Schwientek, R. Graham, J. Taylor-Papadimitriou, M. A. Hollingsworth, J. Burchell, and H. Clausen. 2006. Chemoenzymatically synthesized multimeric Tn/STn MUC1 glycopeptides elicit cancer-specific anti-MUC1 antibody responses and override tolerance. Glycobiology 16:96-107.

36. Tarp, M. A., A. L. Sorensen, U. Mandel, H. Paulsen, J. Burchell, J. Taylor-Papadimitriou, and H. Clausen. 2007. Identification of a novel cancer-specific immunodominant glycopeptide epitope in the MUC1 tandem repeat. Glycobiology 17:197-209.

37. Van Elssen, C. H., P. W. Frings, F. J. Bot, K. K. Van de Vijver, M. B. Huls, B. Meek, P. Hupperets, W. T. Germeraad, and G. M. Bos. 2010. Expression of aberrantly glycosylated Mucin-1 in ovarian cancer. Histopathology 57:597-606.

38. Blixt, O., D. Bueti, B. Burford, D. Allen, S. Julien, M. Hollingsworth, A. Gammerman, I. Fentiman, J. Taylor-Papadimitriou, and J. M. Burchell. 2011. Autoantibodies to aberrantly glycosylated MUC1 in early stage breast cancer are associated with a better prognosis. Breast Cancer Res 13:R25.
39. Wang, Y., T. Ju, X. Ding, B. Xia, W. Wang, L. Xia, M. He, and R. D. Cummings. 2010. Cosmc is an essential chaperone for correct protein O-glycosylation. Proc Natl Acad Sci USA 107:9228-9233.
40. Xia, L., T. Ju, A. Westmuckett, G. An, L. Ivanciu, J. M. McDaniel, F. Lupu, R. D. Cummings, and R. P. McEver. 2004. Defective angiogenesis and fatal embryonic hemorrhage in mice lacking core 1-derived O-glycans. J Cell Biol 164:451-459.
41. Cloosen, S., J. Arnold, M. Thio, G. M. Bos, B. Kyewski, and W. T. Germeraad. 2007. Expression of tumor-associated differentiation antigens, MUC1 glycoforms and CEA, in human thymic epithelial cells: implications for self-tolerance and tumor therapy. Cancer Res 67:3919-3926.
42. Ju, T., and R. D. Cummings. 2005. Protein glycosylation: chaperone mutation in Tn syndrome. Nature 437:1252.
43. Schreiber, H., and D. A. Rowley. 1999. Inflammation and Cancer. In Inflammation: Basic Principles and Clinical Correlates. J. I. Gallin, and R. Snyderman, editors. Lippincott Williams & Wilkins, Philadelphia. 1117-1129.
44. Philip, M., D. A. Rowley, and H. Schreiber. 2004. Inflammation as a tumor promoter in cancer induction. Semin Cancer Biol 14:433-439.
45. Kudo, T., T. Iwai, T. Kubota, H. Iwasaki, Y. Takayma, T. Hiruma, N. Inaba, Y. Zhang, M. Gotoh, A. Togayachi, and H. Narimatsu. 2002. Molecular cloning and characterization of a novel UDP-Gal:GalNAc(alpha) peptide beta 1,3-galactosyltransferase (C1Gal-T2), an enzyme synthesizing a core 1 structure of O-glycan. J Biol Chem 277:47724-47731.
46. Vlad, A. M., S. Muller, M. Cudic, H. Paulsen, L. Otvos, Jr., F. G. Hanisch, and O. J. Finn. 2002. Complex carbohydrates are not removed during processing of glycoproteins by dendritic cells: processing of tumor antigen MUC1 glycopeptides for presentation to major histocompatibility complex class II-restricted T cells. J Exp Med 196:1435-1446.
47. Ninkovic, T., L. Kinarsky, K. Engelmann, V. Pisarev, S. Sherman, O. J. Finn, and F. G. Hanisch. 2009. Identification of O-glycosylated decapeptides within the MUC1 repeat domain as potential MHC class I (A2) binding epitopes. Mol Immunol 47:131-140.
48. Wandall, H. H., O. Blixt, M. A. Tarp, J. W. Pedersen, E. P. Bennett, U. Mandel, G. Ragupathi, P. O. Livingston, M. A. Hollingsworth, J. Taylor-Papadimitriou, J. Burchell, and H. Clausen. 2010. Cancer biomarkers defined by autoantibody signatures to aberrant O-glycopeptide epitopes. Cancer Res 70:1306-1313.
49. Kalos, M., B. L. Levine, D. L. Porter, S. Katz, S. A. Grupp, A. Bagg, and C. H. June. 2011. T cells with chimeric antigen receptors have potent antitumor effects and can establish memory in patients with advanced leukemia. Sci Transl Med 3:95ra73.
50. Porter, D. L., B. L. Levine, M. Kalos, A. Bagg, and C. H. June. 2011. Chimeric antigen receptor-modified T cells in chronic lymphoid leukemia. N Engl J Med 365:725-733.
51. Carpenito, C., M. C. Milone, R. Hassan, J. C. Simonet, M. Lakhal, M. M. Suhoski, A. Varela-Rohena, K. M. Haines, D. F. Heitjan, S. M. Albelda, R. G. Carroll, J. L. Riley, I. Pastan, and C. H. June. 2009. Control of large, established tumor xenografts with genetically retargeted human T cells containing CD28 and CD137 domains. Proc Natl Acad Sci USA 106:3360-3365.
52. Lanitis, E., M. Poussin, I. S. Hagemann, G. Coukos, R. Sandaltzopoulos, N. Scholler, and D. J. Powell, Jr. 2012. Redirected antitumor activity of primary human lymphocytes transduced with a fully human anti-mesothelin chimeric receptor. Mol Ther 20:633-643.
53. Zhao, Y., Q. J. Wang, S. Yang, J. N. Kochenderfer, Z. Zheng, X. Zhong, M. Sadelain, Z. Eshhar, S. A. Rosenberg, and R. A. Morgan. 2009. A herceptin-based chimeric antigen receptor with modified signaling domains leads to enhanced survival of transduced T lymphocytes and antitumor activity. J Immunol 183:5563-5574.
54. Ando, H., T. Matsushita, M. Wakitani, T. Sato, S. Kodama-Nishida, K. Shibata, K. Shitara, and S. Ohta. 2008. Mouse-human chimeric anti-Tn IgG1 induced antitumor activity against Jurkat cells in vitro and in vivo. Biol Pharm Bull 31:1739-1744.
55. Welinder, C., B. Baldetorp, C. Borrebaeck, B. M. Fredlund, and B. Jansson. 2011. A new murine IgG1 anti-Tn monoclonal antibody with in vivo anti-tumor activity. Glycobiology 21:1097-1107.
56. Li, Q., M. R. Anver, D. O. Butcher, and J. C. Gildersleeve. 2009. Resolving conflicting data on expression of the Tn antigen and implications for clinical trials with cancer vaccines. Mol Cancer Ther 8:971-979.
57. Yu, L. G. 2007. The oncofetal Thomsen-Friedenreich carbohydrate antigen in cancer progression. Glycoconj J 24:411-420.
58. Akita, K., S. Fushiki, T. Fujimoto, M. Inoue, K. Oguri, M. Okayama, I. Yamashina, and H. Nakada. 2001. Developmental expression of a unique carbohydrate antigen, Tn antigen, in mouse central nervous tissues. J Neurosci Res 65:595-603.
59. Stone, J. D., D. H. Aggen, A. Schietinger, H. Schreiber, and D. M. Kranz. 2012. A sensitivity scale for targeting T cells with chimeric antigen receptors (CARs) and bispecific T-cell Engagers (BiTEs). Oncoimmunology 1:863-873.
60. Ward, P. L., H. Koeppen, T. Hurteau, and H. Schreiber. 1989. Tumor antigens defined by cloned immunological probes are highly polymorphic and are not detected on autologous normal cells. J. Exp. Med. 170:217-232.
61. Milone, M. C., J. D. Fish, C. Carpenito, R. G. Carroll, G. K. Binder, D. Teachey, M. Samanta, M. Lakhal, B. Gloss, G. Danet-Desnoyers, D. Campana, J. L. Riley, S. A. Grupp, and C. H. June. 2009. Chimeric receptors containing CD137 signal transduction domains mediate enhanced survival of T cells and increased antileukemic efficacy in vivo. Mol Ther 17:1453-1464.
62. Sadelain, M., R. Brentjens, and I. Riviere. 2009. The promise and potential pitfalls of chimeric antigen receptors. Curr Opin Immunol 21:215-223.
63. Schreiber, H. 2013. Cancer Immunology. In Fundamental Immunology. W. E. Paul, editor Lippincott-Wlliams & Wilkins, Philadelphia, PA 1200-1234.
64. Schietinger, A., M. Philip, R. B. Liu, K. Schreiber, and H. Schreiber. 2010. Bystander killing of cancer requires the cooperation of CD4(+) and CD8(+) T cells during the effector phase. J Exp Med 207:2469-2477.
65. Bos, R., and L. A. Sherman. 2010. CD4+ T-cell help in the tumor milieu is required for recruitment and cytolytic function of CD8+ T lymphocytes. Cancer Res 70:8368-8377.
66. Zhang, B., T. Karrison, D. A. Rowley, and H. Schreiber. 2008. IFN-gamma- and TNF-dependent bystander eradication of antigen-loss variants in established mouse cancers. J Clin Invest 118:1398-1404.

67. Neeson, P., A. Shin, K. M. Tainton, P. Guru, H. M. Prince, S. J. Harrison, S. Peinert, M. J. Smyth, J. A. Trapani, M. H. Kershaw, P. K. Darcy, and D. S. Ritchie. 2010. Ex vivo culture of chimeric antigen receptor T cells generates functional CD8+ T cells with effector and central memory-like phenotype. Gene Ther 17:1105-1116.

68. Steentoft, C., S. Y. Vakhrushev, M. B. Vester-Christensen, K. T. Schjoldager, Y. Kong, E. P. Bennett, U. Mandel, H. Wandall, S. B. Levery, and H. Clausen. 2011. Mining the O-glycoproteome using zinc-finger nuclease-glycoengineered SimpleCell lines. Nat Methods 8:977-982.

69. Taupier, M. A., J. F. Kearney, P. J. Leibson, M. R. Loken, and H. Schreiber. 1983. Nonrandom escape of tumor cells from immune lysis due to intraclonal fluctuations in antigen expression. Cancer Res 43:4050-4056.

70. Gupta, P. B., C. M. Fillmore, G. Jiang, S. D. Shapira, K. Tao, C. Kuperwasser, and E. S. Lander. 2011. Stochastic state transitions give rise to phenotypic equilibrium in populations of cancer cells. Cell 146:633-644.

71. Guba, M., G. Cernaianu, G. Koehl, E. K. Geissler, K. W. Jauch, M. Anthuber, W. Falk, and M. Steinbauer. 2001. A primary tumor promotes dormancy of solitary tumor cells before inhibiting angiogenesis. Cancer Res 61:5575-5579.

72. Louis, C. U., B. Savoldo, G. Dotti, M. Pule, E. Yvon, G. D. Myers, C. Rossig, H. V. Russell, O. Diouf, E. Liu, H. Liu, M. F. Wu, A. P. Gee, Z. Mei, C. M. Rooney, H. E. Heslop, and M. K. Brenner. 2011. Antitumor activity and long-term fate of chimeric antigen receptor-positive T cells in patients with neuroblastoma. Blood 118:6050-6056.

73. Baeuerle, P. A., P. Kufer, and R. Bargou. 2009. BiTE: Teaching antibodies to engage T-cells for cancer therapy. Curr Opin Mol Ther 11:22-30.

74. Liddy, N., G. Bossi, K. J. Adams, A. Lissina, T. M. Mahon, N. J. Hassan, J. Gavarret, F. C. Bianchi, N. J. Pumphrey, K. Ladell, E. Gostick, A. K. Sewell, N. M. Lissin, N. E. Harwood, P. E. Molloy, Y. Li, B. J. Cameron, M. Sami, E. E. Baston, P. T. Todorov, S. J. Paston, R. E. Dennis, J. V. Harper, S. M. Dunn, R. Ashfield, A. Johnson, Y. McGrath, G. Plesa, C. H. June, M. Kalos, D. A. Price, A. Vuidepot, D. D. Williams, D. H. Sutton, and B. K. Jakobsen. 2012. Monoclonal TCR-redirected tumor cell killing. Nat Med 18(6):980-987.

75. Narni-Mancinelli, E., J. Chaix, A. Fenis, Y. M. Kerdiles, N. Yessaad, A. Reynders, C. Gregoire, H. Luche, S. Ugolini, E. Tomasello, T. Walzer, and E. Vivier. 2011. Fate mapping analysis of lymphoid cells expressing the NKp46 cell surface receptor. Proc Natl Acad Sci USA 108:18324-18329.

76. Brentjens, R. J., J. B. Latouche, E. Santos, F. Marti, M. C. Gong, C. Lyddane, P. D. King, S. Larson, M. Weiss, I. Riviere, and M. Sadelain. 2003. Eradication of systemic B-cell tumors by genetically targeted human T lymphocytes co-stimulated by CD80 and interleukin-15. Nat Med 9:279-286.

77. Davila, M. L., R. Brentjens, X. Wang, I. Riviere, and M. Sadelain. 2012. How do CARs work?: Early insights from recent clinical studies targeting CD19. Oncoimmunology 1:1577-1583.

78. Mukherjee, P., L. B. Pathangey, J. B. Bradley, T. L. Tinder, G. D. Basu, E. T. Akporiaye, and S. J. Gendler. 2007. MUC1-specific immune therapy generates a strong anti-tumor response in a MUC1-tolerant colon cancer model. Vaccine 25:1607-1618.

79. Liu, Q. P., G. Sulzenbacher, H. Yuan, E. P. Bennett, G. Pietz, K. Saunders, J. Spence, E. Nudelman, S. B. Levery, T. White, J. M. Neveu, W. S. Lane, Y. Bourne, M. L. Olsson, B. Henrissat, and H. Clausen. 2007. Bacterial glycosidases for the production of universal red blood cells. Nat Biotechnol 25:454-464.

80. Pedersen, J. W., O. Blixt, E. P. Bennett, M. A. Tarp, I. Dar, U. Mandel, S. S. Poulsen, A. E. Pedersen, S. Rasmussen, P. Jess, H. Clausen, and H. H. Wandall. 2011. Seromic profiling of colorectal cancer patients with novel glycopeptide microarray. Int J Cancer 128:1860-1871.

81. Altman J. D., Moss P. A. H., Goulder P. J. R., Barouch D. H., McHeyzer-Williams M. G., Bell J. I., McMicheal A. J. and Davis M. M. (1996) Phenotypic analysis of antigen-specific T lymphocytes. Science 274, 94-96.

82. Bargou R., Leo E., Zugmaier G., Klinger M., Goebeler M., Knop S., Noppeney R., Viardot A., Hess G., Schuler M., Einsele H., Brandl C., Wolf A., Kirchinger P., Klappers P., Schmidt M., Riethmuller G., Reinhardt C., Baeuerle P. A. and Kufer P. (2008) Tumor regression in cancer patients by very low doses of a T cell-engaging antibody. Science 321, 974-977.

83. Bast R. C., Jr., Klug T. L., St John E., Jenison E., Niloff J. M., Lazarus H., Berkowitz R. S., Leavitt T., Griffiths C. T., Parker L., Zurawski V. R., Jr. and Knapp R. C. (1983) A radioimmunoassay using a monoclonal antibody to monitor the course of epithelial ovarian cancer. N Engl J Med 309, 883-887.

84. Bressan A., Bozzo F., Maggi C. A. and Binaschi M. (2013) OC125, M11 and OV197 epitopes are not uniformly distributed in the tandem-repeat region of CA125 and require the entire SEA domain. Dis Markers 34, 257-267

85. Brossart P., Schneider A., Dill P., Schammann T., Grunebach F., Wirths S., Kanz L., Buhring H. J. and Brugger W. (2001) The epithelial tumor antigen MUC1 is expressed in hematological malignancies and is recognized by MUC1-specific cytotoxic T-lymphocytes. Cancer Res 61, 6846-6850.

87. Caruso H. G., Hurton L. V., Najjar A., Rushworth D., Ang S., Olivares S., Mi T., Switzer K., Singh H., Huls H., Lee D. A., Heimberger A. B., Champlin R. E. and Cooper L. J. (2015) Tuning Sensitivity of CAR to EGFR Density Limits Recognition of Normal Tissue While Maintaining Potent Antitumor Activity. Cancer Res 75, 3505-3518.

88. Chekmasova A. A., Rao T. D., Nikhamin Y., Park K. J., Levine D. A., Spriggs D. R. and Brentjens R. J. (2010) Successful eradication of established peritoneal ovarian tumors in SCID-Beige mice following adoptive transfer of T cells genetically targeted to the MUC16 antigen. Clin Cancer Res 16, 3594-3606.

89. Crawford F., Kozono H., White J., Marrack P. and Kappler J. (1998) Detection of antigen-specific T cells with multivalent soluble class II MHC covalent peptide complexes. Immunity 8, 675-682.

90. Dharma Rao T., Park K. J., Smith-Jones P., Iasonos A., Linkov I., Soslow R. A. and Spriggs D. R. (2010) Novel monoclonal antibodies against the proximal (carboxy-terminal) portions of MUC16. Appl Immunohistochem Mol Morphol 18, 462-472.

91. Doherty P. C. (2011) The tetramer transformation. J Immunol 187, 5-6.

92. Dolton G., Lissina A., Skowera A., Ladell K., Tungatt K., Jones E., Kronenberg-Versteeg D., Akpovwa H., Pentier J. M., Holland C. J., Godkin A. J., Cole D. K., Neller M. A., Miles J. J., Price D. A., Peakman M. and Sewell A. K. (2014) Comparison of peptide-major histocompatibility complex tetramers and dextramers for the identification of antigen-specific T cells. Clin Exp Immunol 177, 47-63.
93. Dyomin V. G., Palanisamy N., Lloyd K. O., Dyomina K., Jhanwar S. C., Houldsworth J. and Chaganti R. S. (2000) MUC1 is activated in a B-cell lymphoma by the t(1; 14)(q21; q32) translocation and is rearranged and amplified in B-cell lymphoma subsets. Blood 95, 2666-2671.
94. Fatrai S., Schepers H., Tadema H., Vellenga E., Daenen S. M. and Schuringa J. J. (2008) Mucin1 expression is enriched in the human stem cell fraction of cord blood and is upregulated in majority of the AML cases. Exp Hematol 36, 1254-1265.
95. Hadrup S. R., Bakker A. H., Shu C. J., Andersen R. S., van Veluw J., Hombrink P., Castermans E., Thor Straten P., Blank C., Haanen J. B., Heemskerk M. H. and Schumacher T. N. (2009) Parallel detection of antigen-specific T-cell responses by multidimensional encoding of MHC multimers. Nat Methods 6, 520-526.
96. Haridas D., Chakraborty S., Ponnusamy M. P., Lakshmanan I., Rachagani S., Cruz E., Kumar S., Das S., Lele S. M., Anderson J. M., Wittel U. A., Hollingsworth M. A. and Batra S. K. (2011) Pathobiological implications of MUC16 expression in pancreatic cancer. PLoS One 6, e26839.
97. Haridas D., Ponnusamy M. P., Chugh S., Lakshmanan I., Seshacharyulu P. and Batra S. K. (2014) MUC16: molecular analysis and its functional implications in benign and malignant conditions. FASEB J 28, 4183-4199.
98. Harris D. T., Hager M. V., Smith S. N., Cai Q., Stone J. D., Kruger P., Lever M., Dushek O., Schmitt T. M., Greenberg P. D. and Kranz D. M. (2018) Comparison of T Cell Activities Mediated by Human TCRs and CARs That Use the Same Recognition Domains. J Immunol 200, 1088-1100.
99. Harris D. T. and Kranz D. M. (2016) Adoptive T Cell Therapies: A Comparison of T Cell Receptors and Chimeric Antigen Receptors. Trends Pharmacol Sci 37, 220-230.
100. Hoffmann P., Hofmeister R., Brischwein K., Brandl C., Crommer S., Bargou R., Itin C., Prang N. and Baeuerle P. A. (2005) Serial killing of tumor cells by cytotoxic T cells redirected with a CD19-/CD3-bispecific single-chain antibody construct. Int J Cancer 115, 98-104.
101. Huang J., Zeng X., Sigal N., Lund P. J., Su L. F., Huang H., Chien Y. H. and Davis M. M. (2016) Detection, phenotyping, and quantification of antigen-specific T cells using a peptide-MHC dodecamer. PNAS 113, E1890-1897.
102. Ju T., Aryal R. P., Kudelka M. R., Wang Y. and Cummings R. D. (2014) The Cosmc connection to the Tn antigen in cancer. Cancer Biomark 14, 63-81.
103. Ju T. and Cummings R. D. (2002) A unique molecular chaperone Cosmc required for activity of the mammalian core 1 beta 3-galactosyltransferase. PNAS 99, 16613-16618.
104. Krishn S. R., Kaur S., Smith L. M., Johansson S. L., Jain M., Patel A., Gautam S. K., Hollingsworth M. A., Mandel U., Clausen H., Lo W. C., Fan W. T., Manne U. and Batra S. K. (2016) Mucins and associated glycan signatures in colon adenoma-carcinoma sequence: Prospective pathological implication(s) for early diagnosis of colon cancer. Cancer Lett 374, 304-314.
105. Kufe D. W. (2009) Mucins in cancer: function, prognosis and therapy. Nat Rev Cancer 9, 874-885.
106. Lavrsen K., Madsen C. B., Rasch M. G., Woetmann A., Odum N., Mandel U., Clausen H., Pedersen A. E. and Wandall H. H. (2013) Aberrantly glycosylated MUC1 is expressed on the surface of breast cancer cells and a target for antibody-dependent cell-mediated cytotoxicity. Glycoconj J 30, 227-236.
107. Liu X., Jiang S., Fang C., Yang S., Olalere D., Pequignot E. C., Cogdill A. P., Li N., Ramones M., Granda B., Zhou L., Loew A., Young R. M., June C. H. and Zhao Y. (2015) Affinity-Tuned ErbB2 or EGFR Chimeric Antigen Receptor T Cells Exhibit an Increased Therapeutic Index against Tumors in Mice. Cancer Res 75, 3596-3607.
108. Loffler A., Kufer P., Lutterbuse R., Zettl F., Daniel P. T., Schwenkenbecher J. M., Riethmuller G., Dorken B. and Bargou R. C. (2000) A recombinant bispecific single-chain antibody, CD19×CD3, induces rapid and high lymphoma-directed cytotoxicity by unstimulated T lymphocytes. Blood 95, 2098-2103.
109. Lynn R. C., Feng Y., Schutsky K., Poussin M., Kalota A., Dimitrov D. S. and Powell D. J., Jr. (2016) High-affinity FRbeta-specific CAR T cells eradicate AML and normal myeloid lineage without HSC toxicity. Leukemia 30, 1355-1364.
110. Marcos-Silva L., Narimatsu Y., Halim A., Campos D., Yang Z., Tarp M. A., Pereira P. J., Mandel U., Bennett E. P., Vakhrushev S. Y., Levery S. B., David L. and Clausen H. (2014) Characterization of binding epitopes of CA125 monoclonal antibodies. J Proteome Res 13, 3349-3359.
111. Marcos-Silva L., Ricardo S., Chen K., Blixt O., Arigi E., Pereira D., Hogdall E., Mandel U., Bennett E. P., Vakhrushev S. Y., David L. and Clausen H. (2015) A novel monoclonal antibody to a defined peptide epitope in MUC16. Glycobiology 25, 1172-1182.
112. Matsui K., Boniface J. J., Reay P. A., Schild H., de St. Groth B. F. and Davis M. M. (1991) Low affinity interaction of peptide-MHC complexes with T cell receptors. Science 254, 1788-1791.
113. Maude S. L., Frey N., Shaw P. A., Aplenc R., Barrett D. M., Bunin N. J., Chew A., Gonzalez V. E., Zheng Z., Lacey S. F., Mahnke Y. D., Melenhorst J. J., Rheingold S. R., Shen A., Teachey D. T., Levine B. L., June C. H., Porter D. L. and Grupp S. A. (2014) Chimeric antigen receptor T cells for sustained remissions in leukemia. N Engl J Med 371, 1507-1517.
114. Maude S. L., Laetsch T. W., Buechner J., Rives S., Boyer M., Bittencourt H., Bader P., Verneris M. R., Stefanski H. E., Myers G. D., Qayed M., De Moerloose B., Hiramatsu H., Schlis K., Davis K. L., Martin P. L., Nemecek E. R., Yanik G. A., Peters C., Baruchel A., Boissel N., Mechinaud F., Balduzzi A., Krueger J., June C. H., Levine B. L., Wood P., Taran T., Leung M., Mueller K. T., Zhang Y., Sen K., Lebwohl D., Pulsipher M. A. and Grupp S. A. (2018) Tisagenlecleucel in Children and Young Adults with B-Cell Lymphoblastic Leukemia. N Engl J Med 378, 439-448.
115. McCormack E., Adams K. J., Hassan N. J., Kotian A., Lissin N. M., Sami M., Mujic M., Osdal T., Gjertsen B. T., Baker D., Powlesland A. S., Aleksic M., Vuidepot A., Morteau O., Sutton D. H., June C. H., Kalos M., Ashfield R. and Jakobsen B. K. (2013) Bi-specific TCR-anti CD3 redirected T-cell targeting of NY-ESO-1- and LAGE-1-positive tumors. Cancer Immunol Immunother 62, 773-785.
116. Mobus V. J., Baum R. P., Bolle M., Kreienberg R., Noujaim A. A., Schultes B. C. and Nicodemus C. F.

(2003) Immune responses to murine monoclonal antibody-B43.13 correlate with prolonged survival of women with recurrent ovarian cancer. Am J Obstet Gynecol 189, 28-36.

117. Moniaux N., Varshney G. C., Chauhan S. C., Copin M. C., Jain M., Wittel U. A., Andrianifahanana M., Aubert J. P. and Batra S. K. (2004) Generation and characterization of anti-MUC4 monoclonal antibodies reactive with normal and cancer cells in humans. J Histochem Cytochem 52, 253-261.

118. Newell E. W., Klein L. O., Yu W. and Davis M. M. (2009) Simultaneous detection of many T-cell specificities using combinatorial tetramer staining. Nat Methods 6, 497-499.

119. Posey A. D., Jr., Schwab R. D., Boesteanu A. C., Steentoft C., Mandel U., Engels B., Stone J. D., Madsen T. D., Schreiber K., Haines K. M., Cogdill A. P., Chen T. J., Song D., Scholler J., Kranz D. M., Feldman M. D., Young R., Keith B., Schreiber H., Clausen H., Johnson L. A. and June C. H. (2016) Engineered CAR T Cells Targeting the Cancer-Associated Tn-Glycoform of the Membrane Mucin MUC1 Control Adenocarcinoma. Immunity 44, 1444-1454.

120. Radhakrishnan P., Dabelsteen S., Madsen F. B., Francavilla C., Kopp K. L., Steentoft C., Vakhrushev S. Y., Olsen J. V., Hansen L., Bennett E. P., Woetmann A., Yin G., Chen L., Song H., Bak M., Hlady R. A., Peters S. L., Opaysky R., Thode C., Qvortrup K., Schjoldager K. T., Clausen H., Hollingsworth M. A. and Wandall H. H. (2014) Immature truncated O-glycophenotype of cancer directly induces oncogenic features. PNAS 111, E4066-4075.

121. Ricardo S., Marcos-Silva L., Pereira D., Pinto R., Almeida R., Soderberg O., Mandel U., Clausen H., Felix A., Lunet N. and David L. (2015) Detection of glyco-mucin profiles improves specificity of MUC16 and MUC1 biomarkers in ovarian serous tumours. Mol Oncol 9, 503-512.

122. RodrIguez E., Schetters S. T. T. and van Kooyk Y. (2018) The tumour glyco-code as a novel immune checkpoint for immunotherapy. Nat Rev Immunol 18, 204-211.

123. Saitou M., Goto M., Horinouchi M., Tamada S., Nagata K., Hamada T., Osako M., Takao S., Batra S. K., Aikou T., Imai K. and Yonezawa S. (2005) MUC4 expression is a novel prognostic factor in patients with invasive ductal carcinoma of the pancreas. J Clin Pathol 58, 845-852.

124. Schietinger A., Philip M. and Schreiber H. (2008) Specificity in cancer immunotherapy. Semin Immunol 20, 276-285.

125. Schmitt T. M., Aggen D. H., Ishida-Tsubota K., Ochsenreither S., Kranz D. M. and Greenberg P. D. (2017) Generation of higher affinity T cell receptors by antigen-driven differentiation of progenitor T cells in vitro. Nat Biotechnol 35, 1188-1195.

126. Sharma P. and Kranz D. M. (2016) Recent advances in T-cell engineering for use in immunotherapy. F1000Res 5

127. Sharma P. and Kranz D. M. (2018) Subtle changes at the variable domain interface of the T-cell receptor can strongly increase affinity. J Biol Chem 293, 1820-1834.

128. Smith S. N., Wang Y., Baylon J. L., Singh N. K., Baker B. M., Tajkhorshid E. and Kranz D. M. (2014) Changing the peptide specificity of a human T-cell receptor by directed evolution. Nat Commun 5, 5223.

129. Sommermeyer D., Hill T., Shamah S. M., Salter A. I., Chen Y., Mohler K. M. and Riddell S. R. (2017) Fully human CD19-specific chimeric antigen receptors for T-cell therapy. Leukemia 31, 2191-2199.

130. Sommermeyer D., Hudecek M., Kosasih P. L., Gogishvili T., Maloney D. G., Turtle C. J. and Riddell S. R. (2016) Chimeric antigen receptor-modified T cells derived from defined CD8+ and CD4+ subsets confer superior antitumor reactivity in vivo. Leukemia 30, 492-500.

131. Sorensen A. L., Reis C. A., Tarp M. A., Mandel U., Ramachandran K., Sankaranarayanan V., Schwientek T., Graham R., Taylor-Papadimitriou J., Hollingsworth M. A., Burchell J. and Clausen H. (2006) Chemoenzymatically synthesized multimeric Tn/STn MUC1 glycopeptides elicit cancer-specific anti-MUC1 antibody responses and override tolerance. Glycobiology 16, 96-107.

132. Stone J. D., Artyomov M. N., Chervin A. S., Chakraborty A. K., Eisen H. N. and Kranz D. M. (2011) Interaction of streptavidin-based peptide-MHC oligomers (tetramers) with cell-surface TCRs. J Immunol 187, 6281-6290.

133. Sykulev Y., Brunmark A., Jackson M., Cohen R. J., Peterson P. A. and Eisen H. N. (1994) Kinetics and affinity of reactions between an antigen-specific T cell receptor and peptide-MHC complexes. Immunity 1, 15-22.

134. Takahashi T., Makiguchi Y., Hinoda Y., Kakiuchi H., Nakagawa N., Imai K. and Yachi A. (1994) Expression of MUC1 on myeloma cells and induction of HLA-unrestricted CTL against MUC1 from a multiple myeloma patient. J Immunol 153, 2102-2109.

135. Tarhan Y. E., Kato T., Jang M., Haga Y., Ueda K., Nakamura Y. and Park J. H. (2016) Morphological Changes, Cadherin Switching, and Growth Suppression in Pancreatic Cancer by GALNT6 Knockdown. Neoplasia 18, 265-272.

136. Tarp M. A., Sorensen A. L., Mandel U., Paulsen H., Burchell J., Taylor-Papadimitriou J. and Clausen H. (2007) Identification of a novel cancer-specific immunodominant glycopeptide epitope in the MUC1 tandem repeat. Glycobiology 17, 197-209.

137. Topp M. S., Kufer P., Gokbuget N., Goebeler M., Klinger M., Neumann S., Horst H. A., Raff T., Viardot A., Schmid M., Stelljes M., Schaich M., Degenhard E., Kohne-Volland R., Bruggemann M., Ottmann O., Pfeifer H., Burmeister T., Nagorsen D., Schmidt M., Lutterbuese R., Reinhardt C., Baeuerle P. A., Kneba M., Einsele H., Riethmuller G., Hoelzer D., Zugmaier G. and Bargou R. C. (2011) Targeted therapy with the T-cell-engaging antibody blinatumomab of chemotherapy-refractory minimal residual disease in B-lineage acute lymphoblastic leukemia patients results in high response rate and prolonged leukemia-free survival. J Clin Oncol 29, 2493-2498.

138. Zinn et al., 2008. "Noninvasive bioluminescence imaging in small animals." *ILAR J.* 49(1): 103-115.

139. Brentjens, R. J., Davila, M. L., Riviere, L, Park, J., Wang, X., Cowell, L. G., Bartido, S., Stefanski, J., Taylor, C., Olszewska, M. and Borquez-Ojeda, O., 2013. CD19-targeted T cells rapidly induce molecular remissions in adults with chemotherapy-refractory acute lymphoblastic leukemia. Science translational medicine, 5(177), pp. 177ra38-177ra38.

140. Grupp, S. A., Kalos, M., Barrett, D., Aplenc, R., Porter, D. L., Rheingold, S. R., Teachey, D. T., Chew, A., Hauck, B., Wright, J. F. and Milone, M. C., 2013. Chimeric antigen receptor-modified T cells for acute lymphoid leukemia. New England Journal of Medicine, 368(16), pp. 1509-1518.

141. Sun, X., Ju, T., Cummings, R. D., 2018. Differential expression of Cosmc, T-synthase and mucins in Tn-positive colorectal cancers. BMC Cancer 18:827.

142. Zlocowski, N., Grupe, V., Garay, Y. C., Nores, G. A., Lardone, R. D., and Irazoqui, F. J., 2019. Purified human anti-Tn and anti-T antibodies specifically recognize carcinoma tissues. Nature. 9:8097.
143. June, C H, Sadelain, M. 2018. Chimeric Antigen Receptor Therapy, N Engl J Med 379(1):64-73.
144. Movahedin, M., Brroks, T. M., Supekar, N. T., Gokanapudi, N., Boons, G. J., Brooks, C. L. 2017 Glycosylation of MUC1 influences the binding of a therapeutic antibody by altering the conformational equilibrium of the antigen. Glycobiology. 27(7):677-87.
145. Ran, F. A., Hsu, P. D., Wright, J., Agarwala, V., Scott, D. A., Zhang, F. 2013 Genome engineering using the CRISPR-Cas9 system. Nat Protoc 8(11):2281-308.
146. Leisegang, M., Engels, B., Schreiber, K., Yew, P. Y., Kiyotani., K., Idel, C., et al. 2016. Eradication of large solid tumors by gene therapy with a T-cell receptor targeting a single cancer-specific point mutation. Clin Cancer Res 22(11):2734-43.

Each of the references cited herein is hereby incorporated by reference in its entirety or in relevant part, as would be apparent from the context of the citation.

From the disclosure herein it will be appreciated that, although specific embodiments of the disclosure have been described herein for purposes of illustration, various modifications may be made without deviating from the spirit and scope of the disclosure.

What is claimed is:

1. A chimeric antigen receptor (CAR) that specifically binds a Tn glycopeptide comprising:

(a) a single chain variable fragment (scFv) that specifically binds a Tn glycopeptide, wherein the scFv comprises a heavy chain complementarity determining region 1 (CDRH1), a CDRH2, a CDRH3, a light chain complementarity determining region 1 (CDRL1), and a CDRL2 of SEQ ID NO: 19, and a CDRL3 comprising a variant sequence of TTWAP, STWAP, STWSP, STWGP, STWQP, STWEP, SVWEP, STWVP, STHQP, SLGQP, or TNGKP at positions 96-100 of SEQ ID NO: 19; and (b) a T-cell signaling domain.

2. The chimeric antigen receptor of claim 1, wherein the scFv is a variant of the wild-type scFv of antibody 237 comprising at least one amino acid variation from the wild-type antibody 237 light chain complementarity determining region 3 sequence at positions 96-100 of SEQ ID NO:19.

3. The chimeric antigen receptor of claim 1, wherein the CAR comprises an antibody 237 light chain complementarity determining region 3 sequence comprising the amino acids of positions 96-100 of SEQ ID NO:27.

4. The chimeric antigen receptor of claim 1, wherein the CAR comprises an antibody 237 light chain complementarity determining region 3 sequence comprising the amino acids of positions 96-100 of SEQ ID NO:28.

5. The chimeric antigen receptor of claim 1, wherein the CAR comprises an antibody 237 light chain complementarity determining region 3 sequence comprising the amino acids of positions 96-100 of SEQ ID NO:20.

6. The chimeric antigen receptor of claim 1, wherein the T-cell signaling domain is CD3ζ or FcRγ.

7. The chimeric antigen receptor of claim 6, wherein the FcRγ is FcεRγ.

8. The chimeric antigen receptor of claim 7, further comprising a CD28 transmembrane region, an ICOS transmembrane region, 4-1BB, or OX-40.

9. The chimeric antigen receptor of claim 1, wherein the chimeric antigen receptor comprises the CD28 transmembrane region, and further comprises 4-1BB, OX-40, or Lck.

10. The chimeric antigen receptor of claim 1 wherein the CAR comprises the sequence set forth in SEQ ID NOs: 21, 22, 23 or 24.

11. A soluble cancer-specific 237 single chain variable fragment (scFv) variant that specifically binds a Tn glycopeptide comprising a heavy chain complementarity determining region 1 (CDRH1), a CDRH2, a CDRH3, a light chain complementarity determining region 1 (CDRL1), and a CDRL2 of SEQ ID NO:19, and a variant of a CDRL3 comprising a variant sequence of TTWAP, STWAP, STWSP, STWGP, STWQP, STWEP, SVWEP, STWVP, STHOP, SLGQP, or TNGKP at positions 96-100 of SEQ ID NO: 19.

12. The 237 scFv variant of claim 11, wherein the scFv is a variant of the wild-type scFv of antibody 237 comprising the heavy chain variable region amino acid sequence at positions 127-244 of SEQ ID NO:19 and a variant of the light chain variable region amino acid sequence at positions 1-111 of SEQ ID NO:19, wherein the variant comprises at least one amino acid variation from the wild-type antibody 237 light chain complementarity determining region 3 sequence at positions 96-100 of SEQ ID NO: 19.

13. The 237 scFv variant of claim 11, wherein a nanomolar concentration of the 237 scFv variant detectably binds a Tn epitope or exhibits detectable binding to a target Tn epitope that is not detectably bound by the wild-type 237 scFv at a nanomolar concentration.

14. The 237 scFv variant of claim 11, wherein the scFv is a multimer.

15. The 237 scFv variant of claim 14, wherein the multimer is a tetramer.

16. A cell expressing a detection agent, wherein the detection agent is the soluble scFv variant of claim 13 and wherein a nanomolar or sub-nanomolar concentration of the detection agent detectably binds to a Tn-glycopeptide with truncated glycosylation.

17. An engineered T-cell comprising the CAR of claim 1.

* * * * *

UNITED STATES PATENT AND TRADEMARK OFFICE
CERTIFICATE OF CORRECTION

PATENT NO. : 12,398,192 B2
APPLICATION NO. : 17/250832
DATED : August 26, 2025
INVENTOR(S) : Hans Schreiber et al.

Page 1 of 1

It is certified that error appears in the above-identified patent and that said Letters Patent is hereby corrected as shown below:

In the Claims

In Claim 11, Column 110, Line 64, delete "STHOP" and insert --STHQP-- therefor.

Signed and Sealed this
Twenty-eighth Day of October, 2025

John A. Squires
*Director of the United States Patent and Trademark Office*